(12) United States Patent
Dinh et al.

(10) Patent No.: US 12,324,572 B2
(45) Date of Patent: Jun. 10, 2025

(54) INTEGRATED INSTRUMENT ASSEMBLY

(71) Applicant: Vertos Medical, Inc., Aliso Viejo, CA (US)

(72) Inventors: James Dinh, Irvine, CA (US); Phillip A. Thompson, Pawnee, IL (US); Dennis Schroeder, Los Angeles, CA (US); Brian Roselauf, Rancho Santa Margarita, CA (US); David P. Lalor, Jr., Mission Viejo, CA (US)

(73) Assignee: Vertos Medical, Inc., Aliso Viejo, CA (US)

( * ) Notice: Subject to any disclaimer, the term of this patent is extended or adjusted under 35 U.S.C. 154(b) by 0 days.

(21) Appl. No.: 18/825,442

(22) Filed: Sep. 5, 2024

(65) Prior Publication Data
US 2024/0423601 A1    Dec. 26, 2024

Related U.S. Application Data

(63) Continuation of application No. 18/335,956, filed on Jun. 15, 2023.
(Continued)

(51) Int. Cl.
*A61B 17/34* (2006.01)
*A61B 17/02* (2006.01)
*A61B 17/16* (2006.01)

(52) U.S. Cl.
CPC .......... *A61B 17/02* (2013.01); *A61B 17/1671* (2013.01); *A61B 17/3423* (2013.01); *A61B 2017/0256* (2013.01)

(58) Field of Classification Search
CPC . A61B 17/3421; A61B 17/3423; A61B 17/02; A61B 17/0218; A61B 17/1671
See application file for complete search history.

(56) References Cited

U.S. PATENT DOCUMENTS

| 1,493,240 A | 5/1924 | Bohn |
| 2,670,519 A | 3/1954 | Recklitis |

(Continued)

FOREIGN PATENT DOCUMENTS

| CA | 2574977 C | 1/2010 |
| CH | 709203 A1 | 7/2015 |

(Continued)

OTHER PUBLICATIONS

Basu, S., "Mild Procedure: Single-site Prospective IRB Study" Clinical Journal of Pain, [online], www.clinicalpain.com, Ahead-of-Print publication, doi: 10.1097/AJP.0b013e31822bb344, 2011 (5 pages). Final publication in vol. 28, Issue 3, pp. 254-258, Mar./Apr. 2012.

(Continued)

*Primary Examiner* — Si Ming Ku
(74) *Attorney, Agent, or Firm* — McDonnell Boehnen Hulbert & Berghoff LLP

(57) ABSTRACT

Systems, devices, and methods for performing minimally invasive spinal procedures are described herein. The systems, devices, and methods may be used to percutaneously access the spinal canal and perform a spinal procedure in multiple locations along the canal, e.g., bilaterally and/or at multiple levels from a single access point. The systems and devices may integrate various instruments for performing the procedures, thus improving their ease of use, reducing procedural complexity, and minimizing procedure time.

19 Claims, 30 Drawing Sheets

Related U.S. Application Data

(60) Provisional application No. 63/352,997, filed on Jun. 16, 2022.

(56) References Cited

U.S. PATENT DOCUMENTS

| | | |
|---|---|---|
| 2,842,131 A | 7/1958 | Smith |
| 3,001,522 A | 9/1961 | Silverman |
| 3,628,524 A | 12/1971 | Jamshidi |
| 3,683,892 A | 8/1972 | Harris |
| 3,732,858 A | 5/1973 | Banko |
| 3,893,445 A | 7/1975 | Hofsess |
| 3,902,498 A | 9/1975 | Niederer |
| 3,929,123 A | 12/1975 | Jamshidi |
| 3,945,372 A | 3/1976 | Milan et al. |
| 3,989,033 A | 11/1976 | Halpern et al. |
| 4,103,690 A | 8/1978 | Harris |
| 4,174,715 A | 11/1979 | Hasson |
| 4,200,111 A | 4/1980 | Harris |
| 4,201,213 A | 5/1980 | Townsend |
| 4,283,129 A | 8/1981 | Bennick, Jr. |
| 4,355,931 A | 10/1982 | Leuenberger |
| 4,425,908 A | 1/1984 | Simon |
| 4,519,794 A | 5/1985 | Sneider |
| 4,522,206 A | 6/1985 | Whipple et al. |
| 4,535,773 A | 8/1985 | Yoon et al. |
| 4,603,694 A | 8/1986 | Wheeler |
| 4,651,752 A | 3/1987 | Fuerst |
| 4,682,606 A | 7/1987 | DeCaprio |
| 4,708,147 A | 11/1987 | Haaga |
| 4,733,663 A | 3/1988 | Farley |
| 4,777,948 A | 10/1988 | Wright |
| 4,782,833 A | 11/1988 | Einhorn et al. |
| 4,801,293 A | 1/1989 | Jackson |
| 4,811,734 A | 3/1989 | McGurk-Burleson et al. |
| 4,834,729 A | 5/1989 | Sjostrom |
| 4,844,064 A | 7/1989 | Thimsen et al. |
| 4,850,354 A | 7/1989 | McGurk-Burleson et al. |
| 4,867,157 A | 9/1989 | McGurk-Burleson et al. |
| 4,911,600 A | 3/1990 | Zelinka et al. |
| 4,926,877 A | 5/1990 | Bookwalter |
| 4,931,059 A | 6/1990 | Markham |
| 4,986,825 A | 1/1991 | Bays et al. |
| 4,991,600 A | 2/1991 | Taylor |
| 4,994,072 A | 2/1991 | Bhate et al. |
| 5,026,375 A | 6/1991 | Linovitz et al. |
| 5,026,386 A | 6/1991 | Michelson |
| 5,040,542 A | 8/1991 | Gray |
| 5,061,269 A | 10/1991 | Muller |
| 5,098,435 A | 3/1992 | Stednitz et al. |
| 5,108,403 A | 4/1992 | Stern |
| 5,127,916 A | 7/1992 | Spencer et al. |
| 5,172,702 A | 12/1992 | Leigh et al. |
| 5,180,393 A | 1/1993 | Commarmond |
| 5,190,759 A | 3/1993 | Lindblad et al. |
| 5,215,105 A | 6/1993 | Kizelshteyn et al. |
| 5,224,488 A | 7/1993 | Neuffer |
| 5,226,426 A | 7/1993 | Yoon |
| 5,226,910 A | 7/1993 | Kajiyama et al. |
| 5,269,785 A | 12/1993 | Bonutti |
| 5,273,519 A | 12/1993 | Koros et al. |
| 5,281,230 A | 1/1994 | Heidmueller |
| 5,282,822 A | 2/1994 | Macors et al. |
| 5,286,255 A | 2/1994 | Weber |
| 5,290,303 A | 3/1994 | Pingleton et al. |
| 5,295,974 A | 3/1994 | O'Laughlin |
| 5,300,045 A | 4/1994 | Plassche, Jr. |
| D347,474 S | 5/1994 | Olson |
| 5,320,110 A | 6/1994 | Wang |
| 5,327,896 A | 7/1994 | Schmieding |
| 5,354,266 A | 10/1994 | Snoke |
| 5,356,421 A | 10/1994 | Castro |
| 5,366,477 A | 11/1994 | LeMarie et al. |
| 5,372,583 A | 12/1994 | Roberts et al. |
| 5,373,854 A | 12/1994 | Kolozsi |
| 5,385,570 A | 1/1995 | Chin et al. |
| D358,645 S | 5/1995 | Ryan et al. |
| 5,429,136 A | 7/1995 | Milo et al. |
| 5,429,138 A | 7/1995 | Jamshidi |
| 5,437,645 A | 8/1995 | Urban et al. |
| 5,439,464 A | 8/1995 | Shapiro |
| 5,445,639 A | 8/1995 | Kuslich et al. |
| 5,451,227 A | 9/1995 | Michelson |
| 5,458,112 A | 10/1995 | Weaver |
| 5,462,062 A | 10/1995 | Rubinstein et al. |
| 5,484,437 A | 1/1996 | Michelson |
| 5,484,446 A | 1/1996 | Burke et al. |
| 5,496,269 A | 3/1996 | Snoke |
| 5,514,379 A | 5/1996 | Weissleder et al. |
| 5,522,825 A | 6/1996 | Kropf et al. |
| 5,531,749 A | 7/1996 | Michelson |
| 5,538,008 A | 7/1996 | Crowe |
| 5,540,693 A | 7/1996 | Fisher |
| 5,562,102 A | 10/1996 | Taylor |
| 5,569,258 A | 10/1996 | Gambale |
| 5,569,284 A | 10/1996 | Young et al. |
| 5,575,794 A | 11/1996 | Walus et al. |
| 5,578,030 A | 11/1996 | Levin |
| 5,582,618 A | 12/1996 | Chin et al. |
| 5,595,186 A | 1/1997 | Rubinstein et al. |
| 5,601,585 A | 2/1997 | Banik et al. |
| 5,613,972 A | 3/1997 | Lee et al. |
| 5,637,096 A | 6/1997 | Yoon |
| 5,638,827 A | 6/1997 | Palmer et al. |
| 5,645,075 A | 7/1997 | Palmer et al. |
| 5,649,547 A | 7/1997 | Ritchart et al. |
| 5,681,337 A | 10/1997 | Bray, Jr. |
| 5,705,485 A | 1/1998 | Cini et al. |
| 5,709,697 A | 1/1998 | Ratcliff et al. |
| 5,714,997 A | 2/1998 | Anderson |
| 5,718,237 A | 2/1998 | Haaga |
| 5,722,977 A | 3/1998 | Wilhelmy |
| 5,730,754 A | 3/1998 | Obenchain |
| 5,735,865 A | 4/1998 | Schaumann et al. |
| 5,755,448 A | 5/1998 | Kanaan et al. |
| 5,759,185 A | 6/1998 | Grinberg |
| 5,762,639 A | 6/1998 | Gibbs |
| 5,772,597 A | 6/1998 | Goldberger et al. |
| 5,775,333 A | 7/1998 | Burbank et al. |
| 5,776,075 A | 7/1998 | Palmer |
| 5,782,764 A | 7/1998 | Werne |
| 5,782,849 A | 7/1998 | Miller |
| 5,792,044 A | 8/1998 | Foley et al. |
| 5,797,936 A | 8/1998 | Kleihues |
| 5,797,939 A | 8/1998 | Yoon |
| 5,797,958 A | 8/1998 | Yoon |
| 5,823,970 A | 10/1998 | Terwilliger |
| 5,827,289 A | 10/1998 | Reiley et al. |
| 5,827,305 A | 10/1998 | Gordon |
| 5,836,948 A | 11/1998 | Zucherman et al. |
| 5,840,338 A | 11/1998 | Roos et al. |
| 5,843,121 A | 12/1998 | Yoon |
| 5,851,214 A | 12/1998 | Larsen et al. |
| 5,853,366 A | 12/1998 | Dowlatshahi |
| 5,857,996 A | 1/1999 | Snoke |
| 5,860,991 A | 1/1999 | Klein et al. |
| 5,868,745 A | 2/1999 | Alleyne |
| 5,871,453 A | 2/1999 | Banik et al. |
| 5,873,886 A | 2/1999 | Larsen et al. |
| 5,876,405 A | 3/1999 | Del et al. |
| 5,879,353 A | 3/1999 | Terry |
| 5,879,365 A | 3/1999 | Whitfield et al. |
| 5,904,699 A | 5/1999 | Schwemberger et al. |
| 5,916,858 A | 6/1999 | Kim et al. |
| 5,925,050 A | 7/1999 | Howard, III |
| 5,925,056 A | 7/1999 | Thomas et al. |
| 5,928,164 A | 7/1999 | Burbank et al. |
| 5,931,855 A | 8/1999 | Buncke |
| 5,954,739 A | 9/1999 | Bonutti |
| 5,961,534 A | 10/1999 | Banik et al. |
| 5,964,782 A | 10/1999 | Lafontaine et al. |
| 5,980,493 A | 11/1999 | Smith et al. |
| 5,980,525 A | 11/1999 | Bryant et al. |
| 5,984,939 A | 11/1999 | Yoon |
| 5,985,320 A | 11/1999 | Edwards et al. |

(56) References Cited

U.S. PATENT DOCUMENTS

| | | |
|---|---|---|
| 6,010,493 A | 1/2000 | Snoke |
| D420,132 S | 2/2000 | Bucholz et al. |
| 6,019,765 A | 2/2000 | Thornhill et al. |
| 6,022,354 A | 2/2000 | Mercuri et al. |
| 6,022,362 A | 2/2000 | Lee et al. |
| 6,037,724 A | 3/2000 | Buss et al. |
| 6,045,580 A | 4/2000 | Scarborough et al. |
| 6,053,877 A | 4/2000 | Banik et al. |
| 6,083,237 A | 7/2000 | Huitema et al. |
| 6,096,053 A | 8/2000 | Bates |
| 6,110,127 A | 8/2000 | Suzuki |
| 6,139,508 A | 10/2000 | Simpson et al. |
| 6,139,608 A | 10/2000 | Woodbridge et al. |
| 6,142,957 A | 11/2000 | Diamond et al. |
| 6,142,997 A | 11/2000 | Michelson |
| 6,162,170 A | 12/2000 | Foley et al. |
| 6,214,010 B1 | 4/2001 | Farley et al. |
| 6,221,006 B1 | 4/2001 | Dubrul et al. |
| 6,238,407 B1 | 5/2001 | Wolf et al. |
| 6,241,747 B1 | 6/2001 | Ruff |
| 6,258,093 B1 | 7/2001 | Edwards et al. |
| 6,261,294 B1 | 7/2001 | Stihl et al. |
| 6,261,582 B1 | 7/2001 | Needham et al. |
| 6,264,087 B1 | 7/2001 | Whitman |
| 6,264,617 B1 | 7/2001 | Bales et al. |
| 6,264,650 B1 | 7/2001 | Hovda et al. |
| 6,268,405 B1 | 7/2001 | Yao et al. |
| 6,273,862 B1 | 8/2001 | Privitera et al. |
| 6,287,304 B1 | 9/2001 | Eggers et al. |
| 6,296,639 B1 | 10/2001 | Truckai et al. |
| 6,299,131 B1 | 10/2001 | Ryan |
| 6,306,156 B1 | 10/2001 | Clark |
| 6,332,886 B1 | 12/2001 | Green et al. |
| D454,951 S | 3/2002 | Bon |
| 6,358,217 B1 | 3/2002 | Bourassa |
| 6,358,254 B1 | 3/2002 | Anderson |
| 6,371,968 B1 | 4/2002 | Kogasaka et al. |
| 6,375,659 B1 | 4/2002 | Erbe et al. |
| D460,553 S | 7/2002 | Koros et al. |
| 6,419,661 B1 | 7/2002 | Kuhr et al. |
| 6,419,684 B1 | 7/2002 | Heisler et al. |
| 6,423,332 B1 | 7/2002 | Huxel et al. |
| 6,425,859 B1 | 7/2002 | Foley et al. |
| 6,428,486 B2 | 8/2002 | Ritchart et al. |
| 6,428,498 B2 | 8/2002 | Uflacker |
| 6,443,910 B1 | 9/2002 | Krueger et al. |
| 6,454,767 B2 | 9/2002 | Alleyne |
| 6,464,682 B1 | 10/2002 | Snoke |
| 6,470,209 B2 | 10/2002 | Snoke |
| D465,281 S | 11/2002 | Lang |
| D466,209 S | 11/2002 | Bon |
| 6,478,805 B1 | 11/2002 | Marino et al. |
| D466,609 S | 12/2002 | Glossop |
| 6,488,636 B2 | 12/2002 | Bryan et al. |
| 6,490,467 B1 | 12/2002 | Bucholz et al. |
| 6,494,892 B1 | 12/2002 | Ireland et al. |
| 6,506,190 B1 | 1/2003 | Walshe |
| 6,514,256 B2 | 2/2003 | Zucherman et al. |
| 6,520,907 B1 | 2/2003 | Foley et al. |
| 6,530,933 B1 | 3/2003 | Yeung et al. |
| 6,533,795 B1 | 3/2003 | Tran et al. |
| 6,565,583 B1 | 5/2003 | Deaton et al. |
| 6,572,563 B2 | 6/2003 | Ouchi |
| 6,575,919 B1 | 6/2003 | Reiley et al. |
| 6,575,968 B1 | 6/2003 | Eggers et al. |
| 6,575,977 B1 | 6/2003 | Michelson |
| 6,575,978 B2 | 6/2003 | Peterson et al. |
| 6,579,291 B1 | 6/2003 | Keith et al. |
| 6,599,310 B2 | 7/2003 | Leung et al. |
| D478,986 S | 8/2003 | Johnston et al. |
| 6,602,248 B1 | 8/2003 | Sharps et al. |
| 6,605,294 B2 | 8/2003 | Sawhney |
| 6,620,185 B1 | 9/2003 | Harvie et al. |
| 6,626,916 B1 | 9/2003 | Yeung et al. |
| 6,632,182 B1 | 10/2003 | Treat |
| 6,645,213 B2 | 11/2003 | Sand et al. |
| 6,652,558 B2 | 11/2003 | Patel et al. |
| D484,597 S | 12/2003 | Koros et al. |
| 6,669,729 B2 | 12/2003 | Chin |
| D484,975 S | 1/2004 | Belokin |
| 6,682,535 B2 | 1/2004 | Hoogland |
| 6,692,445 B2 | 2/2004 | Roberts et al. |
| 6,716,216 B1 | 4/2004 | Boucher et al. |
| 6,733,218 B2 | 5/2004 | Del et al. |
| 6,746,093 B2 | 6/2004 | Martinez |
| 6,746,451 B2 | 6/2004 | Middleton et al. |
| D493,527 S | 7/2004 | Szabo |
| 6,772,012 B2 | 8/2004 | Ricart et al. |
| 6,783,534 B2 | 8/2004 | Mehdizadeh |
| D497,427 S | 10/2004 | Hickingbotham |
| 6,818,001 B2 | 11/2004 | Wulfman et al. |
| 6,852,095 B1 | 2/2005 | Ray |
| 6,858,229 B1 | 2/2005 | Hubbell et al. |
| D502,541 S | 3/2005 | Abry |
| 6,896,686 B2 | 5/2005 | Weber et al. |
| 6,925,323 B2 | 8/2005 | Snoke |
| 6,939,351 B2 | 9/2005 | Eckman |
| 6,991,633 B2 | 1/2006 | Agbodoe |
| 7,001,396 B2 | 2/2006 | Glazier et al. |
| 7,008,433 B2 | 3/2006 | Voellmicke et al. |
| 7,011,663 B2 | 3/2006 | Michelson |
| 7,025,771 B2 | 4/2006 | Kuslich et al. |
| 7,041,050 B1 | 5/2006 | Ronald |
| 7,066,942 B2 | 6/2006 | Treace |
| 7,070,596 B1 | 7/2006 | Woloszko et al. |
| 7,101,382 B2 | 9/2006 | George et al. |
| 7,104,986 B2 | 9/2006 | Hovda et al. |
| D531,310 S | 10/2006 | Wolter et al. |
| 7,118,576 B2 | 10/2006 | Gitis et al. |
| D532,515 S | 11/2006 | Buettler et al. |
| 7,131,951 B2 | 11/2006 | Angel |
| 7,137,956 B2 | 11/2006 | Nishtalas et al. |
| D533,664 S | 12/2006 | Buettler et al. |
| 7,169,155 B2 | 1/2007 | Chu et al. |
| 7,181,289 B2 | 2/2007 | Pflueger et al. |
| 7,189,206 B2 | 3/2007 | Quick et al. |
| 7,189,240 B1 | 3/2007 | Dekel |
| D541,418 S | 4/2007 | Schechter et al. |
| 7,201,722 B2 | 4/2007 | Krueger |
| 7,211,100 B2 | 5/2007 | Hanson |
| 7,226,424 B2 | 6/2007 | Ritchart et al. |
| 7,226,444 B1 | 6/2007 | Ellman et al. |
| D547,451 S | 7/2007 | Asfora |
| 7,276,032 B2 | 10/2007 | Hibner |
| 7,297,147 B2 | 11/2007 | Michelson |
| 7,309,338 B2 | 12/2007 | Cragg |
| 7,322,978 B2 | 1/2008 | West, Jr. |
| 7,329,402 B2 | 2/2008 | Unger et al. |
| D568,993 S | 5/2008 | Melanson et al. |
| D573,252 S | 7/2008 | Peretti et al. |
| 7,404,822 B2 | 7/2008 | Mart et al. |
| D575,273 S | 8/2008 | Cherry, II |
| D576,273 S | 9/2008 | McClintok et al. |
| 7,431,342 B2 | 10/2008 | Sauer |
| 7,445,634 B2 | 11/2008 | Trieu |
| D583,051 S | 12/2008 | Lee et al. |
| D583,941 S | 12/2008 | Leroy |
| 7,500,811 B2 | 3/2009 | Pfob |
| 7,517,358 B2 | 4/2009 | Petersen |
| 7,553,307 B2 | 6/2009 | Bleich et al. |
| D606,594 S | 12/2009 | Guinchard et al. |
| D606,654 S | 12/2009 | Tran et al. |
| D610,259 S | 2/2010 | Way et al. |
| D611,146 S | 3/2010 | Way et al. |
| 7,699,849 B2 | 4/2010 | Eckman |
| D618,796 S | 6/2010 | Cantu et al. |
| D619,252 S | 7/2010 | Way et al. |
| D619,253 S | 7/2010 | Way et al. |
| D620,593 S | 7/2010 | Tran et al. |
| 7,758,581 B2 | 7/2010 | Chervitz et al. |
| 7,763,074 B2 | 7/2010 | Altarac et al. |
| D621,939 S | 8/2010 | Way et al. |
| 7,776,094 B2 | 8/2010 | McKinley et al. |
| D627,461 S | 11/2010 | Cantu et al. |

(56) References Cited

U.S. PATENT DOCUMENTS

| | | |
|---|---|---|
| 7,837,713 B2 | 11/2010 | Petersen |
| 7,862,589 B2 | 1/2011 | Thramann |
| 7,887,538 B2 | 2/2011 | Bleich et al. |
| 7,892,174 B2 | 2/2011 | Hestad et al. |
| 7,896,879 B2 | 3/2011 | Solsberg et al. |
| D635,671 S | 4/2011 | Way et al. |
| 7,922,727 B2 | 4/2011 | Songer et al. |
| 7,938,830 B2 | 5/2011 | Saadat et al. |
| 7,942,830 B2 | 5/2011 | Solsberg et al. |
| 7,963,915 B2 | 6/2011 | Bleich |
| 7,976,464 B2 | 7/2011 | Shluzas et al. |
| 7,985,247 B2 | 7/2011 | Shluzas et al. |
| 7,993,378 B2 | 8/2011 | Foley et al. |
| 8,007,492 B2 | 8/2011 | DiPoto et al. |
| 8,007,517 B2 | 8/2011 | Lins et al. |
| RE42,757 E | 9/2011 | Kuslich et al. |
| 8,012,207 B2 | 9/2011 | Kim |
| 8,021,392 B2 | 9/2011 | Petersen |
| 8,038,699 B2 | 10/2011 | Cohen et al. |
| 8,052,728 B2 | 11/2011 | Hestad |
| 8,062,300 B2 | 11/2011 | Schmitz et al. |
| 8,088,148 B2 | 1/2012 | Falahee |
| 8,092,456 B2 | 1/2012 | Bleich et al. |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,206,292 B2 | 6/2012 | Eckman |
| 8,246,654 B2 | 8/2012 | Varela |
| 8,257,356 B2 | 9/2012 | Bleich et al. |
| 8,308,728 B2 | 11/2012 | Iott et al. |
| D676,964 S | 2/2013 | Way et al. |
| 8,394,102 B2 | 3/2013 | Garabedian et al. |
| 8,398,641 B2 | 3/2013 | Wallace et al. |
| 8,409,206 B2 | 4/2013 | Wallace et al. |
| 8,419,738 B2 | 4/2013 | Smisson, III et al. |
| 8,430,881 B2 | 4/2013 | Bleich et al. |
| 8,449,546 B2 | 5/2013 | Ries |
| 8,460,300 B2 | 6/2013 | Hestad et al. |
| 8,475,461 B2 | 7/2013 | Butler et al. |
| 8,480,680 B2 | 7/2013 | Lewis |
| 8,523,865 B2 | 9/2013 | Reglos et al. |
| 8,540,746 B2 | 9/2013 | Davison et al. |
| 8,574,266 B2 | 11/2013 | Falahee |
| 8,579,902 B2 | 11/2013 | Bleich et al. |
| 8,591,547 B2 | 11/2013 | Smisson, III et al. |
| 8,608,651 B2 | 12/2013 | Shluzas |
| 8,608,762 B2 | 12/2013 | Solsberg et al. |
| 8,623,021 B2 | 1/2014 | Ries et al. |
| 8,623,024 B2 | 1/2014 | Smisson, III et al. |
| 8,641,609 B2 | 2/2014 | Hestad et al. |
| 8,696,671 B2 | 4/2014 | Solsberg et al. |
| 8,696,706 B2 | 4/2014 | Falahee |
| 8,702,709 B2 | 4/2014 | Osman |
| 8,728,162 B2 | 5/2014 | Akyuz et al. |
| 8,734,477 B2 | 5/2014 | Solsberg et al. |
| 8,758,409 B2 | 6/2014 | Hochschuler et al. |
| 8,764,754 B2 | 7/2014 | Butler et al. |
| 8,801,739 B2 | 8/2014 | Batten et al. |
| 8,808,307 B2 | 8/2014 | Robinson |
| 8,821,378 B2 | 9/2014 | Morgenstern et al. |
| 8,821,502 B2 | 9/2014 | Gleeson et al. |
| 8,845,639 B2 | 9/2014 | Wallace et al. |
| 8,882,772 B2 | 11/2014 | Solsberg et al. |
| 8,894,653 B2 | 11/2014 | Solsberg et al. |
| 8,945,184 B2 | 2/2015 | Hess et al. |
| 8,992,524 B1 | 3/2015 | Ellman |
| 8,998,906 B2 | 4/2015 | Kirschman |
| 9,017,389 B2 | 4/2015 | Assell et al. |
| 9,078,707 B2 | 7/2015 | Helgerson |
| 9,101,369 B2 | 8/2015 | Ries |
| 9,101,386 B2 | 8/2015 | Wallace et al. |
| 9,113,854 B2 | 8/2015 | Ellman |
| 9,125,682 B2 | 9/2015 | Bleich et al. |
| 9,204,896 B2 | 12/2015 | Williams |
| 9,220,543 B2 | 12/2015 | Walker et al. |
| 9,226,781 B2 | 1/2016 | Smisson, III et al. |
| 9,233,006 B2 | 1/2016 | Assell et al. |
| 9,247,952 B2 | 2/2016 | Bleich et al. |
| 9,265,491 B2 | 2/2016 | Lins et al. |
| 9,265,517 B2 | 2/2016 | Yoon et al. |
| 9,265,540 B2 | 2/2016 | Kirschman |
| 9,314,253 B2 | 4/2016 | Mimran et al. |
| 9,314,276 B2 | 4/2016 | Hess et al. |
| 9,314,277 B2 | 4/2016 | Assell et al. |
| 9,320,618 B2 | 4/2016 | Schmitz et al. |
| 9,326,777 B2 | 5/2016 | Tally |
| 9,345,491 B2 | 5/2016 | Bleich et al. |
| 9,351,739 B2 | 5/2016 | Mahoney et al. |
| 9,351,741 B2 | 5/2016 | Schmitz et al. |
| 9,357,985 B2 | 6/2016 | Bertagnoli |
| 9,358,048 B2 | 6/2016 | Jensen et al. |
| 9,370,348 B2 | 6/2016 | Tally et al. |
| 9,370,379 B2 | 6/2016 | Osman |
| 9,393,057 B2 | 7/2016 | MacMillan et al. |
| 9,421,020 B2 | 8/2016 | Blain et al. |
| 9,456,829 B2 | 10/2016 | Saadat et al. |
| 9,456,830 B2 | 10/2016 | Greenhalgh |
| 9,456,846 B2 | 10/2016 | Predick |
| 9,463,029 B2 | 10/2016 | Schmitz et al. |
| 9,463,041 B2 | 10/2016 | Bleich et al. |
| 9,480,472 B2 | 11/2016 | Bjork et al. |
| 9,492,151 B2 | 11/2016 | Bleich et al. |
| 9,517,077 B2 | 12/2016 | Blain et al. |
| 9,526,536 B2 | 12/2016 | Gleason et al. |
| 9,561,061 B2 | 2/2017 | Smisson, III et al. |
| 9,610,095 B2 | 4/2017 | To |
| 9,649,129 B2 | 5/2017 | Park |
| 9,649,138 B2 | 5/2017 | Altarac et al. |
| 9,681,889 B1 * | 6/2017 | Greenhalgh ....... A61B 17/3421 |
| 9,743,937 B2 | 8/2017 | Blain et al. |
| 9,801,641 B2 | 10/2017 | Keiser et al. |
| 9,814,494 B2 | 11/2017 | Lins |
| 9,861,399 B2 | 1/2018 | Rogers et al. |
| 9,867,605 B2 | 1/2018 | Adams |
| 9,883,894 B2 | 2/2018 | Smisson, III et al. |
| 9,907,581 B2 | 3/2018 | Hess et al. |
| 9,924,953 B2 | 3/2018 | Schmitz et al. |
| 9,956,011 B2 | 5/2018 | Altarac et al. |
| 9,962,211 B2 | 5/2018 | Csernatoni |
| 9,968,381 B2 | 5/2018 | Thalgott et al. |
| 10,004,542 B2 | 6/2018 | Field et al. |
| 10,010,354 B2 | 7/2018 | Field et al. |
| 10,022,162 B2 | 7/2018 | Smisson, III et al. |
| 10,022,163 B2 | 7/2018 | Smisson, III et al. |
| 10,052,116 B2 | 8/2018 | Wallace et al. |
| 10,123,810 B2 | 11/2018 | Wolters et al. |
| 10,285,747 B2 | 5/2019 | Reimels |
| 10,342,677 B2 | 7/2019 | Ries |
| 10,357,374 B2 | 7/2019 | Lowry et al. |
| 10,390,968 B2 | 8/2019 | Ries |
| 10,398,478 B2 | 9/2019 | Ganter et al. |
| 10,492,801 B2 | 12/2019 | Gonzalez et al. |
| 10,524,772 B2 | 1/2020 | Choi et al. |
| 10,532,197 B2 | 1/2020 | Predick |
| 10,543,004 B2 | 1/2020 | Viola et al. |
| 10,588,663 B2 | 3/2020 | Tebbe et al. |
| 10,595,911 B1 | 3/2020 | Horton et al. |
| 10,610,267 B2 | 4/2020 | Altarac et al. |
| 10,617,441 B2 | 4/2020 | Tran et al. |
| 10,653,458 B2 | 5/2020 | Tanaka et al. |
| 10,682,243 B2 | 6/2020 | Phan et al. |
| 10,687,828 B2 | 6/2020 | Greenhalgh et al. |
| 10,842,554 B2 | 11/2020 | Ellman |
| 10,856,910 B2 | 12/2020 | Rice et al. |
| 10,874,447 B2 | 12/2020 | Tanaka et al. |
| 10,893,954 B2 | 1/2021 | Taylor et al. |
| 10,939,934 B2 | 3/2021 | Lockard et al. |
| 11,065,045 B2 | 7/2021 | Seifert et al. |
| 11,090,068 B2 | 8/2021 | Giri et al. |
| 11,096,709 B1 | 8/2021 | Chin et al. |
| 11,129,655 B2 | 9/2021 | Crossgrove et al. |
| 11,219,498 B2 | 1/2022 | Csernatoni |
| 11,224,465 B2 | 1/2022 | Grob |

(56) References Cited

U.S. PATENT DOCUMENTS

| | | |
|---|---|---|
| 11,298,160 B2 | 4/2022 | Bosio et al. |
| 11,317,934 B2 | 5/2022 | Tran et al. |
| 11,331,108 B2 | 5/2022 | Ries et al. |
| 11,331,199 B2 | 5/2022 | Northcutt et al. |
| 11,376,135 B2 | 7/2022 | Ziemek et al. |
| 11,382,647 B2 | 7/2022 | Wallace et al. |
| 11,413,163 B2 | 8/2022 | Robinson |
| 11,510,704 B2 | 11/2022 | Iott et al. |
| 11,547,424 B2 | 1/2023 | Ries |
| 11,547,578 B2 | 1/2023 | Malcolmson et al. |
| 11,583,419 B2 | 2/2023 | Palagi et al. |
| 11,596,393 B2 | 3/2023 | Liu et al. |
| 11,648,128 B2 | 5/2023 | Tanaka et al. |
| 11,653,962 B2 | 5/2023 | Mohar et al. |
| 11,696,786 B2 | 7/2023 | Perrow et al. |
| 11,696,838 B2 | 7/2023 | Perrow |
| 11,751,861 B2 | 9/2023 | Friedrich et al. |
| 11,826,055 B2 | 11/2023 | Zille et al. |
| 11,826,268 B2 | 11/2023 | Kahmer |
| 11,849,931 B2 | 12/2023 | DiPoto et al. |
| 11,925,341 B2 | 3/2024 | Friedrich et al. |
| 11,931,269 B2 | 3/2024 | Salvermoser et al. |
| 11,957,362 B2 | 4/2024 | Glerum et al. |
| 2001/0005778 A1 | 6/2001 | Ouchi |
| 2001/0029370 A1 | 10/2001 | Hodva et al. |
| 2001/0044635 A1 | 11/2001 | Niizeki et al. |
| 2002/0022764 A1 | 2/2002 | Smith et al. |
| 2002/0054915 A1 | 5/2002 | Goldenheim et al. |
| 2002/0091387 A1 | 7/2002 | Hoogland |
| 2003/0004528 A1 | 1/2003 | Ishikawa |
| 2003/0009125 A1 | 1/2003 | Nita et al. |
| 2003/0050574 A1 | 3/2003 | Krueger |
| 2003/0077225 A1 | 4/2003 | Laurent et al. |
| 2003/0165555 A1 | 9/2003 | Ding et al. |
| 2003/0171681 A1 | 9/2003 | Weilandt |
| 2003/0220650 A1 | 11/2003 | Major et al. |
| 2004/0002724 A1 | 1/2004 | Falahee |
| 2004/0024398 A1 | 2/2004 | Hovda et al. |
| 2004/0044359 A1 | 3/2004 | Renati et al. |
| 2004/0049217 A1 | 3/2004 | Ross et al. |
| 2004/0059370 A1 | 3/2004 | Greene et al. |
| 2004/0133201 A1 | 7/2004 | Shluzas et al. |
| 2004/0138701 A1 | 7/2004 | Haluck |
| 2004/0193112 A1 | 9/2004 | Glazier et al. |
| 2004/0210231 A1 | 10/2004 | Boucher et al. |
| 2004/0243146 A1 | 12/2004 | Chesbrough et al. |
| 2004/0260312 A1 | 12/2004 | Magnusson et al. |
| 2005/0037079 A1 | 2/2005 | Son et al. |
| 2005/0038432 A1 | 2/2005 | Shaolian et al. |
| 2005/0038447 A1 | 2/2005 | Huffmaster |
| 2005/0038465 A1 | 2/2005 | Shraga |
| 2005/0038466 A1 | 2/2005 | O'Heeron et al. |
| 2005/0070913 A1 | 3/2005 | Milbocker et al. |
| 2005/0075630 A1 | 4/2005 | Truckai et al. |
| 2005/0080441 A1 | 4/2005 | Dodge et al. |
| 2005/0131442 A1 | 6/2005 | Yachia et al. |
| 2005/0137602 A1 | 6/2005 | Assell et al. |
| 2005/0163850 A1 | 7/2005 | Wong et al. |
| 2005/0197661 A1 | 9/2005 | Carrison et al. |
| 2005/0209610 A1 | 9/2005 | Carrison |
| 2005/0228403 A1 | 10/2005 | Ho et al. |
| 2005/0261692 A1 | 11/2005 | Carrison et al. |
| 2005/0267503 A1 | 12/2005 | Hunstad |
| 2005/0273167 A1 | 12/2005 | Triplett et al. |
| 2006/0004369 A1 | 1/2006 | Patel et al. |
| 2006/0030785 A1 | 2/2006 | Field et al. |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0052811 A1 | 3/2006 | Blanco |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0094976 A1 | 5/2006 | Bleich |
| 2006/0095028 A1 | 5/2006 | Bleich |
| 2006/0095059 A1 | 5/2006 | Bleich et al. |
| 2006/0100651 A1 | 5/2006 | Bleich |
| 2006/0111723 A1 | 5/2006 | Chapolini et al. |
| 2006/0122458 A1 | 6/2006 | Bleich |
| 2006/0122535 A1 | 6/2006 | Daum |
| 2006/0135882 A1 | 6/2006 | Bleich |
| 2006/0178682 A1 | 8/2006 | Boehlke |
| 2006/0184175 A1 | 8/2006 | Schomer et al. |
| 2006/0184192 A1 | 8/2006 | Markworth et al. |
| 2006/0206115 A1 | 9/2006 | Schomer et al. |
| 2006/0206178 A1 | 9/2006 | Kim |
| 2006/0224160 A1 | 10/2006 | Trieu et al. |
| 2006/0235334 A1 | 10/2006 | Corvi et al. |
| 2006/0235422 A1 | 10/2006 | Keller |
| 2006/0235451 A1 | 10/2006 | Schomer et al. |
| 2006/0235452 A1 | 10/2006 | Schomer et al. |
| 2006/0264994 A1 | 11/2006 | Schomer et al. |
| 2007/0005084 A1 | 1/2007 | Clague et al. |
| 2007/0010843 A1* | 1/2007 | Green ............... A61B 17/3421 606/167 |
| 2007/0027464 A1 | 2/2007 | Way et al. |
| 2007/0055215 A1 | 3/2007 | Tran et al. |
| 2007/0055263 A1 | 3/2007 | Way et al. |
| 2007/0060935 A1 | 3/2007 | Schwardt et al. |
| 2007/0066987 A1 | 3/2007 | Scanlan et al. |
| 2007/0106283 A1 | 5/2007 | Garcia et al. |
| 2007/0123888 A1 | 5/2007 | Bleich et al. |
| 2007/0123890 A1 | 5/2007 | Way et al. |
| 2007/0123891 A1 | 5/2007 | Ries et al. |
| 2007/0162061 A1 | 7/2007 | Way et al. |
| 2007/0198019 A1 | 8/2007 | Schomer et al. |
| 2007/0213735 A1 | 9/2007 | Saadat et al. |
| 2007/0225703 A1 | 9/2007 | Schmitz et al. |
| 2007/0260253 A1 | 11/2007 | Johnson et al. |
| 2007/0270775 A1 | 11/2007 | Miller et al. |
| 2007/0276390 A1 | 11/2007 | Solsberg et al. |
| 2007/0299459 A1 | 12/2007 | Way et al. |
| 2008/0161809 A1 | 7/2008 | Schmitz et al. |
| 2008/0200798 A1 | 8/2008 | Eklund et al. |
| 2008/0200941 A1 | 8/2008 | Mitusina |
| 2008/0221383 A1 | 9/2008 | Way et al. |
| 2008/0243117 A1 | 10/2008 | Sharps et al. |
| 2009/0036936 A1 | 2/2009 | Solsberg et al. |
| 2009/0054898 A1 | 2/2009 | Gleason |
| 2009/0112261 A1 | 4/2009 | Barry |
| 2009/0118709 A1 | 5/2009 | Sand et al. |
| 2009/0143807 A1 | 6/2009 | Sand |
| 2009/0200406 A1 | 8/2009 | Kronberger |
| 2009/0247859 A1 | 10/2009 | Daum et al. |
| 2009/0287221 A1 | 11/2009 | Sand et al. |
| 2010/0030232 A1 | 2/2010 | Zehavi et al. |
| 2010/0042111 A1 | 2/2010 | Qureshi et al. |
| 2010/0094231 A1 | 4/2010 | Bleich et al. |
| 2010/0130983 A1 | 5/2010 | Thornhill et al. |
| 2010/0312103 A1 | 12/2010 | Gorek et al. |
| 2010/0331883 A1 | 12/2010 | Schmitz et al. |
| 2011/0084971 A1 | 4/2011 | Kuo et al. |
| 2011/0301647 A1 | 12/2011 | Hua |
| 2012/0101511 A1 | 4/2012 | You et al. |
| 2012/0215229 A1 | 8/2012 | Garcia-Bengochea et al. |
| 2012/0226301 A1 | 9/2012 | Geist |
| 2013/0053834 A1 | 2/2013 | Meyer et al. |
| 2013/0289399 A1 | 10/2013 | Choi et al. |
| 2014/0005671 A1 | 1/2014 | Solsberg et al. |
| 2014/0018674 A1 | 1/2014 | Solsberg et al. |
| 2014/0024933 A1 | 1/2014 | Solsberg et al. |
| 2014/0114315 A1 | 4/2014 | Leguidleguid et al. |
| 2014/0172029 A1 | 6/2014 | Guyer et al. |
| 2014/0336716 A1 | 11/2014 | Seegert et al. |
| 2014/0364863 A1 | 12/2014 | Prien |
| 2015/0038973 A1 | 2/2015 | Grim |
| 2015/0066042 A1 | 3/2015 | Cummins et al. |
| 2015/0245925 A1 | 9/2015 | Willyerd et al. |
| 2015/0257784 A1 | 9/2015 | Corbin et al. |
| 2015/0272650 A1 | 10/2015 | Dubois |
| 2015/0342591 A1 | 12/2015 | Bleich et al. |
| 2015/0359570 A1 | 12/2015 | Ries |
| 2016/0015415 A1 | 1/2016 | Wolff |
| 2016/0081775 A1 | 3/2016 | Tsai et al. |

(56) References Cited

U.S. PATENT DOCUMENTS

| | | |
|---|---|---|
| 2016/0135862 A1 | 5/2016 | Shoshtaev |
| 2017/0035468 A1 | 2/2017 | McCormack et al. |
| 2017/0172586 A1 | 6/2017 | Wallace et al. |
| 2017/0200315 A1 | 7/2017 | Lockhart |
| 2017/0224325 A1 | 8/2017 | Liu et al. |
| 2018/0064461 A1 | 3/2018 | Tran et al. |
| 2018/0256021 A1 | 9/2018 | Gill |
| 2019/0008656 A1 | 1/2019 | Salvermoser et al. |
| 2019/0053814 A1 | 2/2019 | Hoogland |
| 2019/0105062 A1 | 4/2019 | Tally et al. |
| 2020/0121177 A1 | 4/2020 | Gibson et al. |
| 2020/0297374 A1 | 9/2020 | Tran et al. |
| 2020/0305949 A1 | 10/2020 | Ellman et al. |
| 2021/0059691 A1 | 3/2021 | Zille |
| 2021/0085359 A1 | 3/2021 | Gleason |
| 2021/0113252 A1 | 4/2021 | Ammerman et al. |
| 2021/0137537 A1 | 5/2021 | Zille |
| 2021/0137684 A1 | 5/2021 | Johnson et al. |
| 2021/0145490 A1 | 5/2021 | Butler et al. |
| 2021/0169532 A1 | 6/2021 | Field et al. |
| 2021/0186584 A1 | 6/2021 | Salvermoser et al. |
| 2021/0204986 A1 | 7/2021 | Smisson, III et al. |
| 2021/0212833 A1 | 7/2021 | Chin et al. |
| 2021/0322063 A1 | 10/2021 | Altarac et al. |
| 2021/0386434 A1 | 12/2021 | Tanaka et al. |
| 2022/0008058 A1 | 1/2022 | Seifert et al. |
| 2022/0031297 A1 | 2/2022 | McCormack et al. |
| 2022/0061894 A1 | 3/2022 | Altarac et al. |
| 2022/0071668 A1 | 3/2022 | Gephart et al. |
| 2022/0125444 A1 | 4/2022 | Frock et al. |
| 2022/0142679 A1 | 5/2022 | Frock et al. |
| 2022/0142709 A1 | 5/2022 | Zucker |
| 2022/0160375 A1 | 5/2022 | Chin et al. |
| 2022/0241015 A1 | 8/2022 | Zucker |
| 2022/0241091 A1 | 8/2022 | Greenhalgh et al. |
| 2022/0257387 A1 | 8/2022 | Greenhalgh et al. |
| 2022/0265258 A1 | 8/2022 | Choi et al. |
| 2022/0273283 A1 | 9/2022 | Reimels |
| 2022/0304818 A1 | 9/2022 | Northcutt et al. |
| 2022/0323117 A1 | 10/2022 | Phan et al. |
| 2022/0346822 A1 | 11/2022 | Tran et al. |
| 2022/0361807 A1 | 11/2022 | Benson |
| 2022/0370061 A1 | 11/2022 | Liu et al. |
| 2023/0012760 A1 | 1/2023 | Tatsumi |
| 2023/0039562 A1 | 2/2023 | Ellman et al. |
| 2023/0051745 A1 | 2/2023 | Pacheco-Serrant et al. |
| 2023/0121290 A1 | 4/2023 | Gleason et al. |
| 2023/0157689 A1 | 5/2023 | Predick |
| 2023/0157710 A1 | 5/2023 | Predick |
| 2023/0157711 A1 | 5/2023 | Predick |
| 2023/0210508 A1 | 7/2023 | Bryan |
| 2023/0225881 A1 | 7/2023 | Predick |
| 2023/0255672 A1 | 8/2023 | Greenhalgh et al. |
| 2023/0270436 A1 | 8/2023 | Mehl |
| 2023/0293313 A1 | 9/2023 | Kyle |
| 2023/0404561 A1 | 12/2023 | Dinh et al. |
| 2024/0032906 A1 | 2/2024 | Ponmudi et al. |
| 2024/0032974 A1 | 2/2024 | Tanaka et al. |
| 2024/0050240 A1 | 2/2024 | Greenhalgh et al. |
| 2024/0058045 A1 | 2/2024 | Lee et al. |
| 2024/0081874 A1 | 3/2024 | Garamszegi et al. |
| 2024/0099746 A1 | 3/2024 | McCormack et al. |
| 2024/0108373 A1 | 4/2024 | Ries et al. |
| 2024/0122629 A1 | 4/2024 | McCormack et al. |

FOREIGN PATENT DOCUMENTS

| | | |
|---|---|---|
| DE | 29703947 U1 | 6/1997 |
| DE | 10162933 B4 | 8/2008 |
| DE | 102011088252 A1 | 6/2013 |
| EP | 1778104 A1 | 5/2007 |
| EP | 2022414 A1 | 2/2009 |
| EP | 2810606 A1 | 12/2014 |
| EP | 2315550 B1 | 11/2015 |
| EP | 3035860 A1 | 6/2016 |
| EP | 3326556 A1 | 5/2018 |
| EP | 3412231 A1 | 12/2018 |
| EP | 4223241 A1 | 8/2023 |
| EP | 4312821 A1 | 2/2024 |
| FR | 2828088 A1 | 2/2003 |
| GB | 2177307 A | 1/1987 |
| GB | 2452678 A | 3/2009 |
| JP | 3884046 B2 | 2/2007 |
| JP | 2008-508058 A | 3/2008 |
| WO | 96/22056 A1 | 7/1996 |
| WO | 96/29936 A1 | 10/1996 |
| WO | 97/34536 A2 | 9/1997 |
| WO | 98/22022 A1 | 5/1998 |
| WO | 98/40015 A2 | 9/1998 |
| WO | 00/45868 A1 | 8/2000 |
| WO | 00/46868 A1 | 8/2000 |
| WO | 01/08571 A1 | 2/2001 |
| WO | 01/82998 A2 | 11/2001 |
| WO | 01/97721 A2 | 12/2001 |
| WO | 02/76311 A2 | 10/2002 |
| WO | 2004/052180 A2 | 6/2004 |
| WO | 2005/120401 A2 | 12/2005 |
| WO | 2006/015302 A1 | 2/2006 |
| WO | 2006/044727 A2 | 4/2006 |
| WO | 2007/016683 A2 | 2/2007 |
| WO | 2007/016686 A2 | 2/2007 |
| WO | 2007/085628 A1 | 8/2007 |
| WO | 2007/113808 A1 | 10/2007 |
| WO | 2007/134100 A2 | 11/2007 |
| WO | 2008/002900 A2 | 1/2008 |
| WO | 2008/042793 A2 | 4/2008 |
| WO | 2008/070867 A2 | 6/2008 |
| WO | 2008/100906 A2 | 8/2008 |
| WO | 2008/139260 A2 | 11/2008 |
| WO | 2009/036467 A1 | 3/2009 |
| WO | 2009/089090 A2 | 7/2009 |
| WO | 2009/152919 A1 | 12/2009 |
| WO | 2010/011348 A1 | 1/2010 |
| WO | 2015/113173 A1 | 8/2015 |
| WO | 2016/043711 A1 | 3/2016 |
| WO | 2017/089594 A1 | 6/2017 |
| WO | 2018/049078 A1 | 3/2018 |
| WO | 2020/018873 A1 | 1/2020 |
| WO | 2022/086808 A1 | 4/2022 |
| WO | 2022/207105 A1 | 10/2022 |
| WO | 2022/250191 A1 | 12/2022 |
| WO | 2023/148423 A1 | 8/2023 |
| WO | 2023/245144 A1 | 12/2023 |
| WO | 2024/081209 A1 | 4/2024 |
| WO | 2024/081280 A2 | 4/2024 |

OTHER PUBLICATIONS

Brown, L., "A Double-blind, Randomized, Prospective Study of Epidural Steroid Injection vs. The mild. RTM. , Procedure in Patients with Symptomatic Lumbar Spinal Stenosis" Pain Practice, 12(5):333-341 (2012).

Brunette, J. et al., "Comparative Rheology of Low- and Iso-Osmolarity Contrast Agents at Different Temperatures," Catherization and Cardiovascular Interventions, 71:78-83 (2008).

Chen, H. et al., "mild Procedure for Lumbar Decompression: A Review" Pain Practice, 13(2):146-153 (2013).

Chopko, B et al., "MiDAS I (mild.RTM. Decompression Alternative to Open Surgery): A Preliminary Report of a Prospective, Multi-Center Clinical Study" Pain Physician, 13:369-378 (2010).

Chopko, B., "A novel method for treatment of lumbar spinal stenosis in high-risk surgical candidates: pilot study experience with percutaneous remodeling of ligamenturn flavum and lamina" J. Neurosurg. Spine, 14:46-50 (2011).

Chopko, B., "Long-term Results of Percutaneous Lumbar Decompression for LSS: Two-Year Outcomes" Clinical Journal of Pain, [online]. Retrieved from: www.clinicalpain.com, Ahead-of-Print publication, doi: 10.1097/AJP.0b013e31827fb803, Feb. 26, 2013 (5 pages).

Deer, T. et al., "Minimally Invasive Lumbar Decompression for Spinal Stenosis" , JNR, 1(S1):29-32 (2011).

(56) References Cited

OTHER PUBLICATIONS

Deer, T. et al., "New Image-Guided Ultra-Minimally Invasive Lumbar Decompression Method: The mild. RTM. Procedure" Proceure Pain Physician, 13:35-41 (2010).

Deer, T. et al., "Study of Percutaneous Lumbar Decompression and Treatment Algorithm for Patients Suffering from Neurogenic Claudication" Pain Physician, 15:451-460 (2012).

Deer, T., "Minimally invasive lumbar decompression for the treatment of spinal stenosis of the lumbar spine" Pain Management, 2(5):457-465 (2012).

Fong, Sy et al. "Thoracic Myelopathy Secondary to Ligamentum Flavum Ossification," (Ann. Acad. Med. Singapore) 33:340-6 (2004).

Kashiwagi, K., "Histological Changes of the Lumbar Ligamentum Flavum with Age," (J. Jpn. Orthop. Assoc.) 67:221-229 (1993).

Levy, R. et al., "Systematic Safety Review and Meta-Analysis of Procedural Experience Using Percutaneous Access to Treat Symptomatic Lumbar Spina Stenosis" Pain Medicine, [online], http://onlinelibary.wiley.com/doi/10.1111/j.1526-4637.2012.01504.x, published online Nov. 8, 2012 (8 pages). Final publication in vol. 13, Issue 12, pp. 1554-1561, Dec. 2012.

Lingreen, R. et al., "Retrospective Review of Patient Self-Reported Improvement and Post-Procedure Findings for mild. RTM. (Minimally Invasive Lumbar Decompression)" Pain Physician, 13:555-560 (2010).

Mekhail, N, et al. "Functional and Patient Reported Outcomes in Symptomatic Lumbar Spinal Stenosis Following Percutaneous Decompression" Pain Practice, [online], http://onlinelibrary.wiley.com/doi/10.1111/j.1533-2500.2012.00565.x, published online Jun. 1, 2012 (9 pages). Final publication in vol. 12, Issue 6, pp. 417-425, Jul. 2012.

Mekhail, N. et al., "Long-Term Results of Percutaneous Lumbar Decompression mild. RTM. for Spinal Stenosis" Pain Practice, [online], http://onlinelibrary.wiley.com/doi/10.111/j.1533-2500.2011.00481.x, published online Jun. 16, 2011 (10 pages). Final publication in vol. 12, Issue 3, pp. 184-193, Mar. 2012.

Schomer, D. et al., "mild.RTM. Lumbar Decompression for the Treatment of Lumbar Spinal Stenosis" The Neuroradiclogy Journal, 24:620-626 (2011).

Wong, W., "mild Interlaminar Decompression for the Treatment of Lumbar Spinal Stenosis" Clinical Journal of Pain, 28 (6):534-538 (2012).

\* cited by examiner

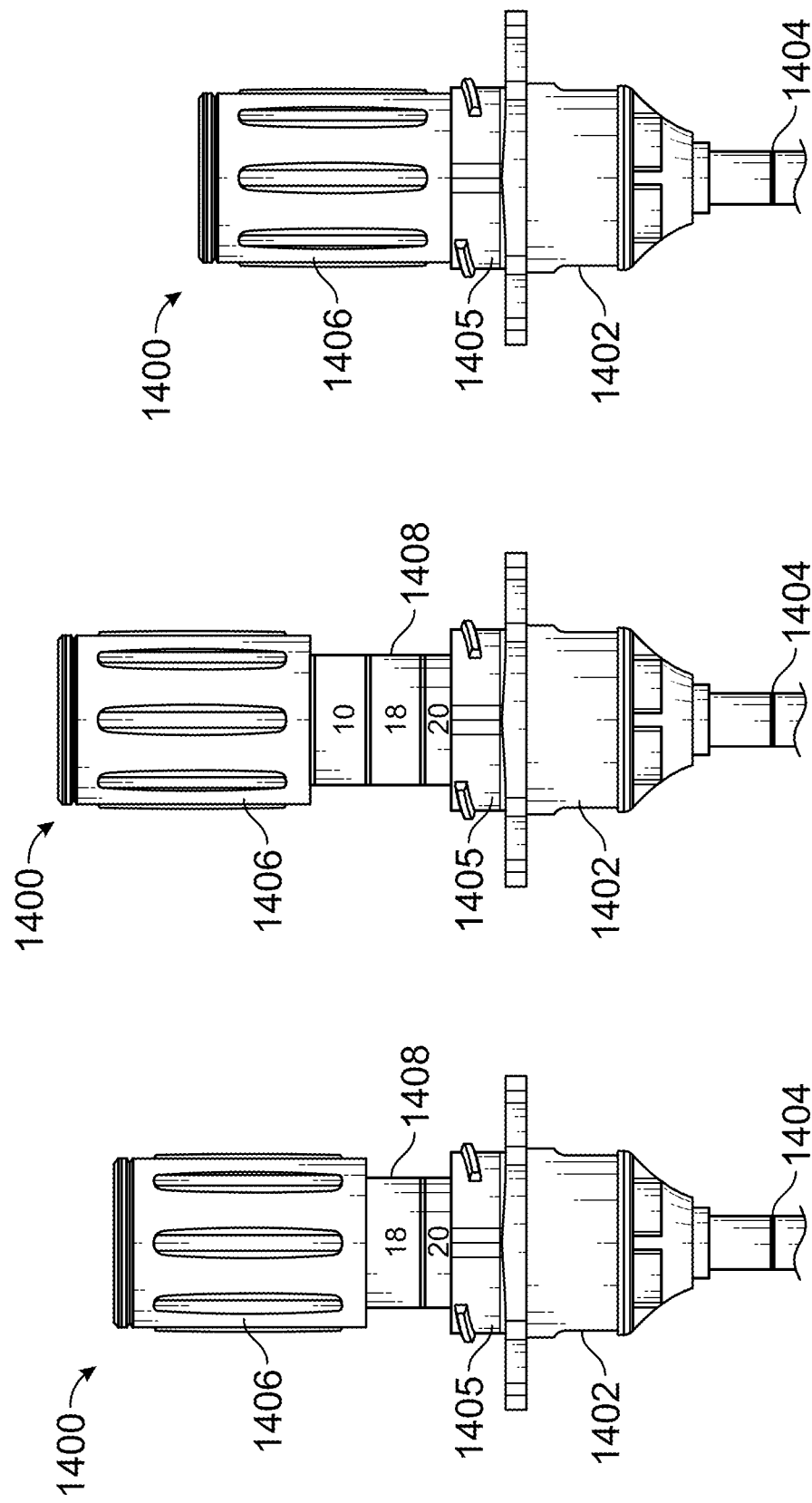

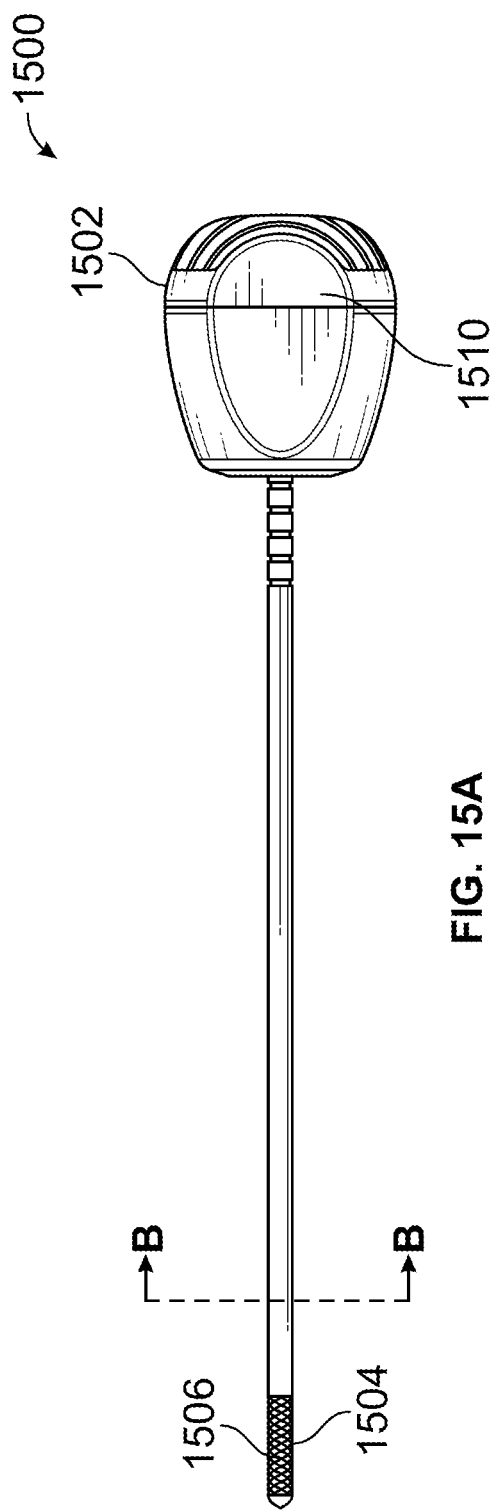
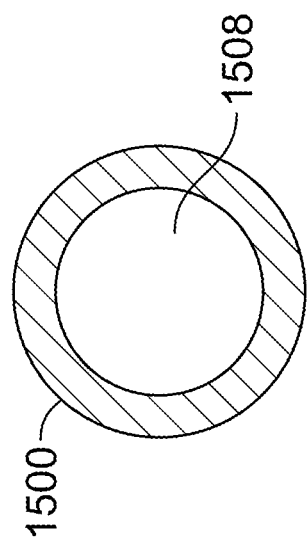
FIG. 15A
FIG. 15B

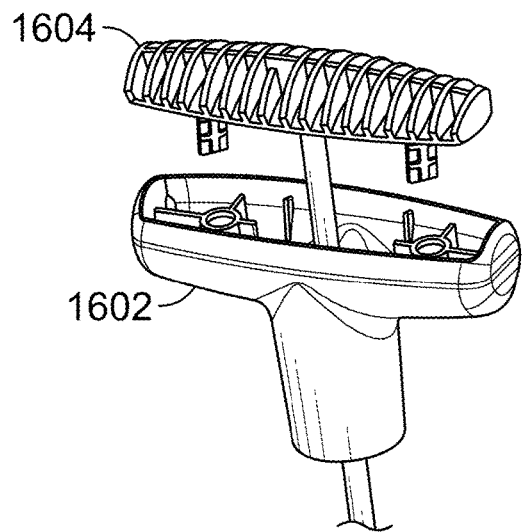
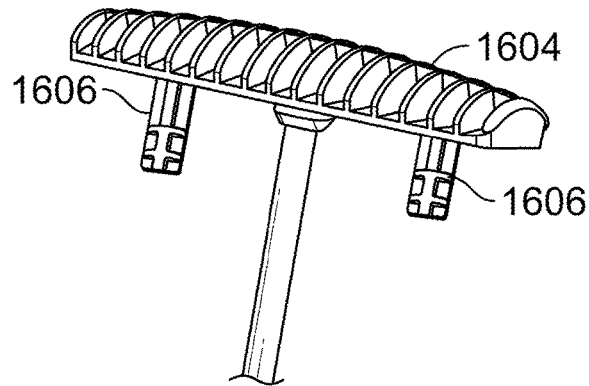
FIG. 16A  FIG. 16B
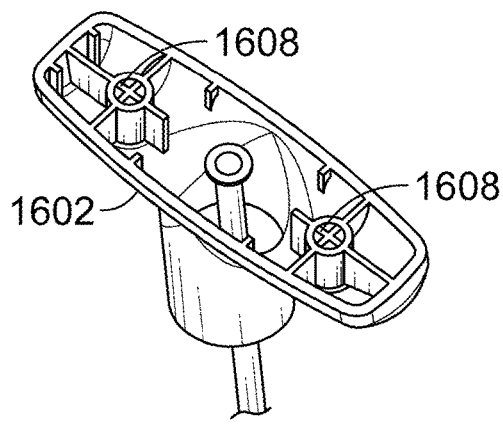
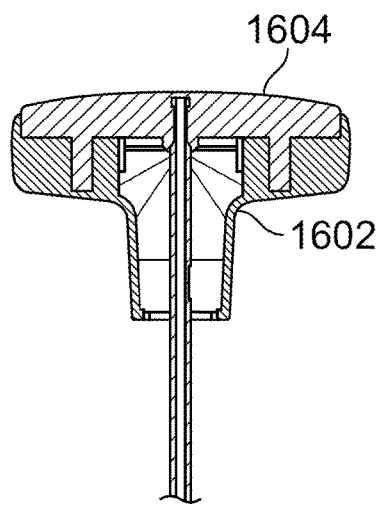
FIG. 16C  FIG. 16D

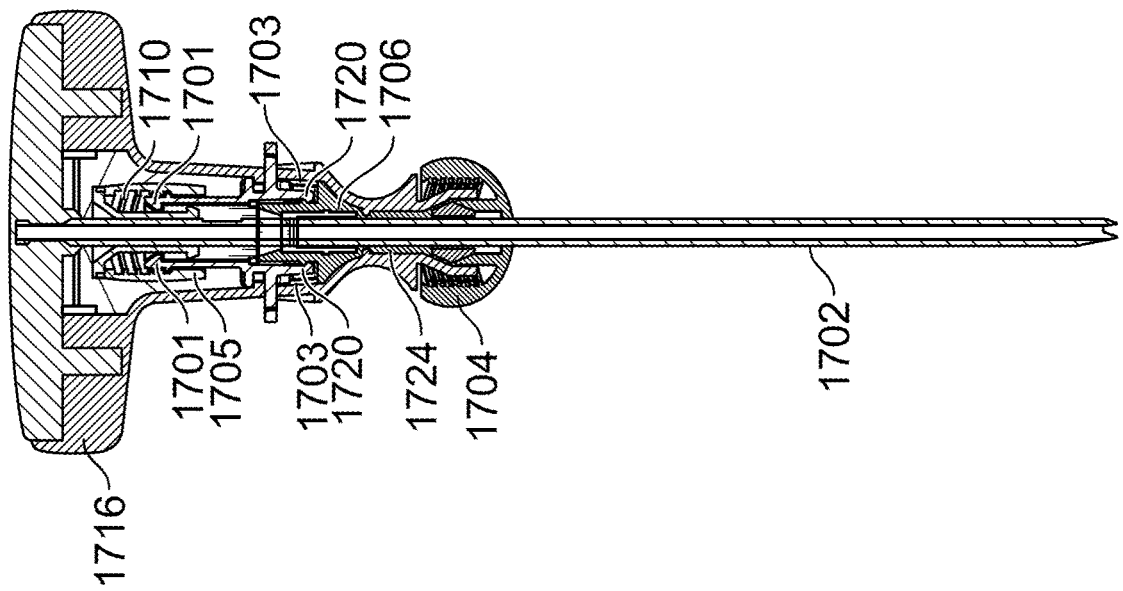
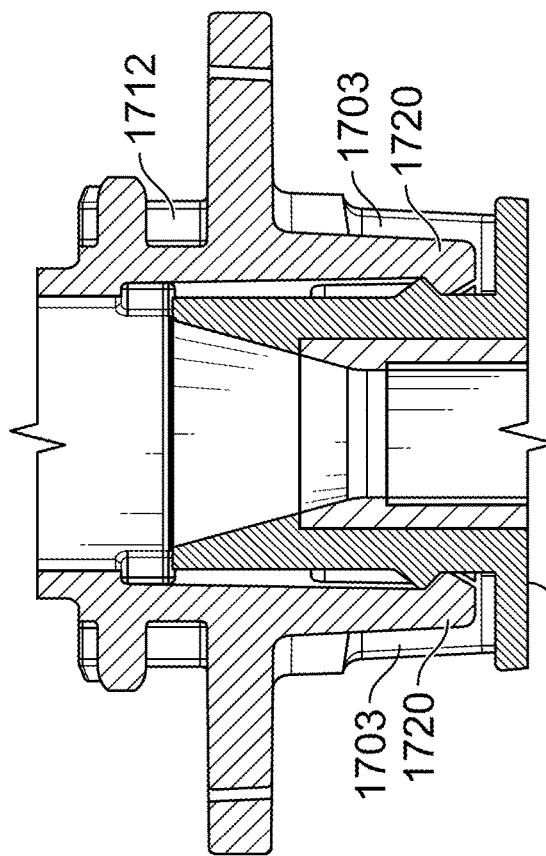
FIG. 17D
FIG. 17C

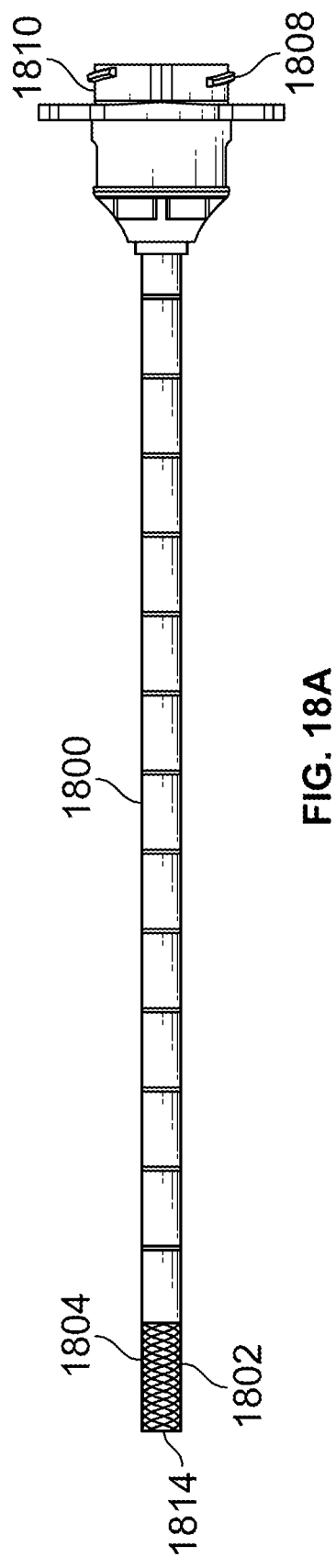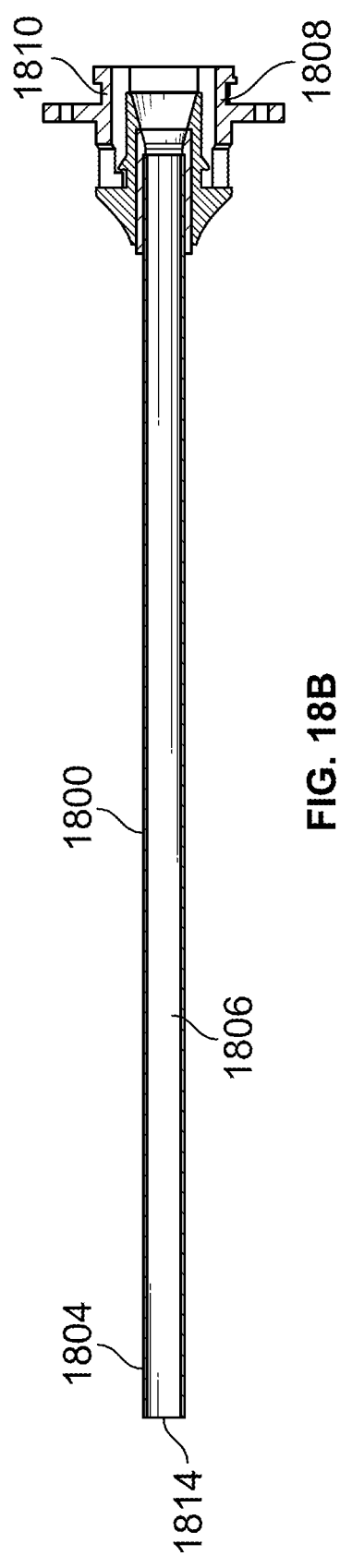

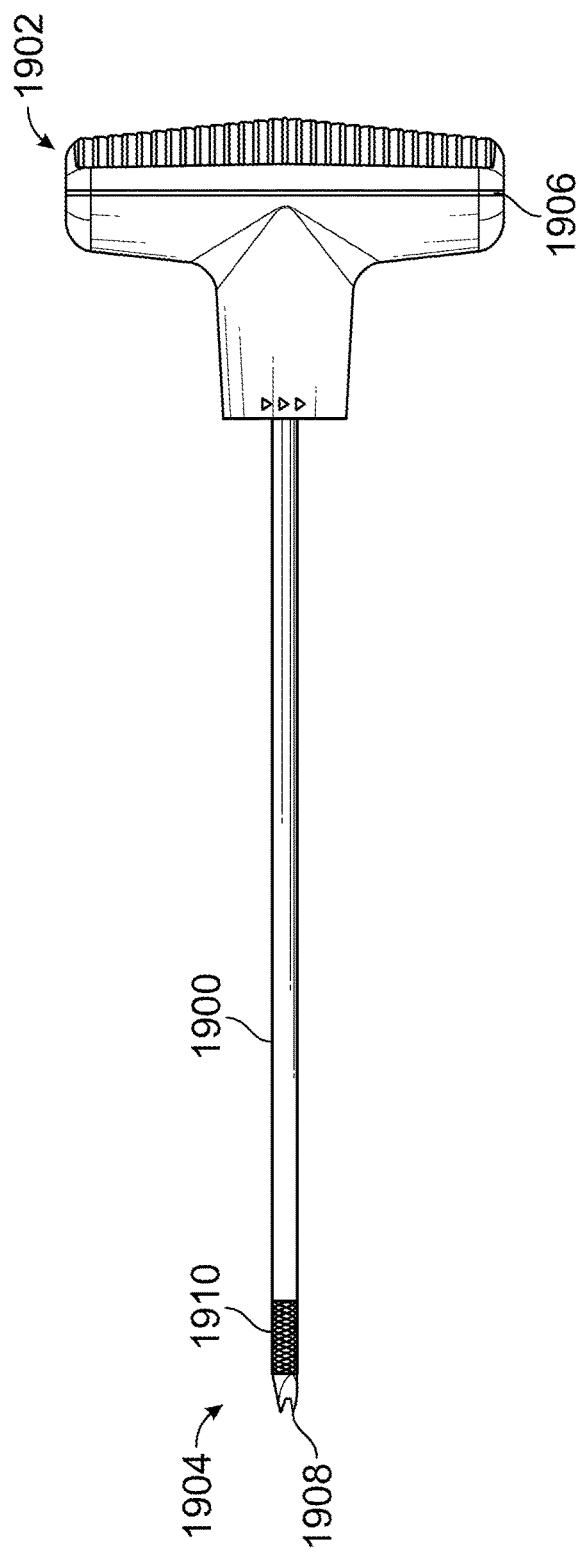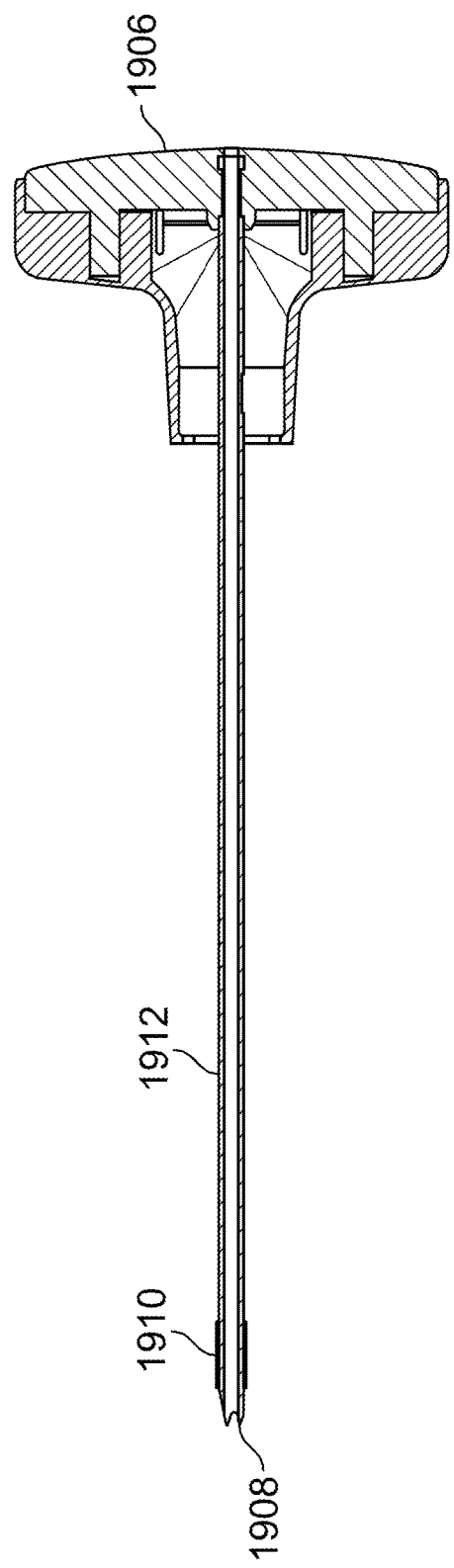
FIG. 19A
FIG. 19B

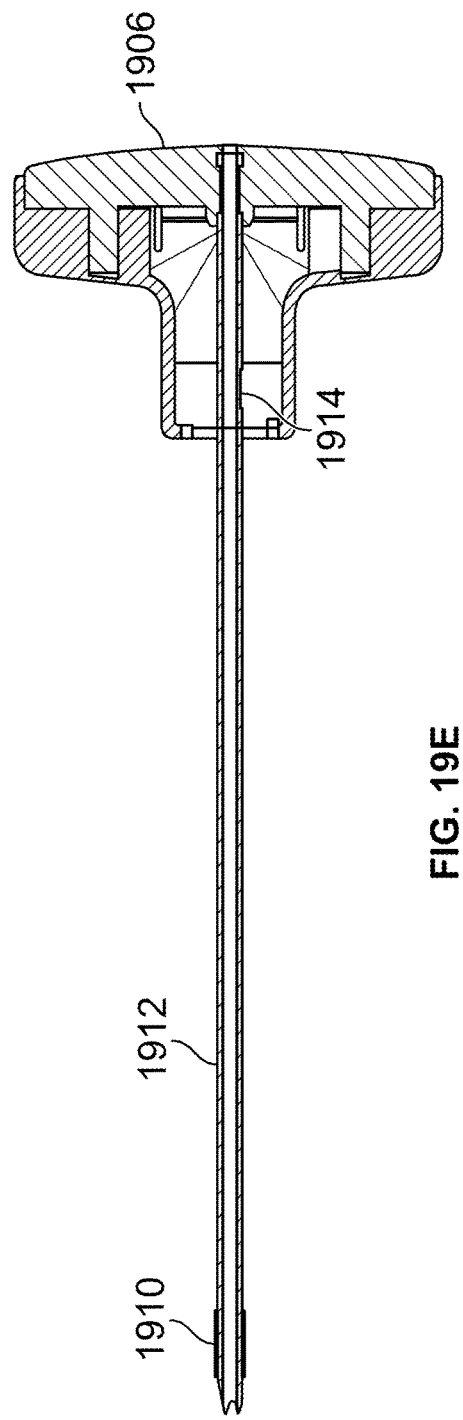
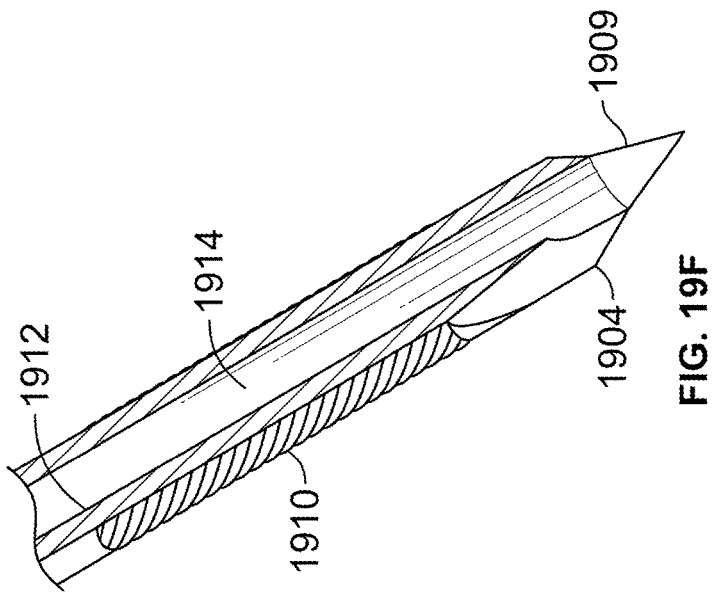
FIG. 19E
FIG. 19F

INTEGRATED INSTRUMENT ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example this application is a continuation of U.S. patent application Ser. No. 18/335,956, filed on Jun. 15, 2023, which claims priority to U.S. Provisional Application No. 63/352,997, filed on Jun. 16, 2022, each of which is hereby incorporated by reference in its entirety.

TECHNICAL FIELD

This application generally relates to minimally invasive systems for accessing and treating the spinal canal. The systems may include an integrated device that combines various instruments used for performing spinal procedures. Methods for treating spinal conditions, e.g., spinal stenosis, using the systems and integrated devices are also described herein.

BACKGROUND

Spinal stenosis is a condition that may occur when the spinal canal narrows to compress the spinal cord or associated nerves roots. The condition may have various etiologies. For example, spinal stenosis may be caused by spinal degeneration, which often occurs with aging, but may also be due to disc herniation, osteoporosis, cancerous growth, or a congenital condition. Spinal stenosis may also be caused by subluxation, facet joint hypertrophy, osteophyte formation, underdevelopment of the spinal canal, spondylosis deformans, degenerative intervertebral discs, degenerative spondylolisthesis, degenerative arthritis, ossification of the vertebral accessory ligaments, or thickening of the ligamentum flavum. A less common cause of spinal stenosis, which usually affects patients with morbid obesity or patients on oral corticosteroids, is excess fat in the epidural space. The excessive epidural fat compresses the dural sac, nerve roots and blood vessels contained therein, often resulting in back and leg pain, or weakness and numbness of the legs.

Spinal stenosis may affect the cervical, thoracic, or lumbar regions of the spine. In some cases, spinal stenosis may be present in all three regions. Lumbar spinal stenosis may cause lower back pain, abnormal sensations in the legs or buttocks, and loss of bladder or bowel control. Patients suffering from spinal stenosis may typically be treated first with exercise therapy, analgesics, or anti-inflammatory medications. If these conservative treatment options fail, surgery may be required to decompress the spinal cord or nerve roots.

Traditional surgical procedures to correct stenosis in the lumbar region generally require a large incision to be made in the patient's back. Muscles and other supporting structures are then stripped away from the spine, exposing the posterior aspect of the vertebral column. A portion of the vertebral arch, often at the laminae, may then be removed (laminectomy or laminotomy). The procedure is usually performed under general anesthesia. Patients may be admitted to the hospital for approximately five to seven days depending on the age and overall condition of the patient. Thereafter, patients often require between six weeks and three months to recover from the procedure. Further, many patients need extended therapy at a rehabilitation facility to regain enough mobility to live independently.

When spinal stenosis is due to compression of the intervertebral foramina, the passages between vertebrae through which nerves pass laterally from the spinal cord to the body become narrowed. Foramina compression is often due to unwanted bone, ligament, or scar tissue formation in the passages. A foraminotomy may relieve the symptoms of nerve compression caused by foramen constriction, but typically involve making an incision in the back of the patient's then peeling away muscle to reveal the bone underneath, and cutting a small hole in the vertebra. Through this hole, using an arthroscope, the foramen can be visualized, and the impinging bone or disk material removed. Much of the pain and disability after an open foraminotomy or laminectomy results from the tearing and cutting of the back muscles, blood vessels, supporting ligaments, and nerves. Also, because the spine stabilizing back muscles and ligaments are stripped and detached from the spine, these patients frequently develop spinal instability post-operatively.

Minimally invasive techniques, e.g., percutaneous techniques, generally offer the potential for less post-operative pain and faster recovery compared to traditional open surgery. For example, percutaneous spinal procedures may be performed with local anesthesia, thereby sparing the patient the risks and recovery time required with general anesthesia. In addition, there may be less damage to the paraspinal muscles and ligaments with minimally invasive techniques, thereby reducing pain and the damage caused to stabilizing structures.

Various techniques for minimally invasive treatment of the spine have been developed. For example, microdiscectomy is one technique that includes making a small incision in the skin and deep tissues to create a portal to the spine. A microscope is then used to aid in the dissection of the adjacent structures prior to discectomy. Although the recovery time for this procedure is much shorter than traditional open discectomies, the technique is not relevant in treating other spinal disorders such as spinal stenosis. Arthroscopy using an optical catheter has also been proposed to treat spinal stenosis. These devices and techniques are limited by the small size of the spinal canal, and thus the operations may be generally difficult to perform and master.

Accordingly, it would be useful to have other systems, devices, and methods for performing minimally invasive spinal procedures. It would also be beneficial to have systems and methods for percutaneously accessing the spinal canal and performing a spinal procedure in multiple locations along the canal, e.g., bilaterally and/or at multiple levels, from a single access point. Systems and devices that integrate the instruments for performing the procedures would also be useful since they would improve ease of use, reduce procedural complexity, and minimize procedure time.

SUMMARY

The systems and devices described herein may be generally used to percutaneously access the spinal canal and perform minimally invasive procedures on the canal and/or surrounding tissues. For example, the systems and devices may be used to perform lumbar decompressive procedures percutaneously. Instead of providing an instrument kit having multiple separate devices and/or system components (e.g., a stabilization component) that would require assembly prior to use, the systems may include an assembly that combines two or more of these devices and/or system components to improve ease of use, reduce procedural complexity, and minimize procedure time, as mentioned above. For example, one or more of a portal cannula, trocar, depth guide, bone auger, and stabilization component such as a portal grip may be removably coupled together (e.g., slidingly attached and/or attached via a snap-fit, interference fit, threaded connector, and/or other type of mechanical connector) to form an integrated assembly. As used herein, the terms "integrated assembly" and "integrated device" are used interchangeably.

The integrated assembly may include a portal grip slidably attached to the portal cannula. The portal grip may be configured to seat against the skin surface and lock at a position along the length of the portal cannula. When locked, the portal grip may prevent or provide resistance against further advancement of the portal cannula into the body. Once the target depth of the portal cannula is set, working instruments may be advanced through the portal cannula. Examples of working instruments may include bone augers, hand-operated mechanical biting instruments such as bone rongeurs, mechanical scooping devices such as tissue sculptors, power-operated mechanical instruments such as grinders and drills, and light guiding and/or visualization devices. Other examples of working instruments may include electric, magnetic, electromagnetic, vibration, sound, and kinetic energy delivering components such as RF probes, ultrasound probes, and energy delivering wires. In some instances, the working instrument may use streams of fluid to modify tissue. The portal grip may also function as a fulcrum point for the portal cannula.

In general, the systems for minimally invasive spine surgery described herein may include a portal cannula having a proximal end and an outer surface. A portal grip comprising a housing may be slidably attached to the portal cannula. The housing of the portal grip may include a lumen and a lock assembly configured to releasably secure the portal grip at one or more positions along a length of the portal cannula. Put another way, the portal grip may include a mechanism to mechanically engage with the outer surface of the cannula and/or other components of the integrated assembly to prevent or substantially reduce axial movement of the portal grip along the cannula. The mechanical engagement may be reversible to allow for adjustments, if needed.

The portal grip may be configured in various ways so that it may be releasably secured to the portal cannula. For example, at least a portion of the portal grip may be configured to rotate to releasably secure the portal grip to the portal cannula. In this instance, a portion of the housing may be spherically shaped. In other instances, the housing may include a first component coupled to a second component, where the first component may be configured to rotate with respect to the second component to releasably secure the portal grip at one or more positions along the length of the portal cannula. Coupling of the first component to the second component may be accomplished via a threaded connection.

The lock assembly contained within portal grip housing may also have various configurations. The lock assemblies may be generally configured for use with a single hand. Additionally, the lock assemblies may be configured to maintain the position of the portal grip along the length of the portal cannula upon exposure of the portal cannula to fatty lipids or a body fluid.

In some variations, the lock assembly may include a collet concentrically disposed about the portal cannula. The collet may be configured to compress against the outer surface of the portal cannula to prevent movement of the portal grip along the length of the portal cannula. Some variations of the collet may comprise a plurality of fingers spaced about a circumference of the collet. The plurality of fingers may include between two to six fingers. For example, the plurality of fingers may include two, three, four, five, or six fingers. In some variations, it may be beneficial for the collet to include three fingers or six fingers. The plurality of fingers may be symmetrically or asymmetrically spaced about the collet circumference.

Alternatively, the lock assembly may include a spiral cam. The spiral cam may be configured to tighten around the outer surface of the portal cannula to prevent movement of the portal grip along the length of the portal cannula. A toggle may be coupled to the spiral cam to aid in tightening the spiral cam around the outer surface of the portal cannula.

Locking of the portal grip to the portal cannula may also be accomplished using a portal grip housing configured to rotate into axial alignment with the portal cannula. In this variation, axial alignment of the housing with the portal cannula displaces a cam rider to releasably secure the portal grip at one or more positions along the length of the portal cannula.

Instead of providing an instrument kit having multiple separate devices, the systems described herein may include an assembly that integrates one or more kit components. The kit components may be removably coupled together, for example, by being slidingly attached and/or attached via a snap-fit, interference fit, threaded connector, and/or other type of mechanical connector. The kit components may also be removably coupled together, for example, by magnetic or adhesive forces. For example, the portal cannula may be removably coupled to one or more system components. The one or more system components may include a trocar having a handle. In some variations, the proximal end of the portal cannula may include a hub having at least one fin configured to limit advancement of the trocar when the trocar is releasably coupled to the portal cannula. In other variations, the hub may be enlarged such that it limits advancement of the trocar when the trocar is releasably coupled to the portal cannula.

The one or more system components may also include a depth guide having a proximal end and a distal end. The depth guide distal end may be removably coupled to the hub of the portal cannula by a tab locking feature, and the trocar handle removably coupled to the hub by a threaded connection. Rotation of a knob on the depth guide may provide feedback on the insertion depth for a working instrument.

In some variations, the systems comprising an integrated instrument assembly include a portal cannula having a proximal end, a portal grip slidably attached to the portal cannula and comprising a housing, where the portal grip comprises a lock assembly configured to releasably secure the portal grip at one or more positions along a length of the portal cannula. The integrated assembly may also include a trocar removably coupled to the portal cannula and a depth guide removably coupled to the portal cannula. The proximal end of the portal cannula may include a hub configured to limit advancement of the trocar when the trocar is releasably coupled to the portal cannula. Additionally, the depth guide may provide tactile feedback when configuring an insertion depth for one or more working instruments and/or other instruments.

Access devices for minimally invasive procedures or surgeries that include a collet as part of the locking assembly are also described herein. These access devices may include a portal cannula and a portal grip housing, which may contain the collet. The portal grip may be slidably attached to the portal cannula. As previously described, the collet may be concentrically disposed about a portal grip lumen within the housing, and have an unlocked configuration and a locked configuration. In the locked configuration, the collet may secure the portal grip at one or more positions along a length of the portal cannula. The collet may transition from the unlocked to the locked configuration by compression of the collet against an outer surface of the portal cannula. The collet may include a plurality of fingers spaced about a circumference of the collet. The plurality of fingers may include between two to six fingers. For example, the plurality of fingers may include two, three, four, five, or six fingers. In some variations, it may be beneficial for the collet to include three fingers or six fingers. There may be some instances where more than six fingers are employed. The plurality of fingers may be symmetrically or asymmetrically spaced about the collet circumference.

Methods for accessing a spinal region in a patient are also described herein. The methods may generally include percutaneously introducing a portal cannula into the spinal region, where the portal cannula comprises a distal tip and a portal grip slidingly attached thereto, and advancing the portal cannula distal tip to a target depth in the spinal region. Once at the target depth, the method may further include sliding the portal grip along the portal cannula to contact a skin surface of the patient, and locking the portal grip at a position on the cannula thereby bracing the portal cannula distal tip at the target depth. The locked position of the portal grip may be maintained along the length of the portal cannula upon exposure to fatty lipids or a body fluid, which may increase the lubricity of the portal cannula surface. When the portal cannula is introduced, a trocar may be disposed within the portal cannula and used to assist with accessing the spinal region. Once at the target depth, the trocar may be removed to allow advancement of working instruments through the portal cannula.

The portal grip may include a housing, and rotation of at least a portion of the housing may lock the position of the portal grip on the cannula. When a portion of the housing is spherically shaped, it may comprise a first component coupled to a second component. In this instance, locking the portal grip may include rotating the first component with respect to the second component. In other instances, locking the portal grip may include rotating the housing into axial alignment with the portal cannula.

When the portal grip includes a locking assembly, the locking assembly may comprise a collet concentrically disposed about the portal cannula, and locking the portal grip may include compressing the collet against an outer surface of the portal cannula. Instead of a collet, the locking assembly may include a spiral cam that generally effects locking of the portal grip by tightening of the spiral cam around the outer surface of the portal cannula.

The methods described herein may further include unlocking the portal grip from the portal cannula. Unlocking may be achieved in various ways. For example, unlocking may be accomplished by rotating at least a portion of the housing or by rotating the housing out of axial alignment with the portal cannula. Once unlocked, the portal grip may be slidingly advanced or retracted to a second position along the portal cannula, and then locked to the portal cannula at the second position. Locking and unlocking the portal grip position may be accomplished using a single hand.

In some variations, the methods may include removably coupling the portal cannula to one or more system components. The one or more system components may be a trocar, portal grip, or a depth guide. When a depth guide is employed, the method may include receiving feedback, e.g., tactile feedback, when ascertaining an insertion depth using the depth guide. Coupling of the portal cannula to the one or more system components may be achieved in various ways. For example, the proximal end of the portal cannula may be releasably coupled to the trocar by a threaded hub. In some instances, the proximal end of the portal cannula may be releasably coupled to the trocar by one or more magnets. Additionally or alternatively, the hub may include an outer ring that limits advancement of the trocar.

The methods may be used to perform various spinal procedures. For example, the methods may be used to remove a portion of a ligamentum flavum of the patient and/or other hard and/or soft tissues exerting pressure on nerves, to treat spinal stenosis, and/or to perform a laminectomy. Once percutaneous access to a spinal region is obtained with the systems described herein, instruments may be advanced through a lumen of the portal cannula to perform the procedure. For example, a bone auger, bone rongeur, and/or a tissue sculptor may be deployed through the lumen. The methods may further include percutaneously accessing the spinal canal and performing a spinal procedure in multiple locations along the canal, e.g., bilaterally and/or at multiple levels, from a single access point.

BRIEF DESCRIPTION OF THE DRAWINGS

FIG. 1A shows a perspective view of the integrated device. FIG. 1B shows an assembly view of the integrated device.

FIGS. 2A-4B depict exemplary portal cannulas including a hubs at their proximal ends having various configurations. FIGS. 2A and 2B show a side view and end view, respectively, of a hub having a hexagonal cross-sectional shape. In FIGS. 4A and 4B, side and end views, respectively, of a hub having a circular cross-sectional shape and flanges are shown that help limit further travel (e.g., advancement) of a trocar.

In FIG. 5A, a perspective view of the portal grip mounted on the portal cannula is provided. In FIG. 5B, the portal grip is shown slid down to contact the skin surface.

FIG. 6A shows a perspective view of the lock assembly, while FIGS. 6B and 6C provide side, cross-sectional views.

FIG. 7A provides a perspective view of the lock assembly, and FIG. 7B shows a top view of the assembly.

FIGS. 8A and 8B show side and cross-sectional views of the split spiral cam, respectively. In FIGS. 8C and 8D, cross-sectional views of the portal grip including the split spiral cam illustrate how rotation of the portal grip tightens the cam around the portal cannula.

FIGS. 10A and 10B generally illustrate the locking mechanism. In FIGS. 10C and 10D, cross-sectional views of the locking assembly within the portal grip housing are shown.

FIGS. 14A-14C depict an exemplary variation of a depth guide.

FIGS. 15A and 15B depict another exemplary variation of an integrated device comprising a bone auger. FIG. 15A shows a side view of the integrated device, and FIG. 15B provides a cross-sectional view taken along line B-B in FIG. 15A to show that the bone auger includes a lumen for passage of working instruments.

FIG. 15C shows an assembly view of the handle parts; FIG. 15D shows a perspective view of the insert of the handle; FIG. 15E shows an interior view of the handle housing; and FIG. 15F shows a cross-sectional view of the insert connected to the handle housing.

FIGS. 16A to 16D depict various views of an exemplary trocar handle including a housing and an insert. FIG. 16A shows an assembly view of the handle parts; FIG. 16B shows a perspective view of the insert of the handle; FIG. 16C shows an interior view of the handle housing; and FIG. 16D shows a cross-sectional view of the insert connected to the handle housing.

FIGS. 17A-17D depict another exemplary integrated device comprising a portal cannula, a portal grip, and a trocar. FIG. 17A shows a perspective view of the integrated device; FIG. 17B shows an assembly view of the integrated device; FIG. 17C shows an exemplary connector for attaching the depth guide to the portal cannula hub; and FIG. 17D shows a cross-sectional view of the integrated device in FIG. 17A.

FIGS. 18A-18D depict an exemplary device comprising a portal cannula that may also be used as a bone auger. FIG. 18A shows a side, perspective view of the device; FIG. 18B shows a cross-sectional view of the device; FIG. 18C shows an enlarged view of the teeth at the distal tip of the device; and FIG. 18D shows a trocar disposed within the lumen of the portal cannula.

FIGS. 19A-19H depict views of an exemplary device comprising a trocar that may also be used as a bone auger.

DETAILED DESCRIPTION

Described herein are systems and devices that may be used to percutaneously access the spinal canal and perform minimally invasive procedures on the canal and/or surrounding tissues. The systems may include an assembly that integrates two or more devices of a surgical instrument kit into a single assembly to improve ease of use, reduce procedural complexity, and minimize procedure time, as mentioned above. In some variations, the integrated assembly combines two or more devices or system components used to access a spinal region. For example, one or more of a portal cannula, trocar, depth guide, and stabilization component (e.g., a portal grip) may be removably coupled together (e.g., slidingly attached and/or attached via a snap-fit, interference fit, threaded connector, magnetic and/or other type of mechanical connector) to form the integrated assembly. The stabilization component (e.g., the portal grip) may be configured to provide a fulcrum point for the portal cannula as well prevent or provide resistance against further advancement of the portal cannula into the body. Once the target depth of the portal cannula is set, working instruments such as a bone auger, bone rongeur, tissue sculptor, etc., may be advanced through the portal cannula.

Systems

Figure 1A:
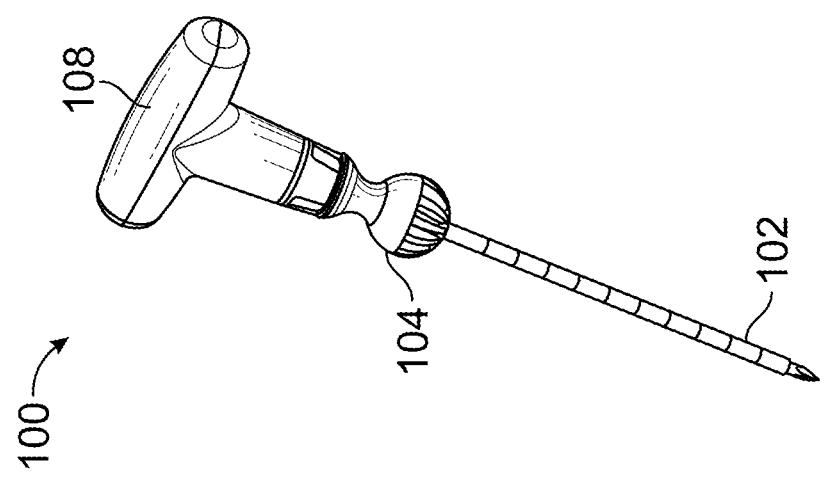
FIGS. 1A and 1B depict an exemplary integrated device comprising a portal cannula, a portal grip, and a trocar.
Figure 1B:
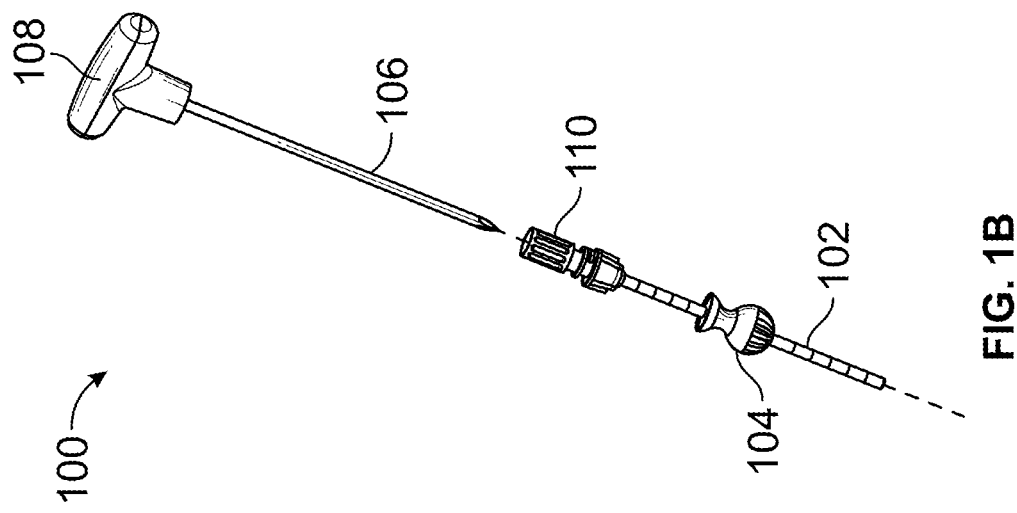
Figure 2B:
Figure 3B:
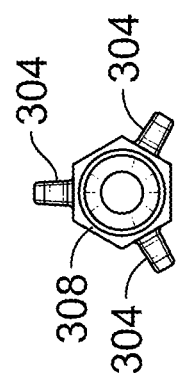
FIGS. 3A and 3B show a side view and end view, respectively, of a hub having a plurality of fins.

In general, the systems for minimally invasive spine surgery described herein may include an integrated device used to percutaneously access a spinal region. The integrated device may include a portal cannula having a proximal end, a distal end, and an outer surface. Additionally, the integrated device may include a stabilization component, such as a portal grip, comprising a housing that may be slidably attached to the portal cannula. The housing of the portal grip may include a lumen and a lock assembly configured to releasably secure the portal grip at one or more positions along a length of the portal cannula. The integrated device may further include a trocar and a depth guide. For example, referring to FIGS. 1A and 1B, the system may generally comprise an integrated device (100) that may include a portal cannula (102), a portal grip (104), a trocar (106) having a handle (108), and a depth guide (110). FIG. 1A shows a perspective view of the integrated device (100). In FIG. 1B, an assembly view of the integrated device (100) is provided to show the portion of the trocar (106) disposed within the portal cannula (102) and the depth guide (110), which may be at least partially disposed within the trocar handle (108).

Portal Cannula

The portal cannula may be the conduit through which working instruments, e.g., a bone auger, bone rongeur, or tissue sculptor, may be advanced to perform a spinal procedure. The portal cannula may also be the conduit within which the trocar is slidingly disposed when percutaneously accessing the spinal region, as shown in FIGS. 1A and 1B. The portal cannula may have a proximal end, a distal end, and an outer surface. A lumen may extend within the portal cannula from the proximal end to the distal end. Additionally, the portal cannula may create a single access point via which working instruments may be advanced to perform spinal procedures, e.g., lumbar decompression. In some variations, lumbar decompression and other spinal procedures may be performed unilaterally, bilaterally, and/or at multiple levels through the single access point.

The portal cannula may be made from stainless steel, nitinol, or alloys thereof. In some variations, the portal cannula may comprise a hypotube. A coating may be placed on the outer cannula surface to provide anti-fouling and/or antimicrobial properties to the cannula. The coatings may generally comprise a polymeric material. Exemplary polymeric materials may include without limitation, hydrophilic polymers, hydrophobic polymers, and mixtures of these two types of polymers.

The working length of the portal cannula may vary depending on such factors as the particular spinal procedure being performed, the size of the patient, and/or patient age, and may range from about 6 cm to about 20 cm, including all values and sub-ranges therein. For example, the working portal cannula length may be about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, or about 20 cm. When additional length is needed, the working portal cannula length may range from about 21 cm to about 35 cm, including all values and sub-ranges therein. For example, the working portal cannula length may be about 21 cm, about 22 cm, about 23 cm, about 24 cm, about 25 cm, about 26 cm, about 27 cm, about 28 cm, about 29 cm, about 30 cm, about 31 cm, about 32 cm, about 33 cm, about 34 cm, or about 35 cm. Accordingly, the portal cannula may have an overall length ranging from about 6 cm to about 35 cm, including all values and sub-ranges therein. For example, the overall portal cannula length may be about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, about 25 cm, about 26 cm, about 27 cm, about 28 cm, about 29 cm, about 30 cm, about 31 cm, about 32 cm, about 33 cm, about 34 cm, or about 35 cm.

Similarly, the outside diameter (OD) and inside diameter (ID) of the portal cannula may vary depending on such factors as the particular spinal procedure being performed, the size of the patient, and/or patient age. The portal cannula may have an OD ranging from about 1.0 mm to about 30 mm, and an ID ranging from about 0.5 mm to about 29.5 mm, including all values and sub-ranges therein. For example, the OD may be about 1.0 mm, about 1.5 mm, about 2.0 mm, about 2.5 mm, about 3.0 mm, about 3.5 mm, about 4.0 mm, about 4.5 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 7.0 mm, about 8.0 mm, about 9.0 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, or about 30 mm. The ID may be about 0.5 mm, about 1.0 mm, about 1.5 mm, about 2.0 mm, about 2.5 mm, about 3.0 mm, about 3.5 mm, about 4.0 mm, about 4.1 mm, about 4.2 mm, about 4.3 mm, about 4.4 mm, about 4.5 mm, about 4.6 mm, about 4.7 mm, about 4.8 mm, about 4.9 mm, about 5.0 mm, about 5.5 mm, about 6.0 mm, about 6.5 mm, about 7.0 mm, about 7.5 mm, about 8.0 mm, about 8.5 mm, about 9.0 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, about 20 mm, about 20.5 mm, about 21 mm, about 21.5 mm, about 22 mm, about 22.5 mm, about 23 mm, about 23.5 mm, about 24 mm, about 24.5 mm, about 25 mm, about 25.5 mm, about 26 mm, about 26.5 mm, about 27 mm, about 27.5 mm, about 28 mm, about 28.5 mm, about 29 mm, or about 29.5 mm. In one variation, the OD may be about 5.2 mm (0.203 inches), and the ID may be about 4.7 mm (0.184 inches).

A hub may be coupled or fixed to the proximal end of the portal cannula by any suitable method, for example, using a friction fit or an adhesive. In some variations, the hub may be over-molded onto the proximal end of the cannula. The hub may be made from various polymeric or metallic materials. Exemplary polymeric materials may include without limitation, Acrylonitrile butadiene styrene (ABS) Polycarbonate, or ABS/Polycarbonate blends. Non-limiting examples of metals that the hub may be made from include stainless steel, nitinol, and alloys thereof.

The hub may include one or more features configured to limit travel of the trocar with respect to the portal cannula. The travel limit may be a useful safety feature in cases in which the depth guide is removed to increase the working length of the instruments (e.g., when the surgeon treats multiple spinal levels) and the depth guide is not reattached before inserting the trocar to treat the next level. In this instance the hub may limit advancement of the trocar so that its penetrating tip does not injure non-target anatomy.

For example, the size and/or shape of the hub may provide a surface against which the handle of the trocar may contact to prevent further advancement of the trocar through the portal cannula. In these instances, the diameter of at least a portion of the hub may be larger than the diameter of the distal portion of the trocar handle to create an interference fit with the trocar handle such that travel of the trocar is limited.

In addition to having a larger diameter than the distal portion of the trocar handle, the hub may be variously shaped. For example, the cross-sectional shape of the hub may be a circle, hexagon, or square. In some variations, the hub may include a body and a plurality of fins that extend radially outwardly from the body to limit travel of the trocar. The number of fins may range from two to six. For example, the hub may include two, three, four, five, or six fins. In some variations, more than six fins may be included. The plurality of fins may also be variously angled with respect to the hub body. Each of the plurality of fins may have the same angle with respect to the hub body, or one or more of the fins may have a different angle than one or more other of the fins. Furthermore, the plurality of fins may be symmetrically or asymmetrically spaced about the hub body. Each of the plurality of fins may also have any length suitable to create an interference fit with the trocar handle such that travel of the trocar is limited, and each of the plurality of fins may have the same or different lengths.

Figure 4B:
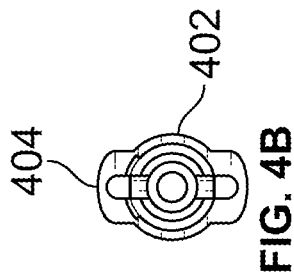
Figure 2A:
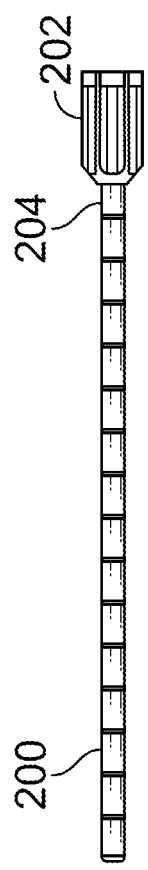
Figure 3A:
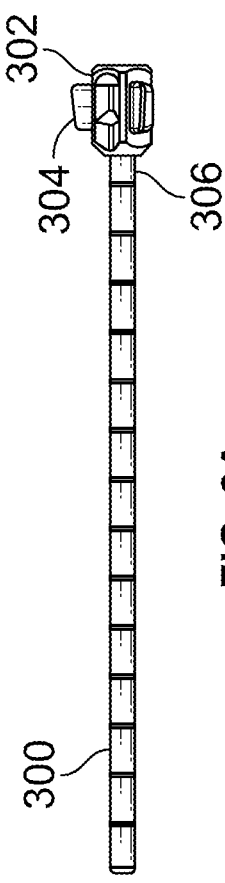
Figure 4A:
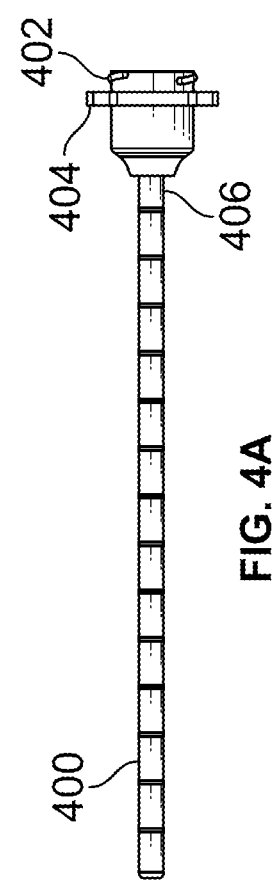

Referring to FIGS. 2A-4B, exemplary portal cannulas are shown including hubs at their proximal ends having various configurations. The hubs may include a body and one or more additional structures configured to limit travel of the trocar. In FIG. 2A, the portal cannula comprises a cannula (200) and a hub (202) coupled to a proximal end (204) of the cannula (202) having a hexagonal cross-sectional shape. The hexagonal cross-sectional shape is better shown in the end view provided in FIG. 2B. Alternatively, as shown in FIGS. 3A and 3B, the hub (302) at the proximal end (306) of the cannula (300) may have a base (308) from which a plurality of fins (304) outwardly extend. Although the base (308) is shown as having a hexagonal shape, it is understood that other shapes may be used. Similarly, although the base (308) is shown as having three fins (304), any suitable number of fins may be employed. In a further variation, as shown in FIGS. 4A and 4B, the hub (402) at the proximal end (406) of the cannula (400) may have a circular cross-sectional shape. A ring (404) that extends circumferentially about the circular hub (402) may function as a stop that limits further travel (e.g., advancement) of the trocar.

Portal Grip

The portal grip may be configured to hold the portal cannula and may be slidably attached thereto. In use, the portal grip may be slid along the length of the portal cannula to a position that seats it against the skin surface and provides a target cannula length within the body. The portal grip may be locked at this position to prevent or provide resistance against further advancement of the portal cannula into the body. Once the target depth of the portal cannula is set, working instruments such as the bone auger, bone rongeur, tissue sculptor, etc., may be advanced through the portal cannula.

The portal grip may also function as a fulcrum point for the portal cannula, and thus may be configured for smooth manipulation, e.g., rotation, against the skin surface when moving the working instrument to position it between the lamina. Accordingly, some variations of the portal grip may be configured to include a housing having at least a portion that is spherically shaped so that the portal grip is atraumatic during pivoting or other movement against skin. In housings having other shapes, e.g., square or rectangular shapes, the corners may be radiused so that damage to the skin surface is prevented. The housing of the portal grip may also include a lumen and a lock assembly configured to releasably secure the portal grip at one or more positions along a length of the portal cannula.

When the housing of the portal grip has at least a portion that is spherically shaped, the housing may comprise a ball structure having a waist region. The ball structure may include a first component coupled to a second component comprising the waist region. The waist region may include a midsection having a smaller diameter than both ends thereof, giving the waist region an hour-glass profile. A proximal end of the waist region may be configured to couple to the depth guide. The hourglass shape of the waist region may accommodate various hand positions, and may provide a pinky finger rest for comfort as well as allow thumb and forefinger access to the depth guide when working instruments are used. Additionally, the smaller diameter portion of the waist region may help secure the position of the portal grip along the portal cannula.

The hemispheres of the ball structure may have a diameter ranging from about 0.1 cm to about 10 cm, including all values and sub-ranges therein. For example, the ball structure diameter may be about 0.1 cm, about 0.5 cm, about 1.0 cm, about 1.5 cm, about 2.0 cm, about 2.5 cm, about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm. In some variations, e.g., when the portal cannula has a larger diameter, the diameter of the ball structure may be greater than 10 cm. As mentioned above, the waist region of the ball structure may include a midsection having a smaller diameter than both of its ends. The ends of the waist region may have a diameter that matches the ball structure, and thus may range from about 1.0 cm to about 10 cm, including all values and sub-ranges therein. For example, the end diameters may be about 1.0 cm, about 1.5 cm, about 2.0 cm, about 2.5 cm, about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm. In some instances, the diameter of one or both ends of the waist region may be smaller than that of the ball structure. The midsection of the waist region may have a diameter that is smaller, for example, about half the diameter of the ball structure, ranging from about 0.5 cm to about 5.0 cm, including all values and sub-ranges therein. For example, the diameter of the midsection may be about 0.5 cm, about 1.0 cm, about 1.5 cm, about 2.0 cm, about 2.5 cm, about 3.0 cm, about 3.5 cm, about 4.0 cm, about 4.5 cm, or about 5.0 cm.

The components of the portal grip may be made from the same material or different materials. For example, in some variations, the components of the portal grip may be made from otherwise comprise a polymer and/or a metal. Exemplary polymers include without limitation, acrylonitrile butadiene styrene (ABS), polycarbonate, polycarbonate/ABS blends, and copolymers thereof. If a metal is employed, the metal may be, for example, stainless steel, nitinol, and alloys thereof.

The portal grip may be configured in various ways so that it may be releasably secured to the portal cannula. For example, at least a portion of the portal grip may be configured to rotate to releasably secure the portal grip to the portal cannula. In this instance, a housing having a partially spherical shape may be useful. The housing may include a first component coupled to a second component, where the first component may be configured to rotate with respect to the second component to releasably secure the portal grip at one or more positions along the length of the portal cannula. Coupling of the first component to the second component may be accomplished via, for example, a threaded connection.

Figure 5A:
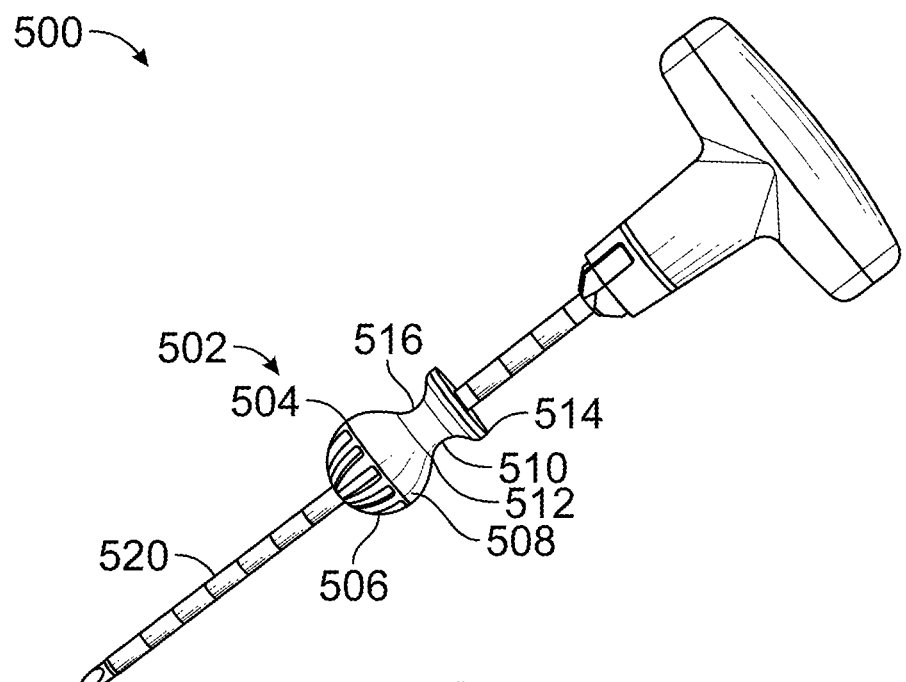
FIGS. 5A and 5B depict an exemplary variation of a portal grip.
Figure 5B:
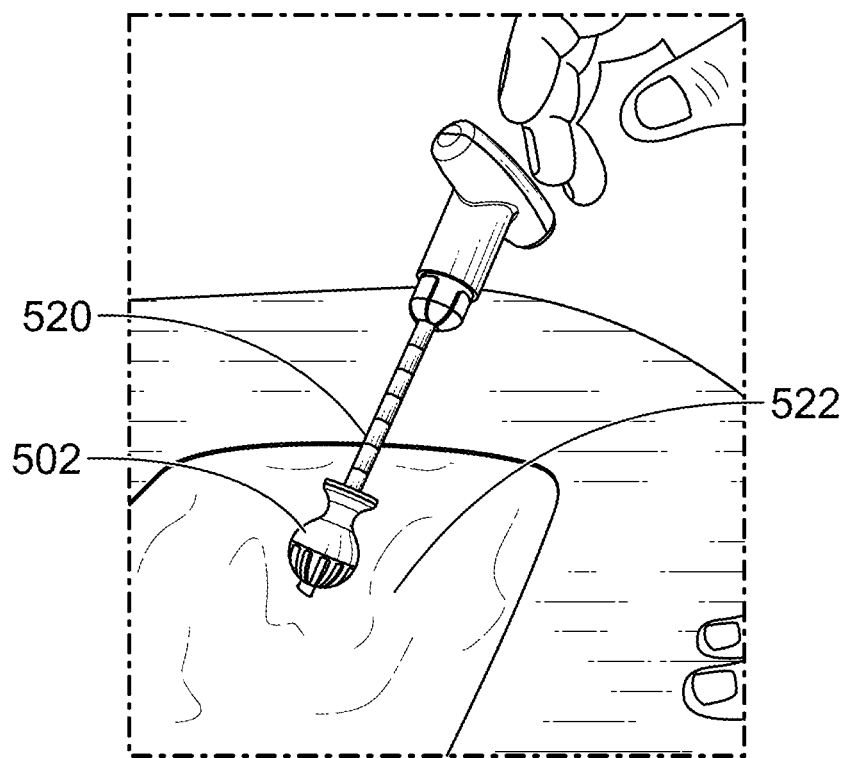
Figure 5C:
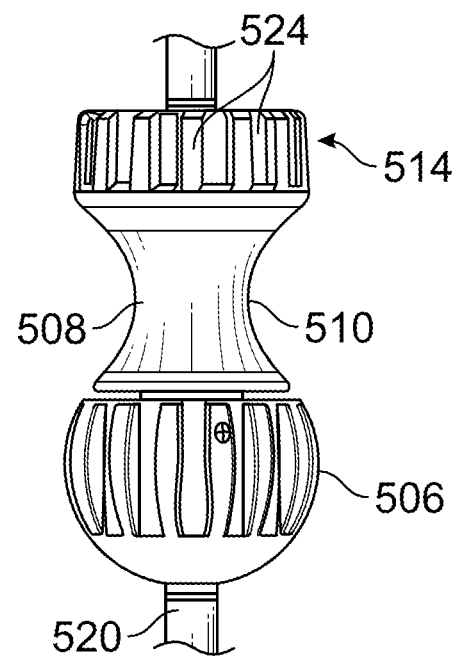
FIGS. 5C and 5D depict the portal grip of FIGS. 5A and 5B including a plurality of exemplary surface features that may help a user grip and rotate a second component of the portal grip with respect to a first component.
Figure 5D:
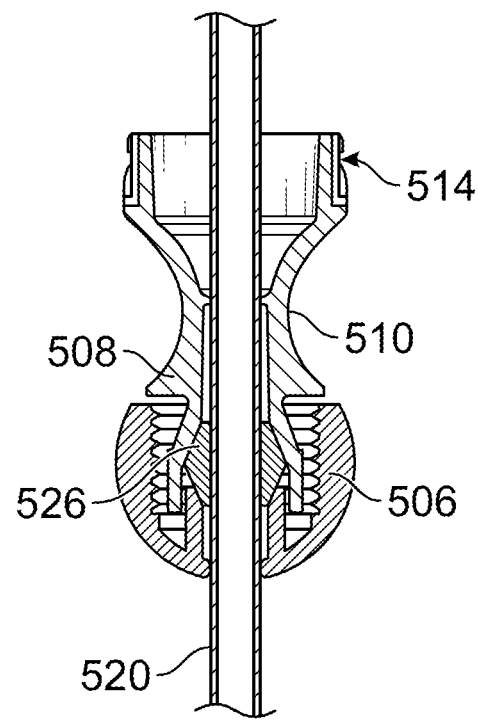

Referring to FIGS. 5A and 5B, the portal grip (502) of an integrated device (500) may include a ball structure (504) comprising a first component (506), a second component (508), and a waist region (510). The waist region (510) may include a first end (512), a second end (514), and a smaller diameter midsection (516) therebetween. In some instances, the first end may be a distal end of the waist region, and have a diameter larger than the smaller diameter midsection, but larger than the second end, which may be a proximal end of the waist region. The portal grip (502) may be slidingly advanced along portal cannula (520) to a position that seats it against the skin surface (522). The portal grip (502) may be locked at this position, as further described below, and function as a fulcrum point for the portal cannula (520). In some variations, the second end of the waist region may include a plurality of ribs or other surface features (e.g., nubs, bristles, texturization) that help a user grip and rotate the second component with respect to the first component. For example, as shown in FIG. 5C, the second end (514) of the waist region (510) may be configured to include a plurality of ribs (524) that may aid the user in rotating the second component (508) with respect to the first component (506) about the portal cannula (520). FIG. 5D provides a cross-sectional view of the portal grip shown in FIG. 5C including a collet (526), described in more detail below, concentrically disposed about the portal cannula (520) that conforms to and compresses against the outer surface of the portal cannula (520) to prevent movement of the portal grip (502) along the length of the portal cannula (520).

Lock Assemblies

The portal grip may include a housing containing a lock assembly that releasably secures the portal grip to the portal cannula at one or more positions. In general, the portal grip may be locked to the portal cannula at a position where the portal grip contacts the skin surface such that it may function as a fulcrum for the portal cannula. Additionally, the lock assembly may be configured to maintain the position of the portal grip along the length of the portal cannula irrespective of additional lubricity from exposure to fatty lipids or a body fluid. The lock assembly may have various configurations and may be generally configured for use with a single hand.

In some variations, the lock assembly may include a collet configured to be concentrically disposed about the portal cannula. The collet may be configured to conform to and compress against the outer surface of the portal cannula to prevent movement of the portal grip along the length of the portal cannula. The collet may be made, for example, from polymeric materials. Non-limiting examples of polymeric materials include acrylonitrile butadiene styrene (ABS), polycarbonate, polycarbonate/ABS blends, and copolymers thereof.

Figure 6C:
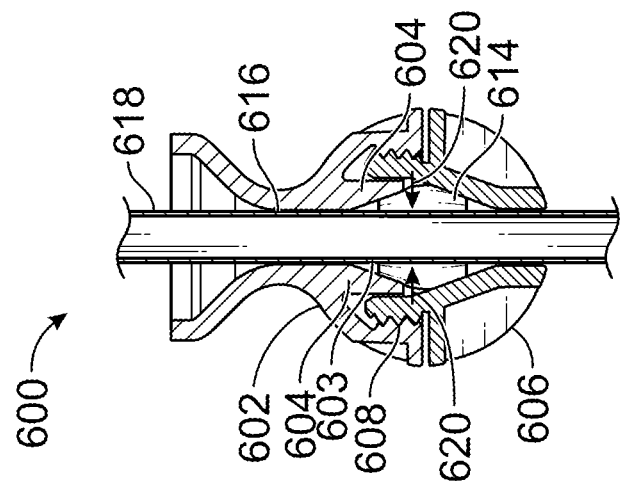
FIGS. 6A-6C depict an exemplary variation of lock assembly comprising a portal grip housing including rotating hemispheres (first component, second component) and a conformable collet.
Figure 6B:
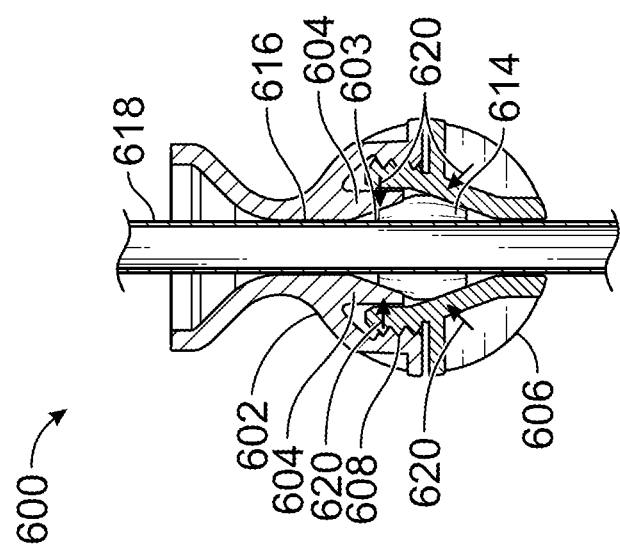
Figure 6A:
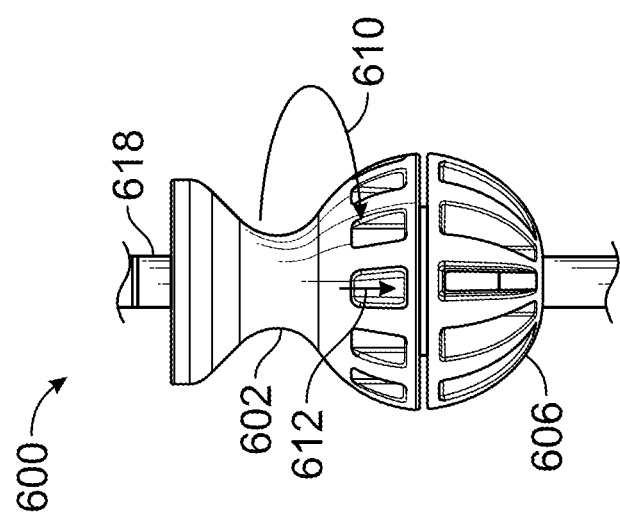

In one variation, the collet may be circumferentially disposed about the portal cannula and configured to compress against the outer surface of the cannula when the first and second portal grip components are rotated, e.g. with right-handed threading (clockwise rotation to tighten and counterclockwise rotation to loosen). Ramps provided within one or both portal grip hemispheres may aid in collet compression. For example, referring to FIGS. 6A-6C, the portal grip (600) may have a first component such as proximal hemisphere (602) including a ramp (604) coupled to a second component such as distal hemisphere (606) via a threaded connection (608). Clockwise rotation of the proximal hemisphere (602) with respect to the distal hemisphere (606), as indicated by arrow (610), may cause the two hemispheres (602, 606) to translate axially towards each other, as shown by arrow (612). This axial translation may result in the ramp (604) compressing the collet (614), which is circumferentially disposed about the portal cannula (618) within the portal grip lumen (603), against the outer surface (616) of the portal cannula (618), as shown by arrows (620). As further engagement with the ramp (604) is achieved, compression of the collet (614) against the portal cannula outer surface (616) may be increased, thereby temporarily locking the position of the portal grip (600) on the portal cannula (618).

In another variation, the lock assembly may comprise a collet having a plurality of fingers spaced about a circumference of the collet. The plurality of fingers may include between two to six fingers. For example, the plurality of fingers may include two, three, four, five, or six fingers. In some cases, the collet may include more than six fingers (e.g., seven, eight, nine, ten, or more fingers). The plurality of fingers may be spaced apart by channels and symmetrically or asymmetrically spaced about the collet circumference. In some variations, the collet comprises three fingers that are spaced 120 degrees about the collet circumference and three channels that are also spaced 120 degrees apart. The channels may provide space for the collet to compress against the portal cannula. Furthermore, the channels may include an open end and a closed end. The open ends of adjacent channels may be on opposite sides of the collet.

The length of the fingers may generally be the same as the length of the collet, which may range from about 8 mm to about 20 mm, including all values and sub-ranges therein. For example, finger length may be about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm. In one variation, the finger length may be about 9 mm. In some variations, the length of the fingers may be shorter than the length of the channel. In some instances, the length of the fingers may be longer than 20 mm.

Figure 7A:
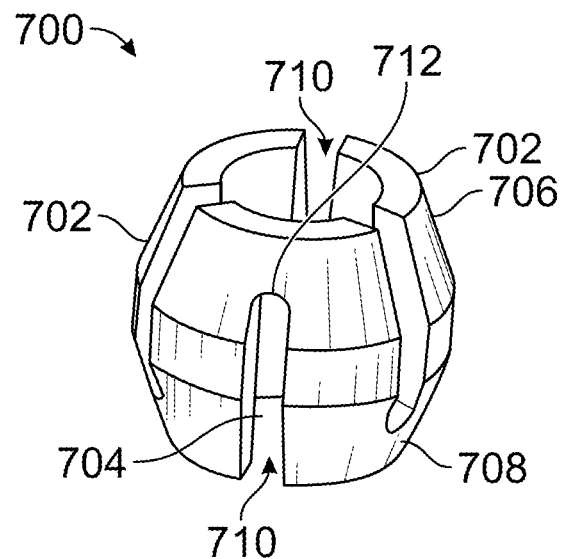
FIGS. 7A and 7B depict another exemplary variation of a lock assembly comprising a collet having a plurality of fingers separated by a plurality of channels.
Figure 7B:
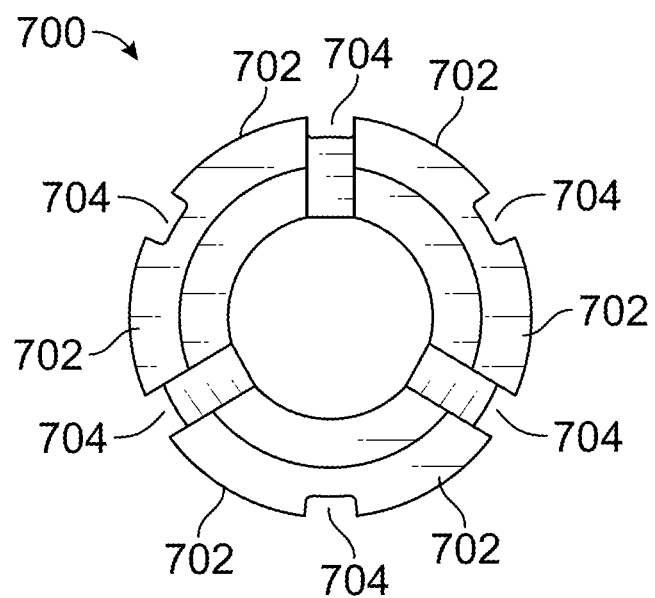

Referring to FIGS. 7A and 7B, the collet (700) may include a first end (706), a second end (708), and a plurality of fingers (702) spaced apart by a plurality of channels (704). Each of the plurality of channels (704) has an open end (710) and a closed end (712). The open ends (710) of adjacent channels may be disposed on different ends of the collet, e.g., an open end of a channel may be disposed on the first collet end (706) and the closed end of the channel may be disposed on or facing the second collet end (708). Similarly, the closed ends (712) of adjacent channels may be disposed on or facing different ends of the collet. It should be appreciated that one or more channels may not extend the entire length of the collet and the closed ends (712) of one or more channels may be inset from the end of the collet (as depicted in FIG. 7A).

Although FIGS. 7A and 7B show a collet having six fingers and six channels symmetrically spaced about the collect circumference, in other variations, a lower number of channels may be used, and/or they may be asymmetrically spaced apart. The channels may provide space for the collet fingers to expand against the portal cannula when compressed. The fingers may also help ensure that the compressive force is evenly distributed on the portal cannula.

Some variations of the lock assembly may include a cam lock. The cam lock may include a split spiral cam that may be configured to tighten around the portal cannula when rotated. The split spiral cam may be disposed within a notch in the housing of the portal grip, and coupled to either the first component (e.g., a proximal hemisphere) or the second component (e.g., a distal hemisphere) of the portal grip. In order for the split spiral cam to tighten upon application of a rotational force, the inner diameter friction of the cam against the portal cannula may be greater than the outer diameter friction of the cam against the portal grip housing. Similar to the collet, the split spiral cam may be made from, for example, polymeric materials. Non-limiting examples of polymeric materials include acrylonitrile butadiene styrene (ABS), polycarbonate, polycarbonate/ABS blends, and copolymers thereof.

Figure 8A:
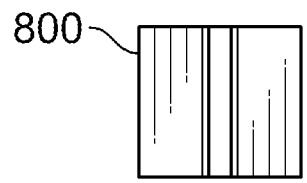
FIGS. 8A-8D depict yet another exemplary variation of a lock assembly comprising a split spiral cam.
Figure 8B:
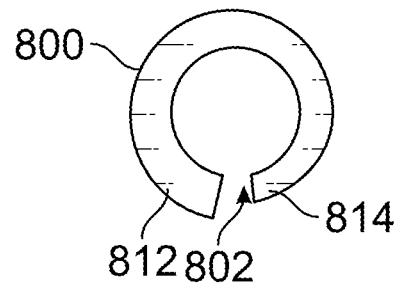
Figure 8C:
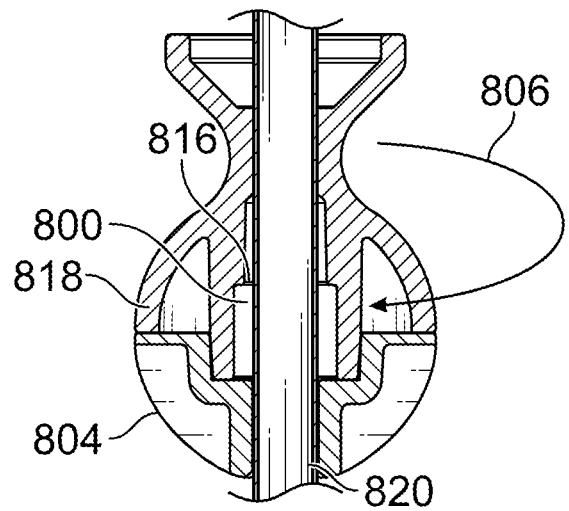
Figure 8D:
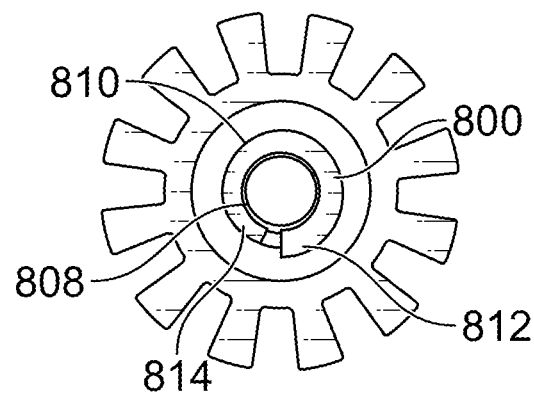

An exemplary lock assembly including a split spiral cam is illustrated in FIGS. 8A to 8D. Referring to FIG. 8A (side view) and 8B (top view), the spiral cam (800) is shown to have a split (802) that forms two free ends (812, 814). When the split spiral cam (800) is provided within a groove (816) of the proximal hemisphere (818) of portal grip (804), rotation (e.g., clockwise rotation) of the portal grip (804) in the direction of arrow (806) may tighten the spiral cam about the portal cannula (820) thereby securing the portal grip (804) to the portal cannula (820). The split spiral cam (800) may have an inner diameter (808) and an outer diameter (810). The friction of the inner diameter (808) against the portal cannula (820) may be greater than the friction of the outer diameter (810) against the portal grip (804) upon rotation, as previously mentioned, so that the ends (812, 814) of the split spiral cam (800) may tighten around the portal cannula upon application of a rotational force.

Figure 9A:
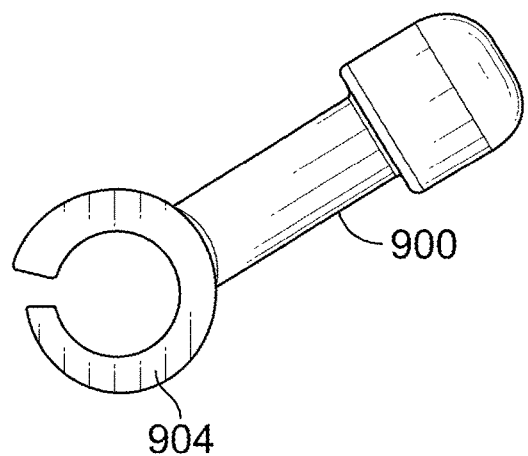
FIGS. 9A-9E depict an exemplary variation of a split spiral cam including a toggle to aid with rotating the cam into the locked and unlocked positions.
Figure 9B:
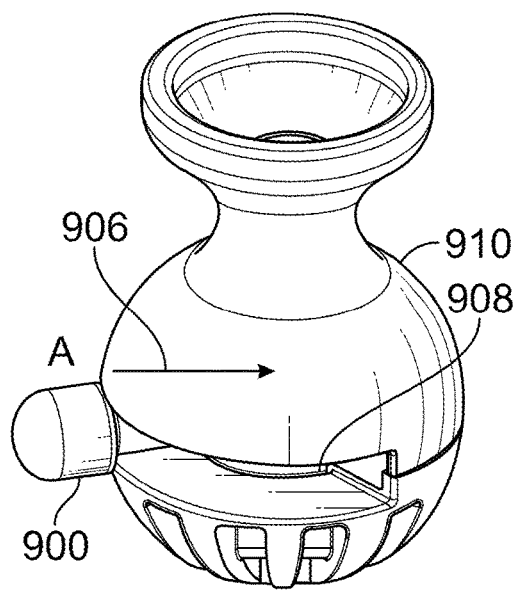
Figure 9C:
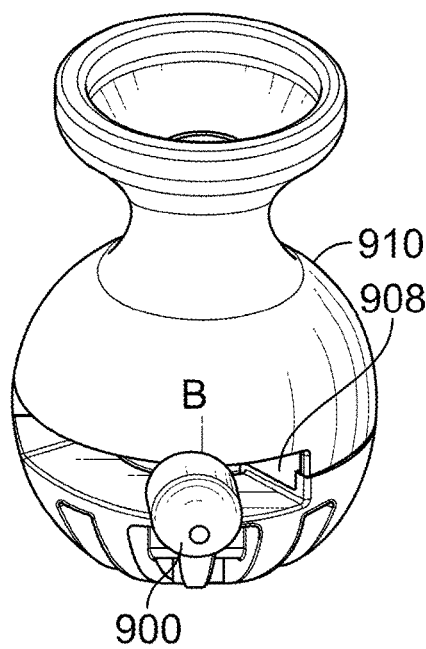
Figure 9E:
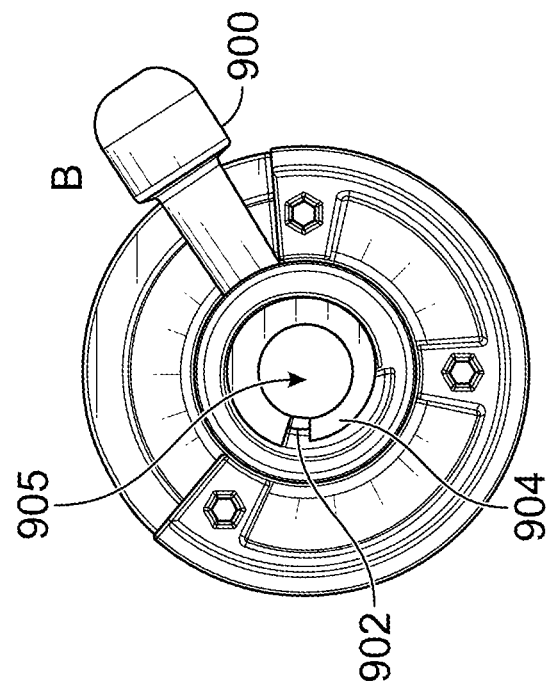
Figure 9D:
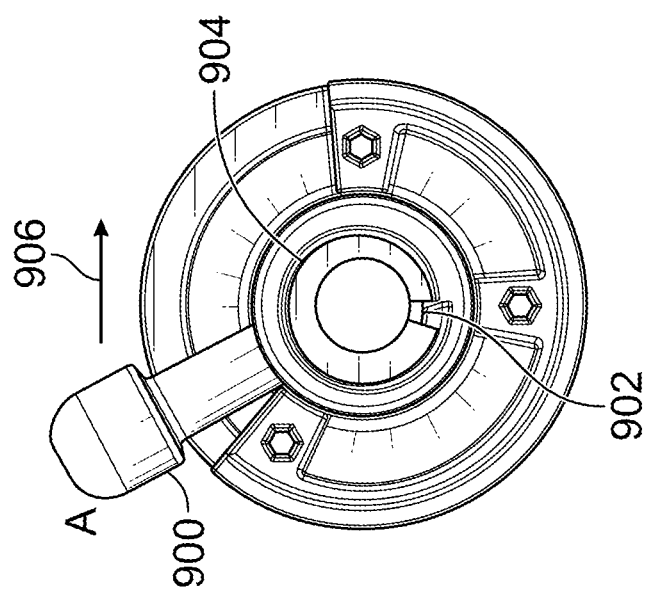

In another variation, and to aid with rotation and tightening of the split spiral cam, a toggle may be attached thereto to rotate the cam into the locked and unlocked positions. For example, referring to FIG. 9A, a toggle (900) is shown fixed to a split spiral cam (904). When the toggle (900) is rotated within a slot (908) in the portal grip housing (910) from position A (shown in FIGS. 9B and 9D) in the direction of arrow (906) to position B (as shown FIGS. 9C and 9E), the split spiral cam (904) may then also rotate within a corresponding cam rider groove (902) within the portal grip housing (910). Given the spiral geometry of the split spiral cam (904) and cam rider groove (902), the outer surface of the groove (902) constricts around the cam (904) as the cam (904) is rotated to travel along the groove (902), thereby constricting and compressing the cam (904) against a portal cannula (not shown) within the central opening (905).

Figure 10A:
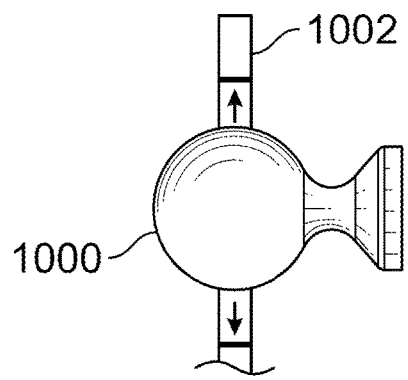
FIGS. 10A-10D depict a further variation of a lock assembly in which the portal grip functions as a toggle lever.
Figure 10B:
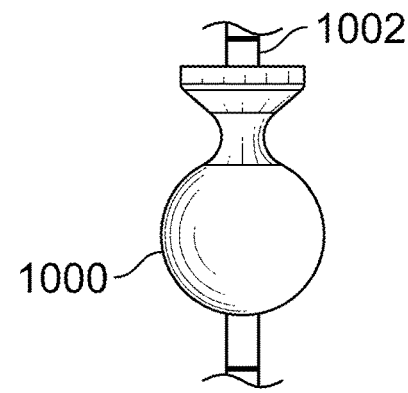

In some variations, the portal grip itself functions as a toggle lever when axially aligned with the portal cannula to releasably secure the portal grip to the portal cannula. More specifically, and as shown in FIG. 10A, when the portal grip (1000) is in a lateral orientation, it may be free to slide along the portal cannula (1002) in the direction of the arrows. However, when flipped (e.g., rotated 90 degrees) to a vertical orientation, as shown in FIG. 10B, the portal grip (1000) may be locked to the portal cannula (1002). Flipping the portal grip (1000) back to the lateral orientation unlocks it, allowing the portal grip to again be capable of sliding along the portal cannula to another position thereon.

Figure 10C:
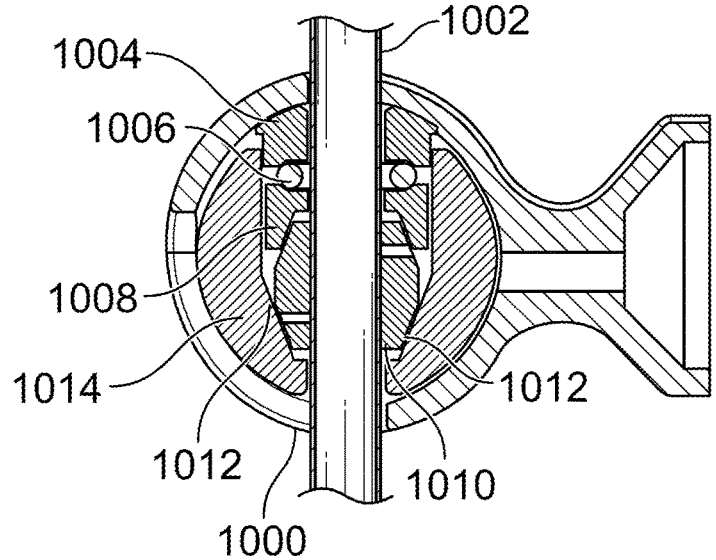
Figure 10D:
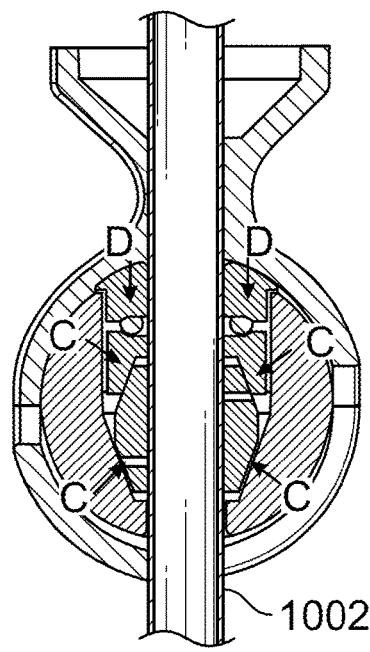

When the portal grip functions as a toggle lever, the lock assembly may include one or more components within the portal grip housing that may be compressed to releasably secure the portal grip to the portal cannula. In one variation, the locking assembly may comprise a cam rider, a compliance member, a ramp, and any one of the collets described herein. As shown in FIGS. 10C and 10D, the cam rider may be coupled to the housing of the portal grip. In the lateral orientation provided in FIG. 10C, the cam rider (1004) and ramp (1008) are shown in their initial configurations, and the compliance member, which is depicted here, for example, as an O-ring (1006), and collet (1010) are shown in their uncompressed configurations. Upon rotation of the portal grip from the lateral to the vertical orientation, as shown in FIG. 10D, the cam rider (1004) may be displaced in a downward direction, as shown by the arrows (D). Displacement of the cam rider (1004) may then compress the O-ring (1006) and downwardly displace the ramp (1008), which in turn compresses the collet (1010) against the portal cannula in the direction of the arrows (C). Internal ramps (1012) on an aligning guide (1014) may also help compress the collet (1010) axially inward towards the surface of the portal cannula (1002).

Figure 11B:
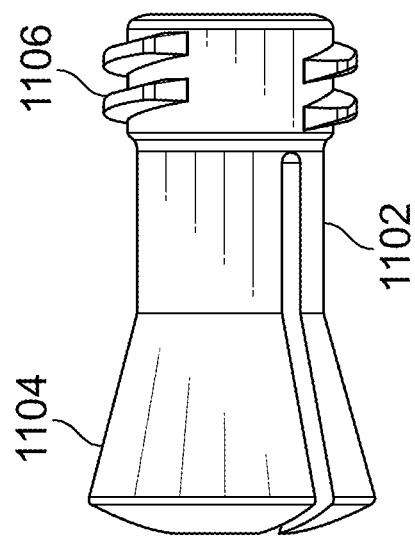
FIGS. 11A-11F depict yet a further variation of a lock assembly including a collet having a plurality of jaws that may be locked and unlocked by a slidable portal grip housing.
Figure 11D:
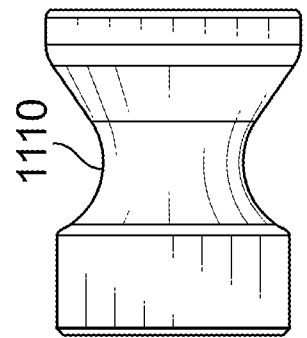
Figure 11A:
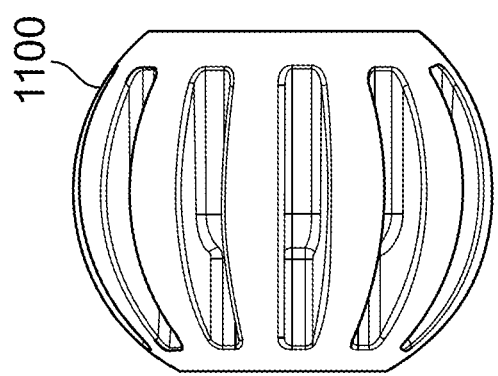
Figure 11C:
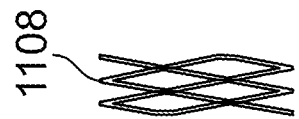
Figure 11F:
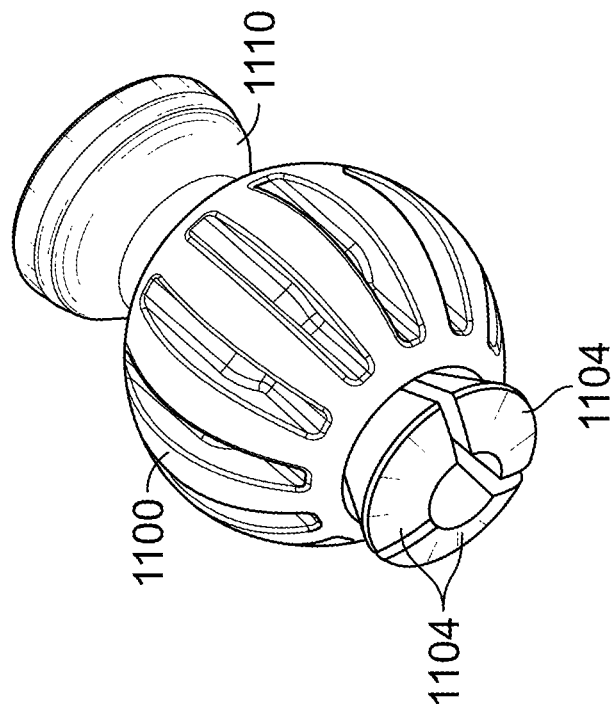
Figure 11E:
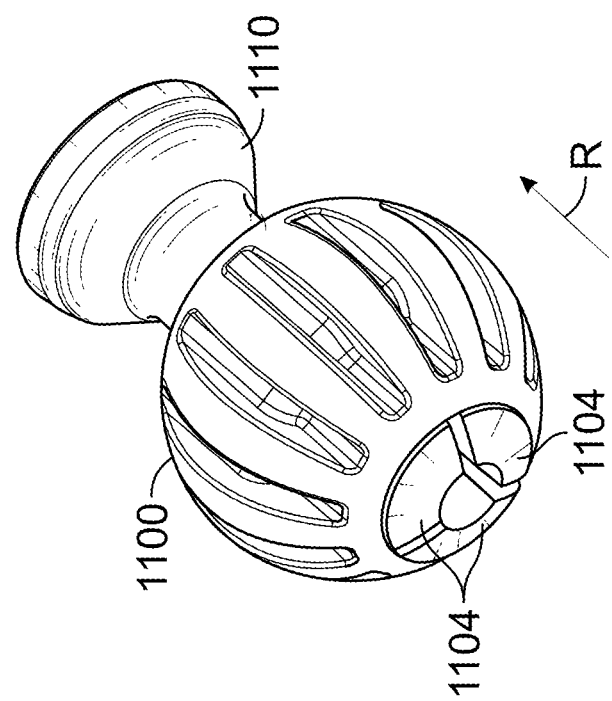

In other variations, the lock assembly may comprise a portal grip housing configured to be slidably disposed on the collet. The portal grip housing may maintain the collet in the compressed (locked) state when entirely covering the collet, and may release the compression to transition the collet to the unlocked state when retracted, such that at least a portion of the collet is not covered by the portal grip housing. For example, referring to FIGS. 11A to 11D, the lock assembly may include a spherical portal grip housing (1100) and a collet (1102) comprising a plurality of jaws (1104) that are biased to an expanded (unlocked) state. The collet (1102) includes a spring mount (1106). The lock assembly may further include a compressible spring (1108) and a waist (1110). The collet may be made from compressible materials as previously described. When assembled, as shown in FIG. 11E, the spherical portal grip housing (1100) may be disposed about the collet (1102) and biased by the spring (1108) on the spring mount (1106) to hold the collet jaws (1104) (here, three) in their compressed configuration. In the compressed configuration, the collet jaws (1104) may releasably secure the spherical portal grip housing (1100) to the portal cannula (not shown). When repositioning is desired, the spherical portal grip housing (1100) may be retracted in the direction of arrow (R). As shown in FIG. 11F, retraction of the spherical portal grip housing (1100) may remove the compressive force from the collet jaws (1104) such that they transition to their expanded state.

Figure 12A:
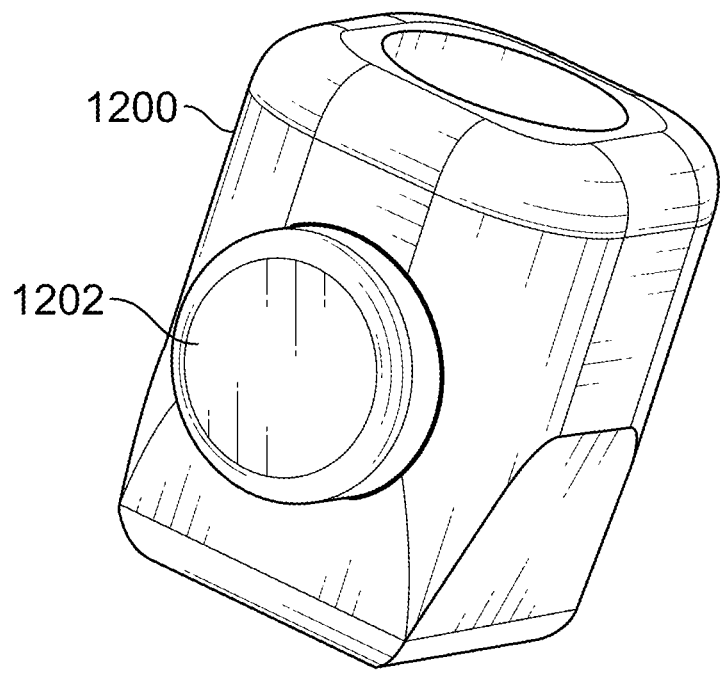
FIGS. 12A and 12B depict an exemplary push button lock assembly.
Figure 12B:
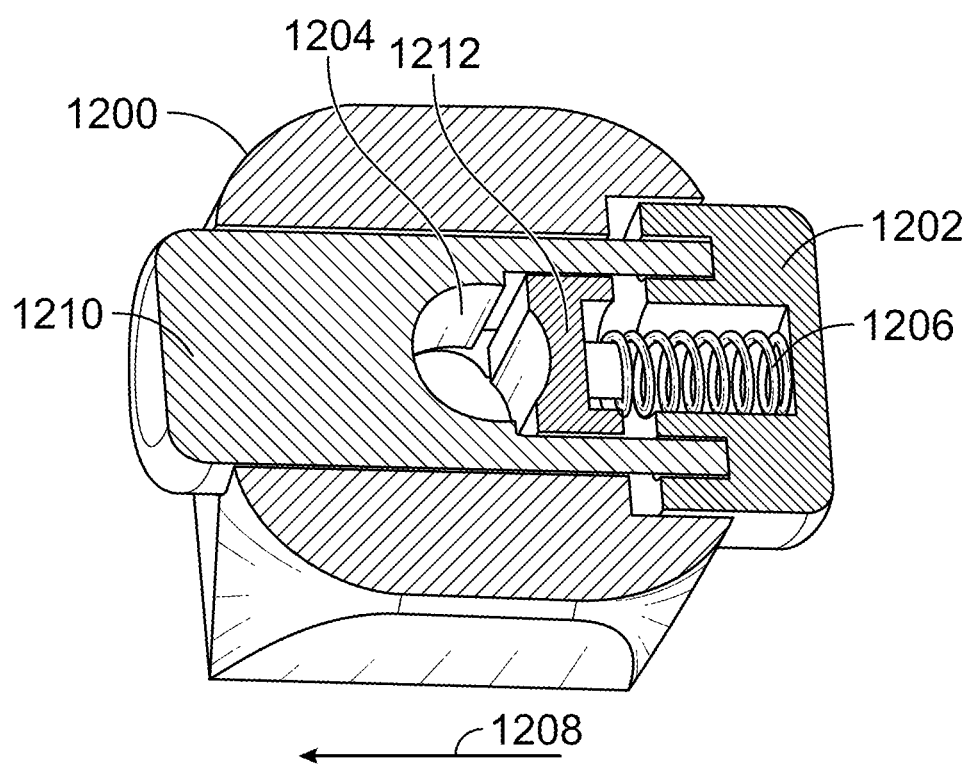

The lock assembly may also comprise a pressable portion of the portal grip, such as a push button, and a clamp. In this variation, the push button may be depressed to compress a spring, which in turn unlocks the portal grip from the portal cannula. The push button may be released to lock the portal grip thereto. For example, referring to FIGS. 12A and 12B, the portal grip (1200) may have a rectangular cross-sectional shape. The corners of the portal grip (1200) may be radiused so that movement thereof against the skin surface does not cause tissue damage. A spring (1206) and a spring cap (1212) may bias a button (1202) to an undepressed/locked state, as shown in FIG. 12B. When the button (1202) is depressed in the direction of the arrow (1208) to overcome the force from the spring (1206), the clamp (1210) moves laterally, also in the direction of arrow (1208), to loosen the clamp (1210) about a cannula portal 1204 on the opposing side, thereby releasing the portal grip (1200) from the portal cannula.

Trocar

The integrated devices described herein may include a trocar slidingly disposed within the portal cannula lumen. The trocar may comprise an awl or shaft having a proximal end, a distal end, and a distal tip that is generally sharp so that it may be used to percutaneously create a tunnel through tissue to a spinal region for performing a spinal procedure. A handle may be provided at the proximal end of the awl to help with trocar manipulation. In some variations, the handle may be T-shaped to accommodate a variety of hand postures, provide a more comfortable wrapped-finger-controlled posture upon insertion and extraction of the trocar, as well as a more comfortable steering posture upon insertion. After access to the spinal region is created, the trocar may be withdrawn, leaving the portal cannula within the percutaneously created passage.

The awl or shaft may be made from metals such as, for example, stainless steel, nitinol, and/or alloys thereof. With respect to the trocar handle, it may be made from the same polymers as the portal grip and collet. These polymers include without limitation, acrylonitrile butadiene styrene (ABS), polycarbonate, polycarbonate/ABS blends, and copolymers thereof.

Figure 13:
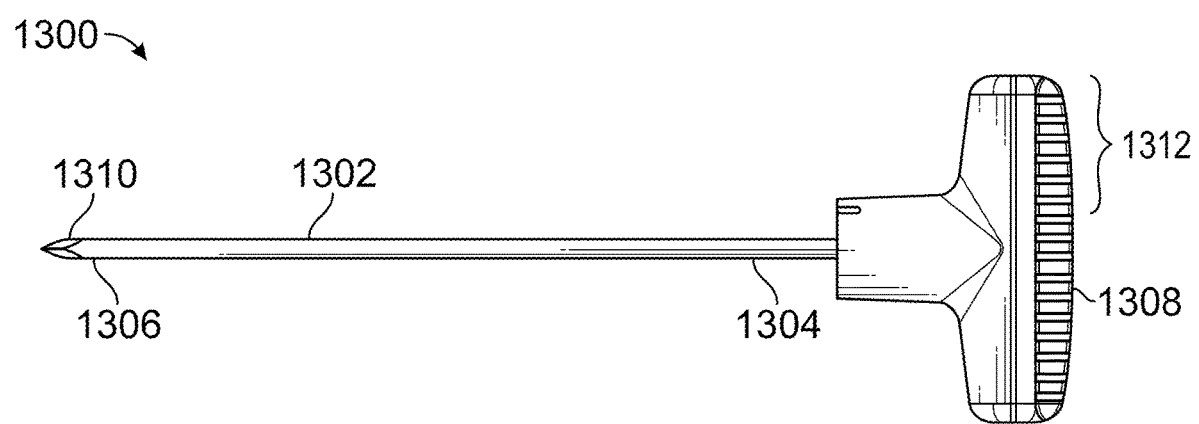
FIG. 13 depicts an exemplary trocar of the integrated device.

Referring to FIG. 13, an exemplary trocar (1300) is shown comprising an awl (1302) having a proximal end (1304) and a distal end (1306). A T-shaped handle (1308) may be attached to the proximal end (1304). The distal end (1306) may include a sharp tip (1310) for penetrating tissue. In this variation, the T-shaped handle (1308) may provide a larger grip area for improved handling of the trocar as well as increased comfort when the fingers are distributed to hold the trocar. For example, the portion of the grip or purchase (1312) on each side of the handle may be about 2.0 cm.

The handle of the trocar may be comprised of a single component or multiple parts that are coupled together. In a variation in which the handle comprises multiple parts (e.g., two, three, four, or more), the parts may be coupled to one another via a snap-fit or interference fit connection, magnetic connection, and/or by a mechanical connector, e.g., a threaded connector. In some variations, as shown in FIGS. 16A-16D, the trocar handle may include two parts, a housing (1602) and an insert (1604). The insert (1604) may include a plurality of (e.g., two, three, four, or more) posts (1606) that couple to (e.g., may be received within) corresponding recesses (1608) in the housing (1604). In some variations, the posts (1606) and the recesses (1608) may be coupled to one another using an interference fit. As shown in FIG. 16C, the posts (1606) may have a cruciform cross-sectional profile, but other cross-sectional shapes may be used, e.g., circular, ovular, triangular, square, etc., as long as the post is capable of securely fitting within, or otherwise coupling to, the recess (1608). The insert and housing may be made from polymers such as, but not limited to, acrylonitrile butadiene styrene (ABS), polycarbonate, polycarbonate/ABS blends, and copolymers thereof.

Depth Guide

The depth guide may be removably coupled to the hub of the portal cannula via any suitable connection, e.g., via a snap-fit or interference fit connection, magnetic connection, and/or by a mechanical connector, e.g., a threaded connector. The depth guide may be configured to transfer rotational movement into linear movement, and control the amount of extension of a working instrument from the portal cannula, as further described below. The depth guide (see element 110 in FIG. 1B) of the integrated device may function by threading or unthreading two components to telescope them at user defined lengths. In addition, the depth guide may be detachable to facilitate the need for additional working length.

The depth guide may include a knob and a graduation scale that represents the disposition of instruments with respect to the distal tip of the portal cannula. The initial position of the depth guide may represent 15 mm of instrument extension from the portal cannula distal tip. Instrument extension may range from about 22.5 mm to about 10 mm (which allows the instrument to translate axially about 12.5 mm). Additionally, the depth guide may be configured to provide tactile feedback of depth with a click (e.g., audible or non-audible) about every 2.5 mm of translation (e.g., every half knob rotation). For example, referring to FIGS. 14A-14C, a depth guide (1400) is shown attached to a hub (1402) of a portal cannula (1404). The depth guide (1400) may include a knob (1406) and a graduation scale (1408). At the initial position (shown in FIG. 14A), the graduation scale (1408) may indicate that an instrument is extended about 15 mm from the portal cannula distal tip. When the knob (1406) is rotated counterclockwise to the full extent, the graduation scale may indicate that an instrument is extended about 10 mm from the portal cannula distal tip (see FIG. 14B). When the knob (1406) is rotated clockwise to the full extent such that the knob (1406) contacts the portal cannula hub (1405), the depth guide (1400) may allow the maximum amount of instrument extension (see FIG. 14C).

Figure 17B:
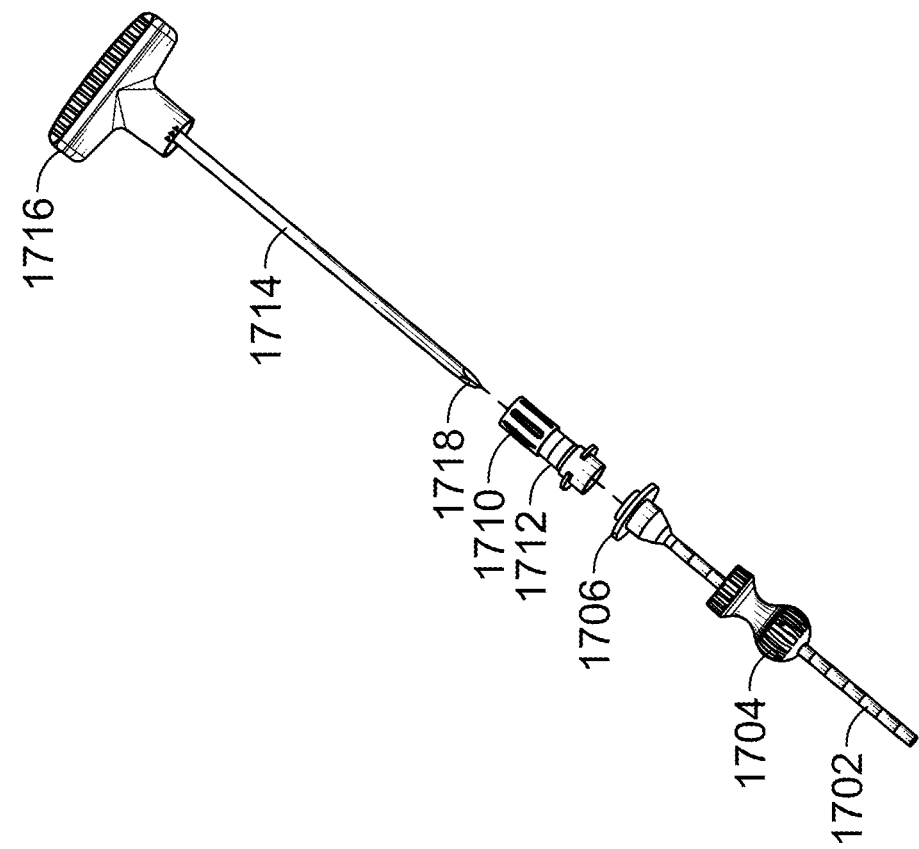
Figure 17A:
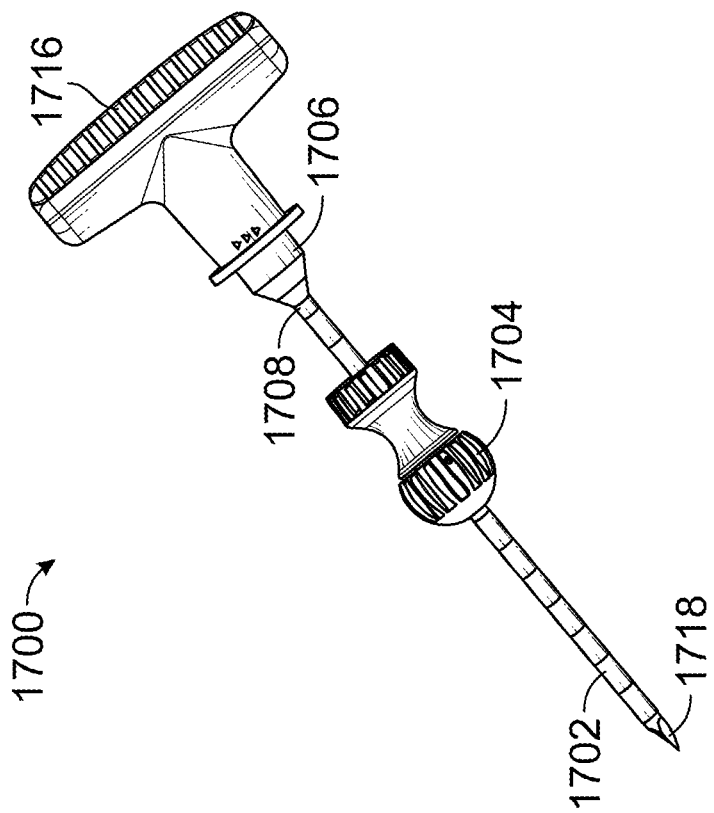

Some variations of the integrated devices may be configured as shown in FIGS. 17A to 17D. Referring to FIGS. 17A and 17B, the integrated device (1700) may include a portal cannula (1702) and a portal grip (1704), as described in more detail with respect to FIGS. 5C and 5D. The portal grip (1704) may be slidingly attached to the portal cannula (1702) and may be held at a particular axial location along the portal cannula (1702) when in a locked configuration, for example, when collet (1724 in FIG. 17D) is compressed against the portal cannula (1702). The portal cannula (1702) may include a hub (1706) at its proximal end (1708). A trocar (1714) including a handle (1716) at its proximal end and a sharp tip (1718) at its distal end may extend through the portal cannula (1702). Furthermore, a connector (1712) having a proximal end (1701) and a distal end (1703) may be used to releasably couple (e.g., attach and detach) a depth guide (1710) to the hub (1706). More specifically, the proximal end (1701) of the connector (1712) may be configured to releasably couple to a distal end (1705) of the depth guide (1710). Coupling may be accomplished via a snap-fit or interference fit connection, by a threaded connection, or by a magnetic connection. As shown in FIGS. 17C and 17D, the distal end (1703) of the connector (1712) may include detents (1720) configured to releasably couple (e.g., by a snap-fit connection) to the hub (1706). Although detents (1720) providing a snap-fit connection are shown in FIGS. 17C and 17D, the distal end of the connector (1712) may attach and detach to the hub (1706) in other ways, e.g., by an interference fit connection, threaded connection, or a magnetic connection.

Working Instruments

Once the target depth of the portal cannula is set, working instruments may be advanced through the portal cannula to perform a spinal procedure. As previously mentioned, examples of working instruments may be bone augers, hand-operated mechanical biting instruments such as bone rongeurs, mechanical scooping devices such as tissue sculptors, power-operated mechanical instruments such as grinders and drills, and light guiding and/or visualization devices, e.g., endoscopes. Other examples of working instruments may include suction and irrigation catheters, sensors, monitoring devices, and electric, magnetic, electromagnetic, vibration, sound, and kinetic energy delivering components such as RF probes, ultrasound probes, ablation devices, and energy delivering wires. In some instances, the working instrument may use streams of fluid to modify tissue. In one variation, working instruments for performing a laminectomy and/or removing ligamentum flavum for the treatment of spinal stenosis are advanced. In this variation, exemplary working instruments may include a bone auger, a bone rongeur, and a tissue sculptor.

The integrated assembly (including, e.g., the portal cannula with a trocar removably disposed therein, a portal grip slidingly coupled to the portal cannula, and depth guide attached to the portal cannula, e.g., by a snap-fit connection) and one or more working instruments may be provided together in a kit. In some variations, the kit may include some (e.g., two or more) of the components of the integrated assembly preassembled together. For example, the kit may include the portal cannula and portal grip preassembled together, or the kit may include the portal cannula and trocar preassembled together, etc. In other variations, the integrated assembly (e.g., portal cannula with a trocar removably disposed therein, portal grip slidingly coupled to the portal cannula, and depth guide attached to the portal cannula) may be provided fully assembled (e.g., all components are integrated together) in the kit. In further variations, the kit may provide the components of the integrated assembly separately so that they may be assembled just before use.

In some variations, the bone auger may be designed for safety. In such variations, forward advancement of the bone auger may be controlled to avoid rapid and inadvertent forward penetration which may result in damage to blood vessels, nerves, and surrounding tissues. In some embodiments, the bone auger may include a rounded tip shape for safety when performing a laminectomy. The rounded tip may be polished, rough, or fluted. Additionally, the rounded tip of the bone auger may include a small flat surface at the distal most portion of the tip that is substantially perpendicular to the axis of the auger to further reduce safety risks. Other features such as the number of flutes and the helix angle may improve auguring efficiency during bone auger rotation. Furthermore, features such as helix angle, rake angle, and flute depth may improve material extraction. The flute design may be chosen to achieve multiple purposes including one or more of, without limitation, engaging with bone to advance, grinding on the bone to remove hard tissue, packing the removed hard tissue inside the hollow space between the flutes to minimize the amount of bone chip left at the treatment site, and minimizing the number of times cleaning is required.

The bone auger may comprise a plurality of flutes that may function as cutting edges along the circumference of the auger. In some variations, the number of flutes may range from 1 to 100 flutes, including all values and sub-ranges therein. In some variations, the number of flutes may range from 10 to 20 flutes. For example, the bone auger may include 10, 11, 12, 13, 14, 15, 16, 17, 18, 19, or 20 flutes.

The flutes may have a rake angle relative to the normal of the helical axis ranging from about-30 degrees to about 30 degrees. For example, the rake angle may be about −30 degrees, about-20 degrees, about-10 degrees, about 0 degrees, about 10 degrees, about 20 degrees, or about 30 degrees.

Additionally, the depth of the flutes may range from about 0.10 mm to about 2 mm, including all values and sub-ranges therein. For example, flute depth may be about 0.10 mm, about 0.20 mm, about 0.30 mm, about 0.40 mm, about 0.50 mm, about 0.60 mm, about 0.70 mm, about 0.80 mm, about 0.90 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm.

The plurality of flutes may also have a helix angle ranging from about 5 degrees to about 60 degrees from the central axis of the bone auger, including all values and sub-ranges therein. For example, the helix angle may be about 5 degrees, about 10 degrees, about 15 degrees, about 20 degrees, about 25 degrees, about 30 degrees, about 35 degrees, about 40 degrees, about 45 degrees, about 50 degrees, about 55 degrees, or about 60 degrees. The helix angle may define the frequency flute wrapping around the auger shaft.

The bone auger may be made from various materials having properties useful for coring bone, and which are biocompatible and corrosion resistant. Exemplary materials may include without limitation, stainless steel and alloys thereof. In one variation, 304L Stainless (no heat treatment) may be used. In another variation, 17-4PH Stainless Steel Heat Treated to H900 specification may be employed.

Additional Examples of Integrated Devices

Some variations of the integrated devices may comprise a bone auger having a lumen and any one of the portal grips described herein slidingly coupled thereto. The bone auger may function as a portal cannula, allowing a trocar, guide wire, various working instruments, or other devices used for access, diagnosis, monitoring, and/or treatment to be inserted through the bone auger lumen. In addition to the bone auger, the trocar and/or working instrument may also include a lumen. The bone auger may include threads (flutes), as described above, at its distal end.

In use, the bone auger may be placed into or near a target treatment area of the spine over a guide wire, e.g., using the Seldinger technique. One or more dilators may be advanced over the guide wire to create a tissue tract prior to advancement of the bone auger. The one or more dilators may have a cutting tip and/or threads that allow for grinding and removal of hard tissue. In one variation, a guide wire may first be inserted and advanced into or near a target treatment area. The size of the guide wire may be selected such that it is small enough to pass through calcified structures to reach the target treatment area. The bone auger may then be inserted over the guide wire. Upon rotation, the threads of the bone auger may be used to remove bone and/or calcified structures and create a path to the treatment area. Thereafter, the guide wire may be removed and the bone auger may be used as the portal cannula through which working instruments, e.g., tissue removal instruments, may be advanced to the target treatment zone. In some variations a trocar may be disposed within the bone auger lumen and its sharp tip used to create access to the target treatment area. The trocar may or may not include a lumen. When a lumen is present, both the bone auger and trocar may be advanced to the target treatment area over a guide wire. The components of the integrated device described above may be provided pre-assembled in a kit, or as separate components for assembly by the user.

Figure 15D:
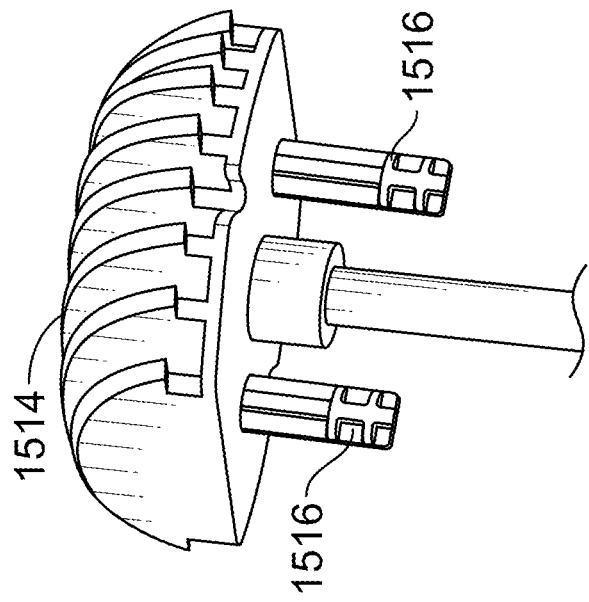
FIGS. 15C to 15F depict various views of an exemplary bone auger handle including a housing and an insert.
Figure 15C:
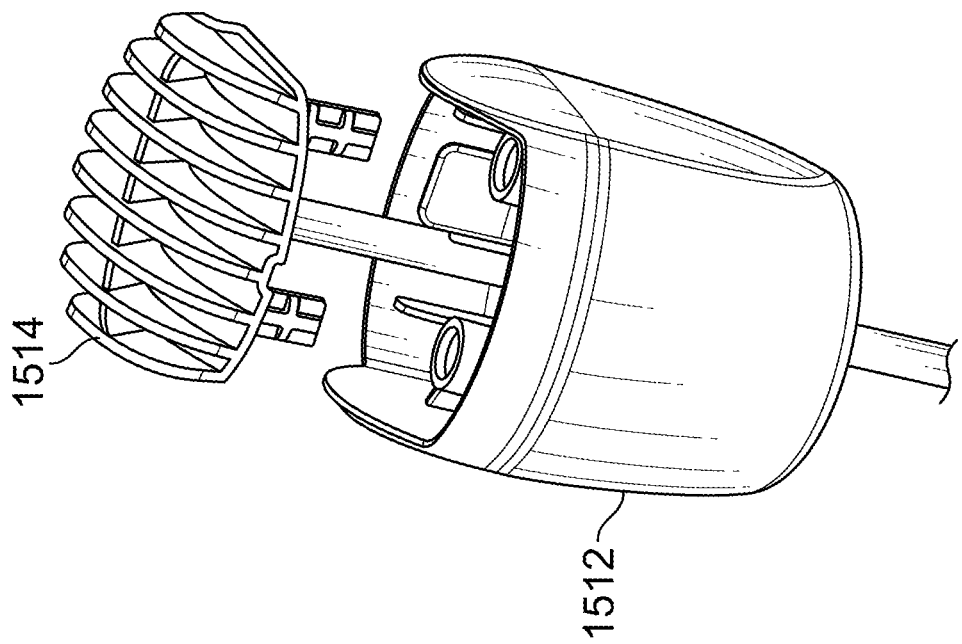
Figure 15F:
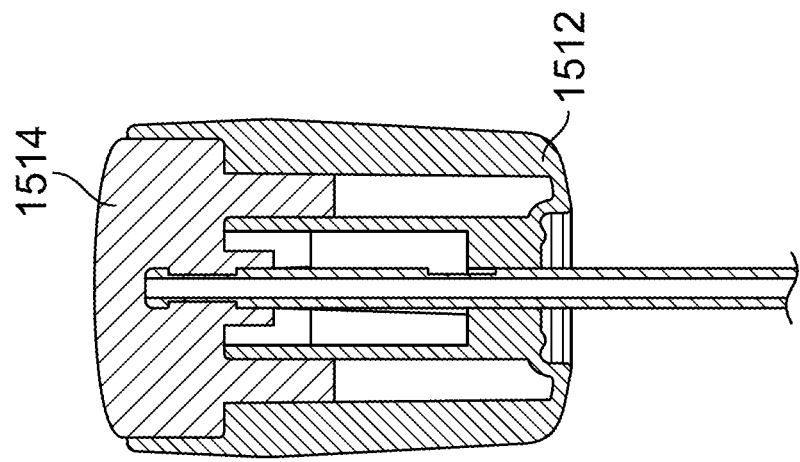
Figure 15E:
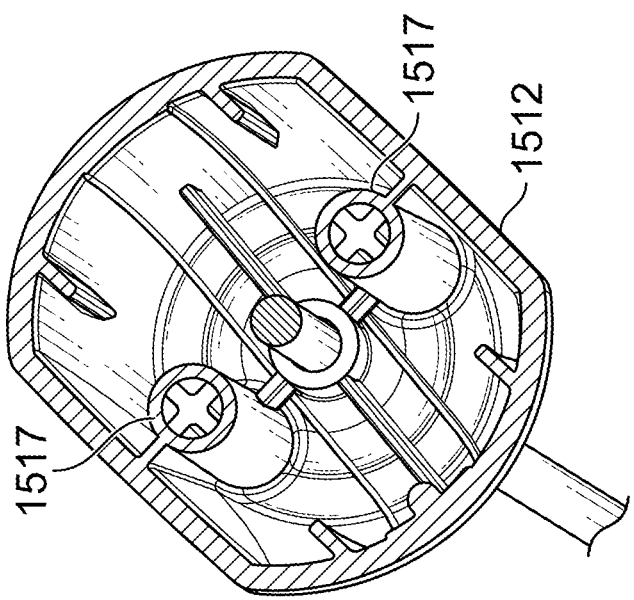
Figure 15G:
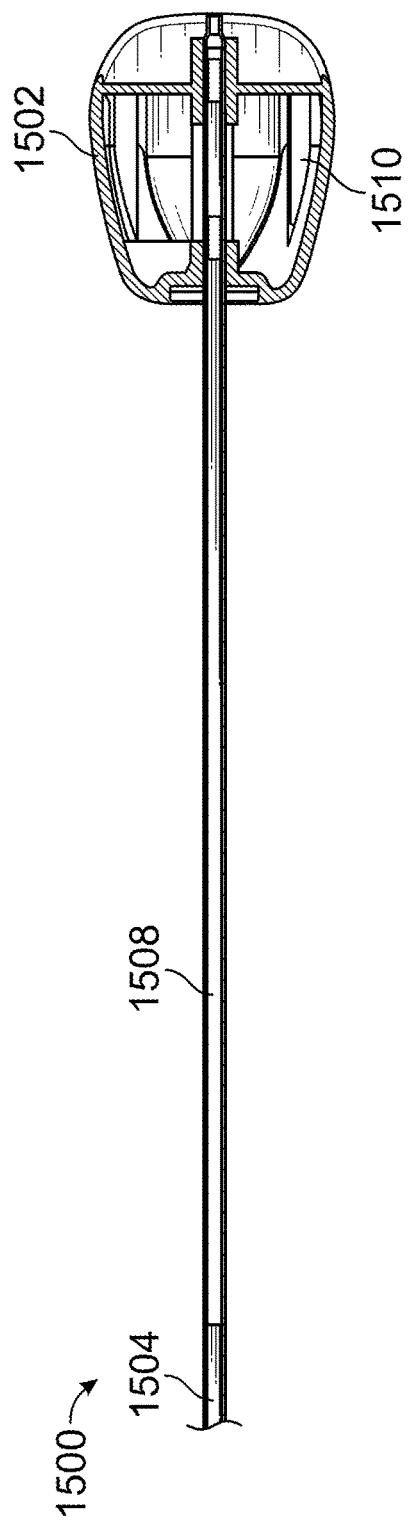
FIGS. 15G-15I depict further cross-sectional views of the integrated device of FIG. 15A.
Figure 15H:
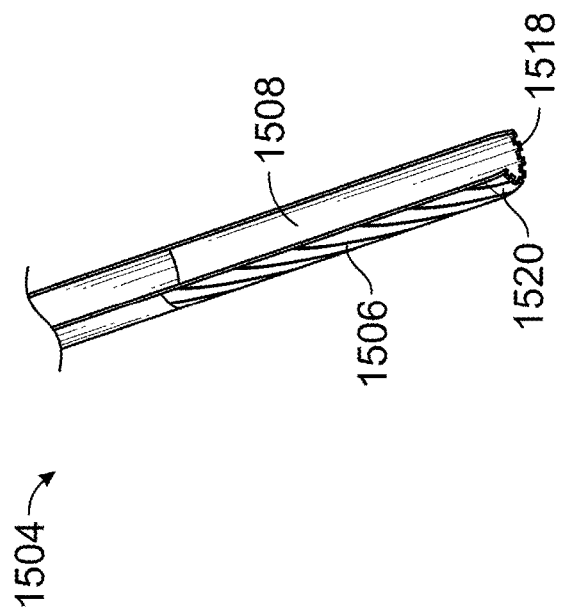
Figure 15I:
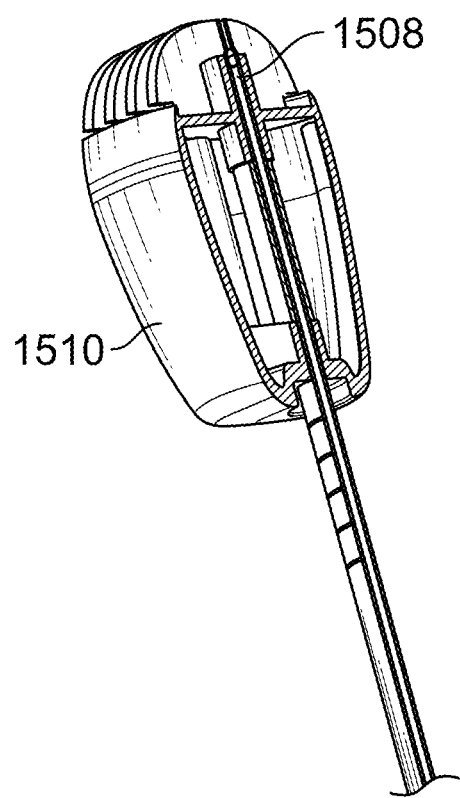

For example, as shown in FIG. 15A, the bone auger (1500) may have a proximal end (1502) and a distal end (1504). Threads (1506) may be provided at the distal end (1504) to help create access to a target treatment area through bone and/or calcified structures by rotation of the bone auger (1500). A handle (1510) may be included at the bone auger proximal end (1502) that may be gripped to help with rotation of the bone auger (1500). As shown in FIG. 15B, which is a cross-sectional view taken along line B-B in FIG. 15A, and FIG. 15G, which is a cross-sectional view of the entire device, the bone auger (1500) may have a lumen (1508) extending through the handle at the proximal end (1502) and through the distal end (1504). Thus, once access is created, working instruments may be advanced through the lumen (1508) and to the target treatment area to perform a procedure or surgery. FIG. 15H provides an enlarged, cross-sectional view of the bone auger distal end (1504) with a lumen (1508) extending therethrough. Teeth (1518) may be included at the bone auger distal tip (1520) to further aid with grinding and penetration of hard tissue, e.g., bone. In some variations, the teeth (1518) may be configured to flatten as the bone auger (1500) is advanced through hard tissue. In these instances, one or more of the teeth (1518) may have dimensions (e.g., size, shape, thickness) that allow them to transition to a flat configuration as the bone auger distal tip (1520) passes through hard tissue, or one or more of the teeth (1518) may be made from a material capable of being filed down to a flat configuration as the bone auger distal tip (1520) travels through hard tissue. While depicted above with teeth (1518), in some variations, the distal tip (1520) of the bone auger may not have teeth and may instead have continuous circumferential edge. An enlarged, cross-sectional view is also provided of the handle in FIG. 15I, which shows the lumen (1508) extending therethrough.

The handle of the bone auger may be variously sized and shaped. For example, the handle may have a cross-sectional shape like a T, L, or C, or may be spherical, oval, triangular, rectangular, or square. The bone auger handle may be made from the same polymer as or a different polymer than the portal grip, collet, and trocar handle. For example, the bone auger handle may comprise, without limitation, acrylonitrile butadiene styrene (ABS), polycarbonate, polycarbonate/ABS blends, and copolymers thereof.

The handle may be comprised of a single component or multiple parts that are coupled together. In a variation in which the handle comprises multiple parts (e.g., two, three, four, or more), the parts may be coupled to one another via a snap-fit or interference fit connection, magnetic connection, and/or by a mechanical connector, e.g., a threaded connector. In some variations, as shown in FIGS. 15C-15F, the handle (1510) may include two parts, a housing (1512) and an insert (1514). The insert (1514) may include a plurality of posts (1516) (e.g., two, three, four or more) that couple to corresponding recesses (1517) in the housing (1512) by, for example, an interference fit. In one variation, the posts (1516) may have a cruciform cross-sectional profile, but other cross-sectional shapes may be used, e.g., circular, ovular, triangular, square, etc., as long as the post is capable of securely fitting within recess (1517).

Figure 18C:
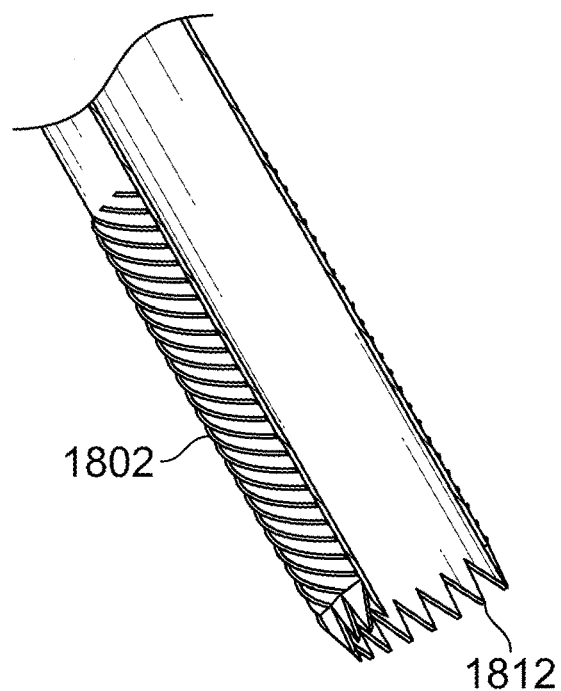

In other variations, the distal end of the portal cannula may be configured with one or more features of the bone augers described herein (e.g., threads) such that the portal cannula may act as a bone auger and create a path through hard tissue structures (e.g., bone, calcified tissues). For example, as shown in FIG. 18A, the portal cannula (1800) may comprise threads (1802) at its distal end (1804). The portal cannula (1800) may also include a lumen (1806) extending through a hub (1808) at the portal cannula proximal end (1810) and through the portal cannula distal end (1804). The lumen (1806) may allow advancement of a trocar, guide wire, various working instruments, or other devices used for access, diagnosis, monitoring, and/or treatment. In some variations, as shown in FIG. 18C, teeth (1812) may be included at the portal cannula distal tip (1814) to further aid with grinding and/or penetration of hard tissue, e.g., bone, as described above with respect to the bone auger.

Figure 18D:
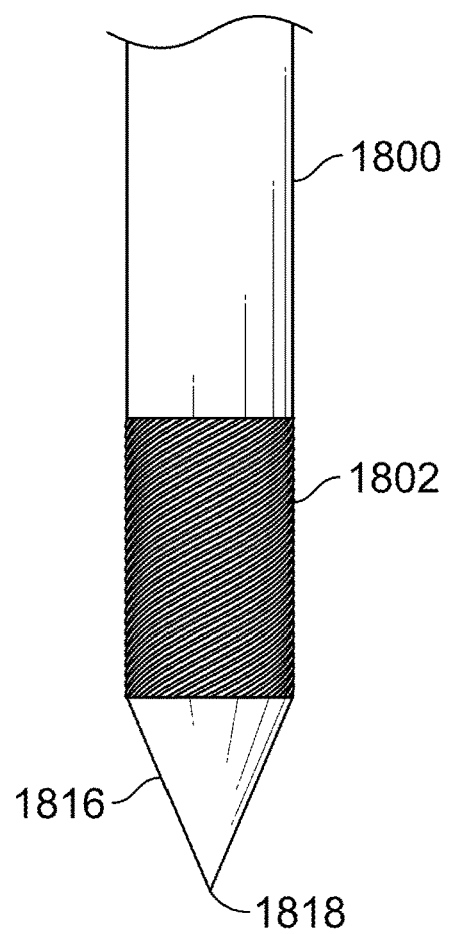

In some instances, the portal cannula may function as both a trocar and a bone auger and may be configured to include both a sharp tip to allow penetration of soft tissue followed by threads configured to create a path through hard tissue. For example, as shown in FIG. 18D, a trocar (1816) may be disposed within (e.g., concentrically) the lumen of the portal cannula (1800). Although shown as being conically shaped, the trocar tip (1818) may be configured to have other geometric shapes, e.g., a pyramidal shape. The trocar tip (1818) may be a temporary structure, as further described below. The threads may be initially covered and/or the space between the threads may be initially filled with any biocompatible material that may be bioabsorbable, biodegradable, or dissolvable such that the portal cannula may be inserted without the threads interfering with the penetration through soft tissue (e.g., using the sharp trocar tip (1818)). The bioabsorbable, biodegradable, or dissolvable materials may contain medications or other substances to treat the patient, e.g., reduce inflammation, control bleeding, reduce post-op pain, apply anesthesia, etc., These substances may be released from the material as it absorbs, degrades, or dissolves. The materials employed may be configured to absorb, degrade, or dissolve within a few seconds to minutes (e.g., about 5 seconds to about 10 minutes), depending on the particular procedure, surgery, or tissue at the target treatment area. Exemplary biocompatible materials that may be used include without limitation, one or more of metallic materials such as magnesium, zinc, and alloys thereof, and iron-based alloys, polymeric materials such as poly (L-lactide) and salicylic acid, and ceramic materials such as calcium phosphate.

In a further variation, the distal end of the trocar may be configured to include a sharp tip to penetrate soft tissue and threads positioned proximally of the sharp tip, similar to those described above for the bone auger to allow for grinding and removal of hard tissue and to create a path through hard tissue structures. The threads may be initially covered and/or the space between the threads may be initially filled with any biocompatible material that may be bioabsorbable, biodegradable, or dissolvable, and that allows for insertion of the trocar without the threads interfering with the penetration through soft tissue. The biocompatible material may be any of those described above with respect to the portal cannula. In other variations, the material may be one that breaks apart (e.g., fractures) or is stripped off upon contact with hard tissue but not soft tissue. Upon removal of the material, the threads may be exposed to engage with hard tissue. In some variations, the tip of the trocar may be made of a softer bioabsorbable material that may be shaped into the cutting tip of the trocar to initially allow penetration of the trocar into soft tissue but which becomes blunted when engaged with hard tissue.

Figure 19D:
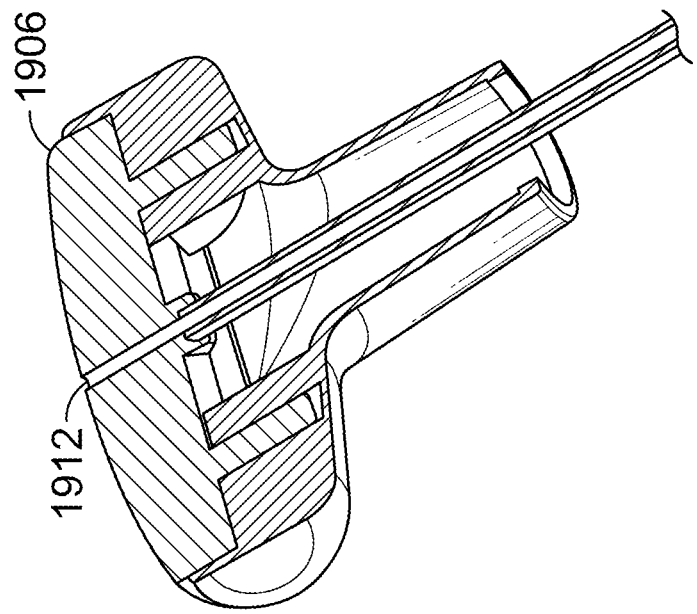
Figure 19C:
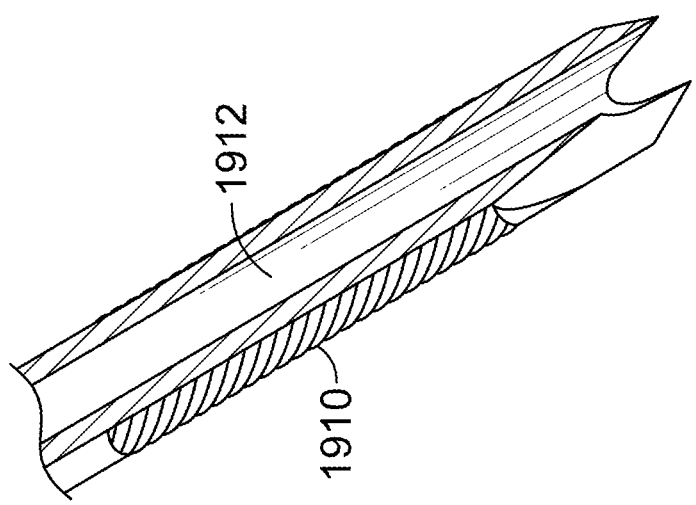
Figure 19H:
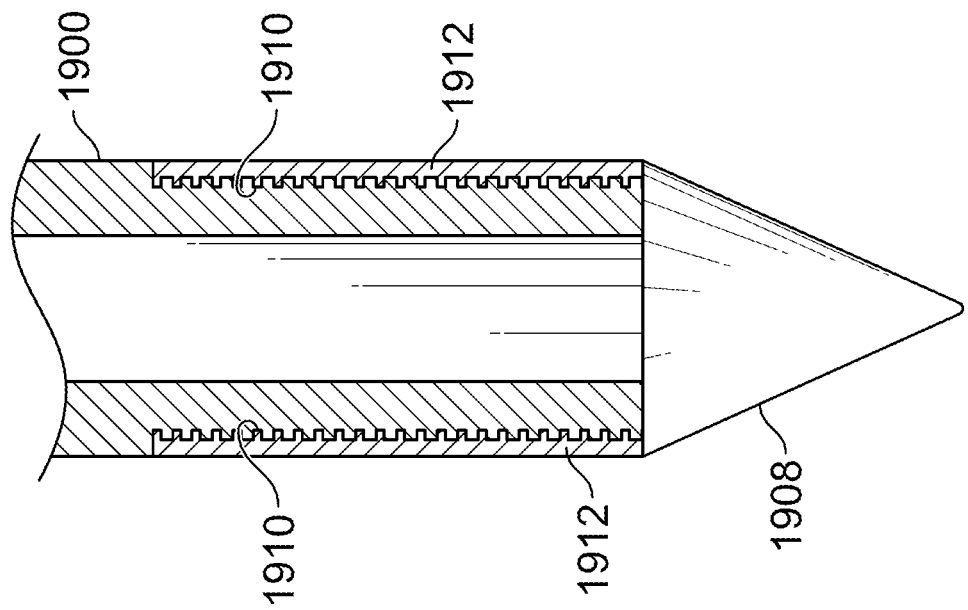
Figure 19G:
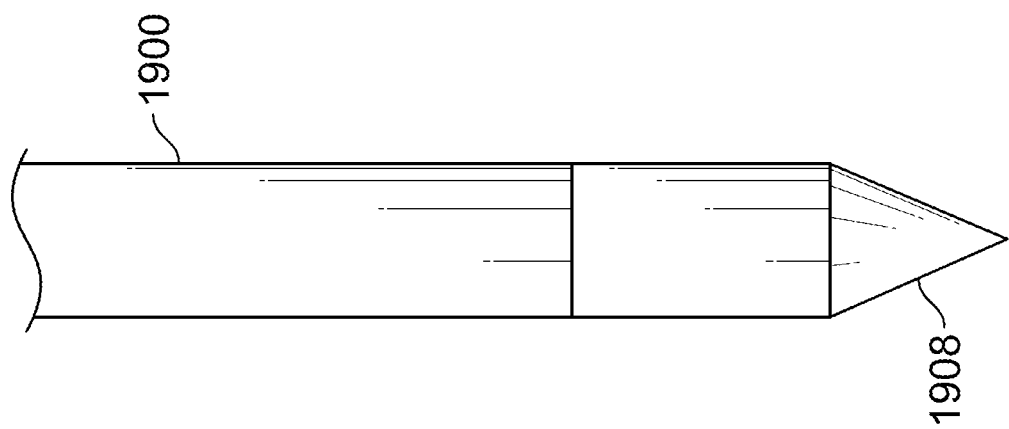

Referring to FIGS. 19A-19F, exemplary trocars that may also be used as a bone auger are shown. In FIG. 19A, the trocar (1900) may include a proximal end (1902), a distal end (1904), a handle (1906) at the proximal end (1902), and threads (1910) and a sharp tip (1908) at the distal end (1904). The sharp tip (1908) may be a temporary structure configured to be detached, e.g., by breaking, fracturing, or dissolving, after penetration through soft tissue and/or placement at the target treatment area. For example, as shown in FIGS. 19G and 19H, the sharp tip (1908) of the trocar (1900) may have a portion (1910) configured to temporarily cover the threads (1910). As noted above, although shown as being conically shaped, the sharp tip (1908) may be configured to have other geometric shapes, e.g., a pyramidal shape. Referring to FIGS. 19B-19D, the trocar (1900) may also include a lumen (1912) extending through the sharp tip (1908) and through the handle (1906). The lumen (1912) may allow advancement of a guide wire, various working instruments, or other devices used for access, diagnosis, monitoring, and/or treatment. In some variations, the sharp tip (1908) may instead be provided as part of another device that is advanced through the lumen (1912) of the trocar (1900). For example, referring to FIGS. 19E and 19F, an elongate needle (1914) may be advanced and retracted within lumen (1912). In this variation, the sharp needle tip (1909) may also be a temporary structure configured to be detached, e.g., by breaking, fracturing, or dissolving, after penetration through soft tissue and/or placement at the target treatment area.

In another variation, the integrated device may include one or more tips (e.g., a trocar tip, a bone auger tip) that may be replaced with the same or a different tip. For example, the portal cannula of the integrated device may be configured at its distal end to attach to a sharp trocar tip to penetrate soft tissue. Thereafter, the trocar tip may be replaced (e.g., switched) with a blunt bone auger tip to help pass the portal through hard tissue structures without risking damage from the sharp trocar tip. Once access to the target treatment area has been created, the bone auger tip may be removed and the portal cannula reinserted. In some variations, the one or more tips may be configured to allow penetration with a trocar, a bone auger, or working instruments. For example, the tip(s) may be equipped with a mechanism such as a push button, pull lever, or sliding doors at the tip to open the pathway for working instruments once the portal cannula is at the target treatment area. In other variations, the tip(s) may include a centrally disposed softer material in a lumen thereof through which working instruments may be advanced and retracted.

Figure 20:
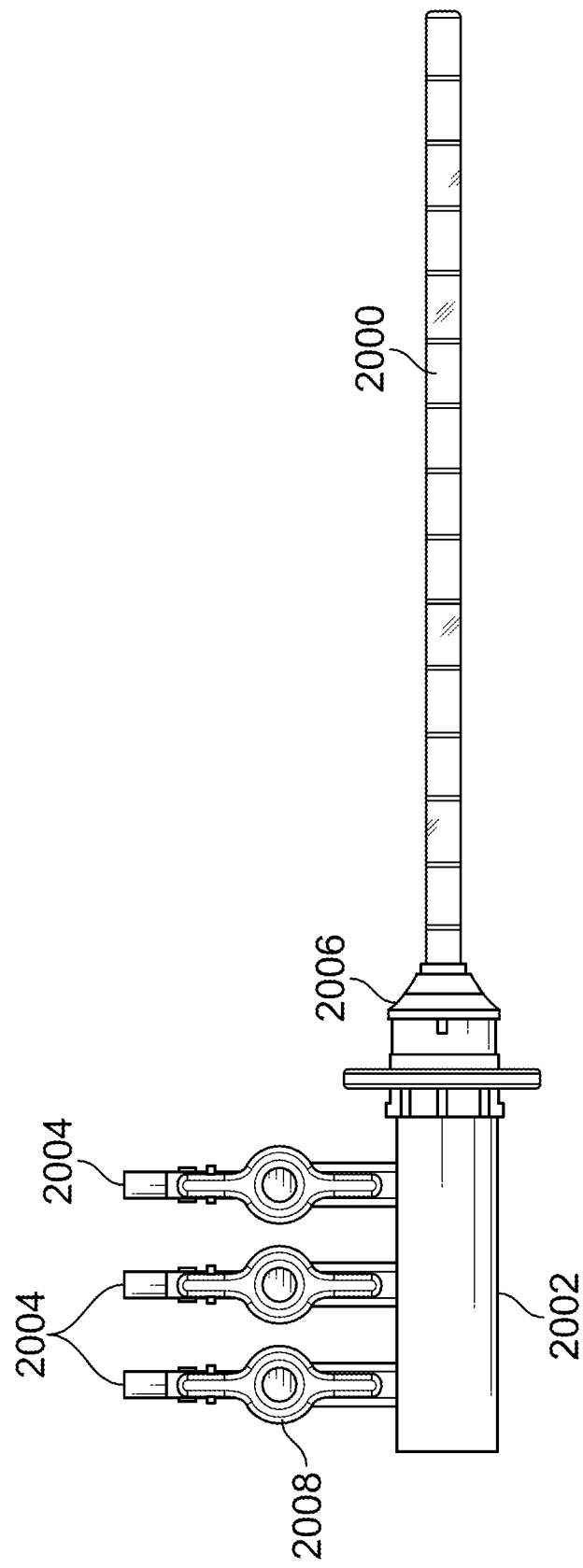
FIG. 20 depicts an exemplary portal cannula including multiple ports for the introduction of working instruments.

The integrated assembly device may also be configured to allow for the removal of an existing depth guide and attachment of another component, e.g., a connector, to the top of the portal cannula that allows insertion of multiple working instruments sequentially or simultaneously into the portal cannula. The connector may facilitate the sequential or simultaneous insertion of visual tools such as endoscopes, energy delivery devices, sensors, and/or other monitoring devices. It may also provide access for irrigation and suction catheters. For example, as shown in FIG. 20, an integrated device may comprise a portal cannula (2000) including a connector (2002) attached thereto via hub (2006). The connector (2002) may include multiple ports (2004) configured for the sequential or simultaneous introduction of various working instruments into the portal cannula (2000), and/or for providing irrigation and/or suction through the portal cannula (2000). In some variations, the connector (2000) may include control mechanisms such as valves (2008) to adjust working parameters. In some variations, the connector may include a power source for any energy delivery devices that may be used.

In some variations, the portal cannula may include two or more lumens for simultaneous insertion of some of working instruments and application of irrigation and/or suction. For example, visualization devices (e.g., an endoscope) may be inserted through one lumen while suction and/or irrigation is deployed through a second lumen to keep the field of view open for better visualization. In some variations, one or a plurality of working instruments, and/or measuring devices may be deployed through the same, or one or more different lumens, than the visualization devices, simultaneously or sequentially. In some variations, visualization devices may not be used, and one or a plurality of working instruments, and/or measuring devices may be advanced through one or more lumens while a separate lumen may be used for application of irrigation and/or suction.

Methods

Methods for accessing a spinal region in a patient are also described herein. The methods may generally include percutaneously introducing a portal cannula of the integrated assembly into the spinal region. The portal cannula may be cannulated with a trocar when introduced. The portal cannula may comprise a distal tip and a proximal hub, with a portal grip slidingly disposed therebetween. After introduction, the portal cannula distal tip may be advanced to a target depth in the spinal region. Once at the target depth, the method may further include removing the trocar, sliding the portal grip along the portal cannula to contact a skin surface of the patient, and locking the portal grip at a position on the cannula to thereby hold or brace the portal cannula distal tip at the target depth. The locked position of the portal grip may be maintained along the length of the portal cannula upon exposure to fatty lipids and/or a body fluid, which may increase the lubricity of the portal cannula surface.

The single access point created by the portal cannula may be used to perform a spinal procedure at multiple spinal levels and/or both sides of the spine. For example, after a procedure is performed on one side of the spine, the portal grip may be unlocked, a trocar may be reinserted into the portal cannula, and the portal cannula may be repositioned on the other side of the spine. The portal grip may then be slid along the portal cannula to again contact the skin surface of the patient and may be re-locked at this position.

The portal grip may include a housing, and rotation of at least a portion of the housing may lock the position of the portal grip on the cannula. When a portion of the housing is spherically shaped, it may comprise a first component coupled to a second component. In this instance, locking the portal grip may include rotating the first component with respect to the second component. In other instances, locking the portal grip may include rotating the housing into axial alignment with the portal cannula.

When the portal grip includes a locking assembly, the locking assembly may comprise a collet concentrically disposed about the portal cannula, and locking the portal grip may include compressing the collet against an outer surface of the portal cannula. Instead of a collet, the locking assembly may include a spiral cam that generally effects locking of the portal grip by tightening of the spiral cam around the outer surface of the portal cannula.

The methods described herein may further include unlocking the portal grip from the portal cannula. Unlocking may be achieved in various ways. For example, unlocking may be accomplished by rotating at least a portion of the housing or by rotating the housing out of axial alignment with the portal cannula. Once unlocked, the portal grip may be slidingly advanced or retracted to a second position along the cannula, and then locked to the portal cannula at the second position. Locking and unlocking the portal grip and changing the position of the portal grip may both be accomplished using a single hand.

In some variations, the methods may include removably coupling the portal cannula to one or more system components. The one or more system components may be a trocar, portal grip, and/or a depth guide. When a depth guide is employed, the method may include receiving feedback, e.g., tactile feedback, when ascertaining an insertion depth using the depth guide. Coupling of the portal cannula to the one or more system components may be achieved in various ways. For example, the proximal end of the portal cannula may be releasably coupled to the trocar by a threaded hub. Additionally or alternatively, the hub may include an outer ring that limits advancement of the trocar.

The methods may be used to perform various spinal procedures. For example, the methods may be used to remove a portion of a ligamentum flavum of the patient, to treat spinal stenosis, and/or to perform a laminectomy. Once percutaneous access to a spinal region is obtained with the systems described herein, instruments may be advanced through a lumen of the portal cannula to perform the procedure. For example, a bone auger, bone rongeur, and/or a tissue sculptor may be deployed through the lumen. The methods may further include percutaneously accessing the spinal canal and performing a spinal procedure in multiple locations along the canal, e.g., bilaterally and/or at multiple levels, from a single access point.

In some variations, the method may first include positioning the patient on the surgical or procedure table in a prone position. The patient may then be draped and prepped in the usual sterile fashion. Anesthesia may be achieved using local or regional anesthesia, and IV sedation. Next, the target spinal region on the patient may be identified and marked with ink. Fluoroscopy and/or surface landmarks may also be used to identify the target region. In some instances, an epidurogram, myelogram, or other nerve highlighting, using contrast media or other suitable material, may be performed under radiography to identify the anatomy.

An integrated assembly comprising a trocar disposed within a portal cannula, a portal grip, and a depth guide, as described herein, may then be used to percutaneously access the target spinal region, e.g., the spinal region in which ligamentum flavum is to be removed. The integrated device may be inserted through the skin and tunneled through tissue until the target spinal region is reached. In some variations, the tunneling may be accomplished under image guidance, e.g., under fluoroscopic guidance. Next, the trocar may be removed from the portal cannula, leaving a distal end of the portal cannula in the target region, e.g., the interlaminar space. Once the portal cannula is positioned, the portal grip may be slid down the cannula to contact the skin surface and locked into place. In some variations, prior to positioning of the portal grip, the distal end of the portal cannula may be used as a bone auger to create a path through hard tissue structures (e.g., bone, calcified tissues). In these variations, the portal cannula may include threads at its distal end, as described above. The threads may be initially covered and/or the space between the threads may be initially filled with any biocompatible material that may be bioabsorbable, biodegradable, or dissolvable such that the portal cannula may be inserted without the threads interfering with its insertion. The bioabsorbable, biodegradable, or dissolvable materials may release medications or other substances to treat the patient, e.g., reduce inflammation, control bleeding, reduce post-op pain, apply anesthesia, etc. These substances may be released from the material as it absorbs, degrades, or dissolves. The materials employed may be configured to absorb, degrade, or dissolve within a few seconds to minutes (e.g., about 5 seconds to about 10 minutes), depending on the particular procedure, surgery, or tissue at the target treatment area.

Working instruments may next be advanced through the portal cannula to perform the spinal procedure, e.g., perform a laminotomy or a laminectomy and debulk the ligamentum flavum. Examples of working instruments may be bone augers, hand-operated mechanical biting instruments such as bone rongeurs, mechanical scooping devices such as tissue sculptors, power-operated mechanical instruments such as grinders and drills, and light guiding and/or visualization devices, e.g., endoscopes. Other examples of working instruments may include suction and irrigation catheters, sensors, monitoring devices, and electric, magnetic, electromagnetic, vibration, sound, and kinetic energy delivering components such as RF probes, ultrasound probes, ablation devices, and energy delivering wires. In some instances, the working instrument may use streams of fluid to modify tissue. If the procedure is to be performed bilaterally or on multiple vertebral levels, the portal grip may be unlocked and the portal cannula withdrawn so that it may be repositioned to a provide access to the next spinal region. For example, upon withdrawal, a trocar may be reinserted into the portal cannula, and the portal cannula may be retracted but not removed from the patient's back. Once repositioned in the spinal region, the trocar may be removed and the portal grip may then be slid along the portal cannula to again contact the skin surface of the patient, and the portal grip may be re-locked at this position. After completion of the spinal procedure, e.g., adequate debulking of the ligamentum flavum has been achieved, the portal grip may be unlocked and the portal cannula and the portal grip may be removed. The wound may then be closed with a sterile adhesive bandage.

In some variations, the bone auger may be used as a portal cannula to access the target treatment area. In these variations, the bone auger and trocar may include a lumen extending therethrough for the passage of a guide wire, various working instruments, or other devices used for access, diagnosis, monitoring, and/or treatment, as previously described herein. For example, the bone auger including a lumen may first be used to create access through hard tissue (e.g., bone, calcified tissue) and then one more working instruments, e.g., a bone rongeur and/or a tissue sculptor, may be deployed through the lumen.

In other variations, the trocar may be used as a portal cannula in addition to providing access through soft tissue. In these variations, the trocar may include a lumen extending therethrough for the passage of a guide wire, various working instruments, or other devices used for access, diagnosis, monitoring, and/or treatment, as previously described herein. Additionally, the trocar may include threads proximal to its sharp tip configured to create a path through hard tissue structures (e.g., bone, calcified tissues). In the same manner described above with respect to the portal cannula, the threads may be initially covered and/or the space between the threads may be initially filled with any biocompatible material that may be bioabsorbable, biodegradable, or dissolvable such that the portal cannula may be introduced through soft tissue without the threads interfering with its insertion. Thus, when employed during a procedure or surgery, the sharp tip of the trocar may first be used to penetrate soft tissue followed by passage through hard tissue after removal (e.g., absorption, degradation, dissolution) of the biocompatible material with the assistance of the threads. The passage through hard tissue may in some instances transform the sharp tip of the trocar into an atraumatic tip (e.g., a blunt or rounded tip shape), or fracture (e.g., break apart) the sharp tip.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated.

What is claimed is:

1. A method for accessing a spinal region in a patient comprising:
    percutaneously introducing an integrated assembly into the spinal region, wherein the integrated assembly comprises:
        a portal cannula having a proximal end and a distal tip, and
        a portal grip comprising a housing slidingly attached to the portal cannula;
    advancing the distal tip of the portal cannula to a target depth in the spinal region;
    sliding the portal grip along the portal cannula to contact a skin surface of the patient; and
    rotating at least a portion of the housing to lock the portal grip at a first position on the portal cannula thereby fixing the distal tip of the portal cannula at the target depth.

2. The method of claim 1, wherein locking the portal grip comprises rotating the housing into axial alignment with the portal cannula.

3. The method of claim 1, further comprising unlocking the portal grip from the portal cannula, wherein unlocking comprises rotating at least the portion of the housing or rotating the housing out of axial alignment with the portal cannula.

4. The method of claim 3, further comprising sliding the portal grip to a second position along the portal cannula, and locking the portal grip at the second position.

5. The method of claim 1, further comprising removing a trocar at least partially disposed within the portal cannula from the portal cannula after locking the portal grip at the first position on the portal cannula.

6. The method of claim 1, wherein the integrated assembly further comprises a depth guide, and further comprising using the depth guide to adjust a distance of extension of a working instrument from the distal tip of the portal cannula.

7. The method of claim 1, further comprising advancing a working instrument through a lumen of the portal cannula.

8. A method comprising:
    percutaneously introducing an integrated assembly into a spinal region, wherein the integrated assembly comprises:
        a portal cannula having a proximal end and a distal tip, and a portal grip comprising a housing slidingly attached to the portal cannula, wherein
a portion of the housing is spherically shaped and comprises a first component coupled to a second component;
advancing the distal tip of the portal cannula to a target depth in the spinal region;
sliding the portal grip along the portal cannula to contact a skin surface of a patient; and
locking the portal grip at a first position on the portal cannula by rotating the first component with respect to the second component thereby fixing the distal tip of the portal cannula at the target depth.

9. A method comprising:
percutaneously introducing an integrated assembly into the spinal region, wherein the integrated assembly comprises:
a portal cannula having a proximal end and a distal tip, and
a portal grip comprising a housing slidingly attached to the portal cannula, wherein the portal grip comprises a locking assembly having a collet disposed about the portal cannula;
advancing the distal tip of the portal cannula to a target depth in the spinal region;
sliding the portal grip along the portal cannula to contact a skin surface of a patient; and
locking the portal grip at a first position on the portal cannula by compressing the collet against an outer surface of the portal cannula thereby fixing the distal tip of the portal cannula at the target depth.

10. The method of claim 9, wherein the collet is configured as a spiral cam, and wherein locking the portal grip comprises tightening the spiral cam around an outer surface of the portal cannula.

11. A method for accessing a spinal region in a patient comprising:
percutaneously introducing an integrated assembly into the spinal region, the integrated assembly comprising a trocar removably disposed within a portal cannula;
advancing the integrated assembly to a target depth in the spinal region;
fixing the portal cannula at the target depth by sliding a portal grip along the portal cannula toward a skin surface of the patient and locking the portal grip at a first position, wherein the portal grip comprises a locking assembly having a collet disposed about the portal cannula, and wherein locking the portal grip comprises compressing the collet against an outer surface of the portal cannula; and
removing the trocar from the portal cannula.

12. The method of claim 11, further comprising identifying a target region of the spinal region using fluoroscopy.

13. The method of claim 11, wherein rotation of at least a portion of the portal grip locks the portal grip at the first position on the portal cannula.

14. The method of claim 11, wherein a portion of the portal grip is spherically shaped and comprises a first component coupled to a second component, and wherein locking the portal grip comprises rotating the first component with respect to the second component.

15. The method of claim 11, further comprising advancing a working instrument through a lumen of the portal cannula.

16. A method for accessing a spinal region in a patient comprising:
percutaneously introducing a portal cannula into the spinal region;
advancing the portal cannula to a target depth in the spinal region;
fixing the portal cannula at the target depth by sliding a portal grip along the portal cannula toward a skin surface of the patient and rotating a component of the portal grip to lock the portal grip at a first position; and
advancing a working instrument through a portal cannula fixed at a target depth in the spinal region.

17. The method of claim 16, further comprising identifying a target region of the spinal region using fluoroscopy.

18. The method of claim 16, wherein a portion of the portal grip is spherically shaped and comprises a first component coupled to a second component, and wherein rotating the component of the portal grip comprises rotating the first component with respect to the second component.

19. The method of claim 16, wherein the portal grip comprises a locking assembly having a collet disposed about the portal cannula, and wherein locking the portal grip comprises compressing the collet against an outer surface of the portal cannula.

* * * * *